United States Patent
Roberts et al.

(10) Patent No.: US 6,939,541 B2
(45) Date of Patent: Sep. 6, 2005

(54) CLONING, OVEREXPRESSION AND THERAPEUTIC USE OF BIOACTIVE HISTIDINE AMMONIA LYASE

(75) Inventors: Joseph Roberts, Columbia, SC (US); Natarajan Sethuraman, Columbia, SC (US); Thomas MacAllister, McLean, VA (US)

(73) Assignee: University of South Carolina, SC (US)

( * ) Notice: Subject to any disclaimer, the term of this patent is extended or adjusted under 35 U.S.C. 154(b) by 0 days.

(21) Appl. No.: 09/833,745

(22) Filed: Apr. 13, 2001

(65) Prior Publication Data

US 2002/0052038 A1 May 2, 2002

Related U.S. Application Data

(60) Provisional application No. 60/197,770, filed on Apr. 14, 2000.

(51) Int. Cl.[7] .............................. A61K 38/51; C12N 9/88
(52) U.S. Cl. ...................................... 424/94.5; 435/232
(58) Field of Search ................................. 435/232, 188; 424/94.5

(56) References Cited

U.S. PATENT DOCUMENTS

| | | | |
|---|---|---|---|
| 4,955,857 A | * | 9/1990 | Shettigar ........................ 604/5 |
| 5,824,784 A | * | 10/1998 | Kinstler et al. .............. 530/351 |

OTHER PUBLICATIONS

Rechiler, M.M. (1969) J. Biol. Chem. 244(3), 551–559.*

Joseph Roberts et al., Biological and Antineoplastic Effects of Enzyme–Medicated In Vivo Deletion of L– L Glutamine, L–Trytophan, and L–Histidine, Cancer Treatment Reports vol. 63, No. 6, Jun. 1979, pps. 1045–1054.

Holcenberg et al., "Enzymes As Drugs", Ann. Rev. Pharmacol, Toxicol, 1977 17:97–116, Copyright 1977 by Annuals Reviews Inc.

Shibatani, et al., Cyrstallin L–Histidine Ammonia–Lyase of Achromobacter liquidum Crystallization and Enzymic Properties, Bur J. Biochem, 5, 263–269 (1975.

Wu et al., "Histidine ammonia–lyase from *Streptomcyes griseus*", 1992 Gene– 115, 19–25.

(Continued)

*Primary Examiner*—Charles L. Patterson, Jr.
(74) *Attorney, Agent, or Firm*—Foley & Lardner LLP

(57) ABSTRACT

Histidine ammonia lyase (HAL) isolated from Corynebacteriaceae can decrease serum histidine levels, induce accumulation of urocanic acid, and is not inhibited by L-histidinol. As a result, histidine ammonia lyases similar to the one isolated from Corynebacteriaceae are uniquely suitable for combination therapy with L-histidinol to treat histidine- and/or histamine-dependent pathologies, for example, infectious viruses, such as human Respiratory Syncytial Virus (RSV), Herpes Simplex Virus (HSV), and Human Immunodeficiency Virus (HIV), as well as cancers.

21 Claims, 26 Drawing Sheets

---

Restriction pattern of the HAL coding region cut with selected enzymes.

HAL

N - Ndel site introduced at the N-terminus
B - BamHI site introduced at the C-terminus
E - EagI      P - PstI      S - SphI

OTHER PUBLICATIONS

Jack et al., "The Effect of Histidine Ammonia–Lyase On Some Murine Tumours", Leukemia Research vol., No. 3, pp. 421–429, 1983.

Khanna et al., "Characterization of L–hisstidine ammonia–lyase immobilized by microencapsulation in artifical Cells: preparation, kinetics, stability and in vitro depletion of histidine", The International Journal of Artifical Organs, vol. 13, No. 3, 1990, pp. 189–195.

Consevage et al., "Sequence Analysis of the butl–Gene Encoding Histifdine Ammonia–Lyase in Pseudomonas Putidfa", Journal of Bacteriology, May 1990, 172 pp. 2224–2229.

Oda et al., "Cloning and Nucleotide Sequences of histidase and Regulatory Genes in the Bacillus subtilis hut Operon and Positive Regulation of the Operon", Journal of Bacterology, Jul. 1988, 172, pp. 3199–3205.

Wu et al., "Purification of Histidase from Streptomyces griseus and Nucleotide Sequence of the hutH Structural Gene", Journal of Bacteriology, Mar. 1992, 170 pp. 1647–1655.

Taylor et al., "Cloning and Expression of Rat Histidase", The Journal of Biological Chemistry, vol. 265, No. 30 Oct. 25, pp. 18192–18199, 1990.

Okamura et al., L–Histidine Ammonia–lyase in Rat Liver, J. Biochem, 75, 139–152, 1974.

Watanabe et al., "Induction of Histidine Decarboxylase Activity in Mouse Skin After Application of Indole Alkaloids, A New Class of Tumor Promoter", Biochemical and Biophysical Research Communications, vol. 109, No. 2, 1982, pp. 478–485.

Bartholeyns et al., "Involvement of Histamine in Growth of Mouse and Rat Tumors: Antitumoral Properties of Monofluoromethylhistidine, and Enzyme–activated Irreversible Inhibitor of Histidine Decarboxylase", Cancer Research 44, 639–645, Feb. 1984.

Hakii et al., "Thapsigargin, a histamine secretagogue, is a non–12–O–testradecanoylphorbol–13–acetate (TPA) Type tumor promoter in two–stage mouse skin carcinogenesis", Cancer Research Clinical Oncology, 1986, 111, 88, 177–180.

Mitra et al., "Histamine and Cis–Urocanic Acid Augment Tumor Necrosis Factor–Alpha Mediated Induction of Keratinocyte Intercellular Adhesion Molecular–1 Expression", Journal of Cellular Physiology 156:348–357, 1993 Wiley–Liss, Inc.

Stolfi et al., "Chemotherapeutic Activity of L–Histidinol against Spontaneous, Autochthonous Murine Breast Tumors", Chemotherapy 1990, 36:435–440.

Warrington et al., L–Histidinol Reverses Resistance to Cisplatinum and Other Antinneoplastics in a Tumorigenic Epithelial Cell Line, Anticancer Research 16:3641–3646, 1996.

Warrington et al., "Reversal of the Multidrug–Resistant Phenotype of Chinese Hamster Ovary Cells by L–Histidinol", Journal of the National Cancer Institute, 81, 798–803, (1984).

Warrington et al., "Improved Treatment of Disseminated B16f10 Melanoma in Mice with Anticancer Drugs in Combination with L–Histidinol", Anticancer Research 11:1869–1874, 1991.

Warrington et al., "Susceptibility of Human Colon Carcinoma Cells to Anticancer Drugs Is Enhanced by L–Histidinol", Anticancer Research 14:367–372, 1994.

Warrington et al., "L–Histidinol Increases the Vulnerability of Cultured Human Leukemia and Lymphona Cells to Anticancer Drugs", Anticancer Research 13:2107–2112, 1993.

Warrington et al., "L–Histidinol in experimental cancer chemotherapy: improving the selectivity and efficacy of Anticancer drugs, eliminating metastatic disease and reversing the multidrug–resistant phenotype", Biochem, Cell Biol., vol. 70, 365–375, 1992.

Zaharko et al., "L–Histidinol: Preclinical Therapeutic Studies in Combination with Antitumor Agents and Pharmacokinetic Studies in Mice", Cancer Research 52, 3604–3609, Jul. 1992.

Warrington et al., "L–Histidinol Selectively Modulates Daunomycin Toxicity in Normal and Tumorigenic Kidney Epithelial Cells", Anticancer Research 16:3629–3634, 1996.

Badary et al., "Effect of L–Histidinol on Cisplatin Nephrotoxicity in the Rat", Neplron (1997) 77, 435–439.

Al–Shabanah et al., "Effects of L–Histidinol On The Antitumor Activity and Acute Cardiotoxicity of Doxorubicin in Mice", Pharmacological Research, vol., 38 No. 3, 1998, 225–230.

Badary, "L–Histidinol Attenuates Fanconi Syndrome Induced by Ifosfamide in Rate", (1991) Exp, Nephiol 9, 325–327.

Zaharko et al., "L–Histidinol: Preclinical Therapeutic Studies in Combination with Antitumor Agents and Pharmacokinetic Studies in Mice", Cancer Research 52, 3604–3609, Jul. 1, 1992.

U.S. Department of Health and Human Services, Hypothermia–Related Deaths, Virginia, Nov. 1996–Apr. 1997, Dec. 12, 1997, vol. 46, No. 49, pp. 1162–1165.

Noonan et al., "Immunosuppression by ultraviolet B radiation: initiation by urocanic acid", Immunology Today, vol. 13, No. 7, 1992, pp. 250–254.

Altschul et al., "Gapped BLAST and PSA–BLAST: a new generation of protein database search programs", Nucleic Acids Research, vol. 25, No. 17, 1997, pp. 3389–3402.

Gish et al., "Identificaiton of protein coding regions by database similarity search", Nature Genetics, vol. 3, 1993, pp. 266–272.

Madden et al., "[9]Applications of Network BLAST Server", Methods in Enzymology, vol. 266, pp. 131–141.

Altschul et al., "Basic Local Alignment Search Tool", J. Mol. Biol. vol. 215, 1990, pp. 403–410.

Zhang et al., "PowerBLAST: A New Network BLAST Application for Interactive or Automated Sequence Analysis and Annotation", Genome Research, vol. 7, 1997, pp. 649–656.

Newman et al., "Selective Killing of Transformed Cells by Methotrexate with Histidine Deprivation or with Amino Alcohols", Cancer Research vol. 43, Oct. 1983, pp. 4703–4708.

Pardee et al., "Animal Cell Cycle", Ann. Rev. Biochem, vol. 47, 1978, pp. 715–750.

Pardee, "A Restriction Point for Controll of Normal Animal Cell Proliferation", Proc. Nat. Acad. Sci., vol. 71, No. 4, 1974, pp. 1286–1290.

Warrington "A Novel Approach for Improving the Efficacy of Experimental Cancer Chemotherapy Using Combinations of Anticancer Drugs and L–Histidinol", Anticancer Research, vol. 6, 1986, 451–464.

Warrington et al., "L–Histidinol in experimental cancer chemotherapy: improving the selectivity and efficacy of anticancer drugs, eliminating metastatic disease and reversing the multidrug–resistant phenotype", Biochem. Cell Biol. vol. 7, 1992, pp. 365–375.

Hanson et al., "Epidermal *trans*–urocanic acid and the UV–A–induced photaging of the skin", Proc. Natl. Acad. Sci., vol. 95, 1998, pp. 10576–10578.

Norval, et al., The Role of Urocanic Acid In Un–Induced Immunosuppression: Recent Advances (1992–1994), Photochemistry and Photobiology, vol. 62, No. 2, 1995, pp. 209–217.

Kripke, "Ultraviolet Radiation and Immunology: Something New Under the Sun–Presidential Address", Cancer Research, vol. 54, 1994, pp. 6102–6105.

Logan et al., "Adenovirus tripartite leader sequence enchances translation of mRNAs late after infection", Proc. Natl. Acad. Sci., vol. 81, Jun. 1994, pp. 3655–3659.

Rosenberg et al., "Grafting Genetically Modified Cells to the Damaged Brain: Restorative Effects of NGF Expression", Science, vol. 242, Dec. 16, 1988, pp. 1575–2578.

Wolff et al.,"Grafting fibroblasts genetically modified to produce L–dopa in a rat model of Parkinson disease",. Proc. Natl. Acad. Sci., vol. 86, Nov. 1989, pp. 9011–9014.

Hodgson, "The Vector Void in Gene Therapy", Bio/Technology vol. 13, Mar. 1995, pp. 222–225.

Caplen et al., "Liposome–mediated CFTR gene transfer to the nasal epithelium of patients with cystic fibrosis", Nature Medicine, vol. 1, No. 1, 1995, pp. 39–46.

Zhu et al., "Systemic Gene Expression After Intravenous DNA Delivery into Adult Mice", Science, vol. 261, Jul. 9, 1993, pp. 209–211.

Berkner, "Development of Adenovirus Vectors for the Expression of Heterologous Genes", BioTechniques,.. vol. 6, No. 7, 1988, pp. 616–626.

Trapnell, "Adenoviral vectors for gene transfer", Advanced Drug Delivery Reviews, vol. 12, 1993, pp. 185–199.

Monks, "Feasibility of a High–Flux Anticancer drug Sceen Using a Diverse Panel of Cultured Human Tumor Cell Lines", Journal of the National Cancer Institute, vol. 83, No. 11, Jun. 5, 1991, pp. 757–766.

De Fabo et al., "Altered skin cytokine environment after UVB irradiation in UCA–deficient Histidinemic C57BL/6–Hal$^{Edi}$ mice," *Photochemistry and Photobiology*, vol. 69, Jun. 1999, pp. 18S–19S, 27$^{th}$ Annual Meeting of the American Society of Photobiology, Washington, DC.

Brand et al., "Histidine ammonia–lyase from liver. Purification properties, and inhibition by Substrate analogues," *Biochemistry*, vol. 15, No. 9, 1976, pp. 1814–1821.

* cited by examiner

Figure 1: Restriction pattern of the HAL coding region cut with selected enzymes.
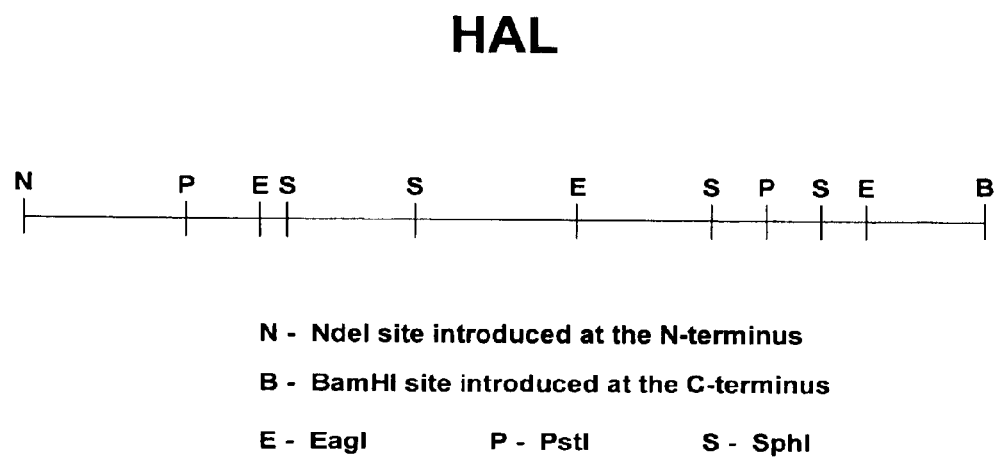

Figure 2: Experimentally derived peptide sequences of HAL

N-terminal
    (M)ASAPQITLGLSGATAD

Internal
    (M)ALADLDELLDEA (M)GEPVEREVLRA

Figure 3: SphI digestion pattern of HAL gene showing oligonucleotide and subclones.
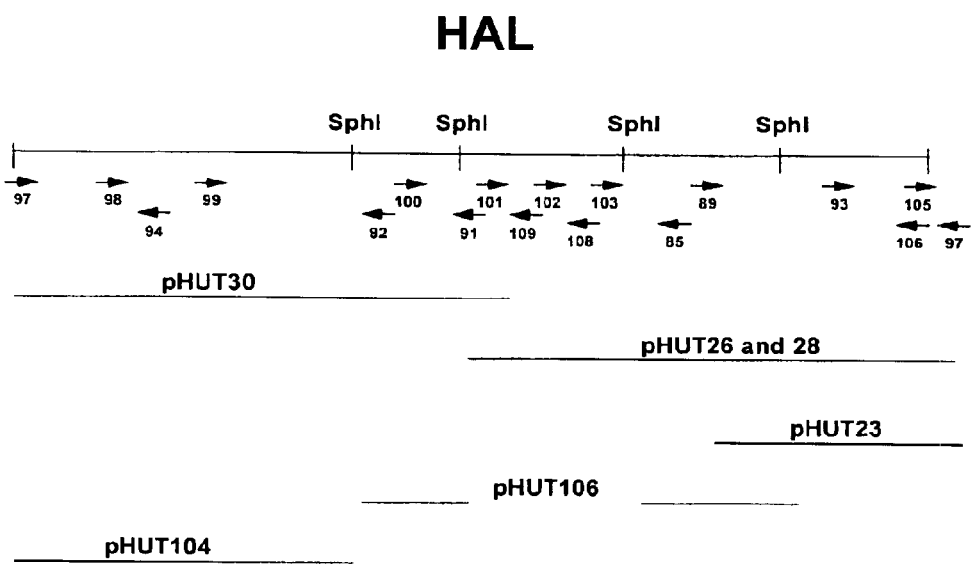

Figure 4: Histidine ammonia lyase overexpressing plasmid.
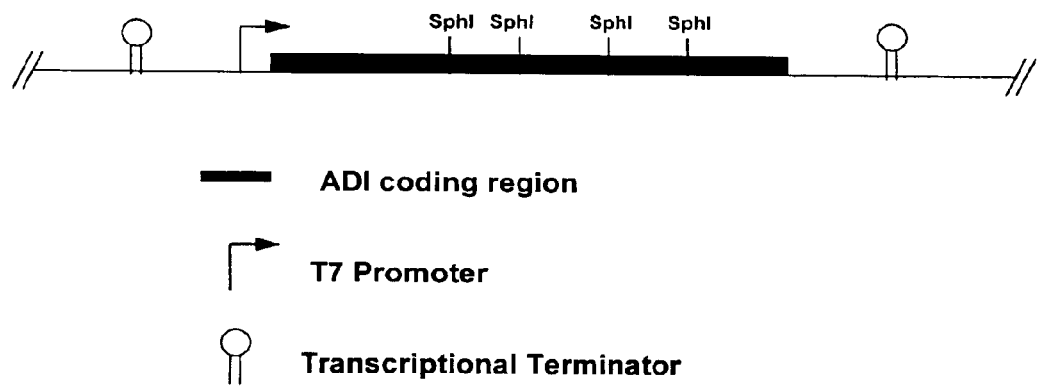

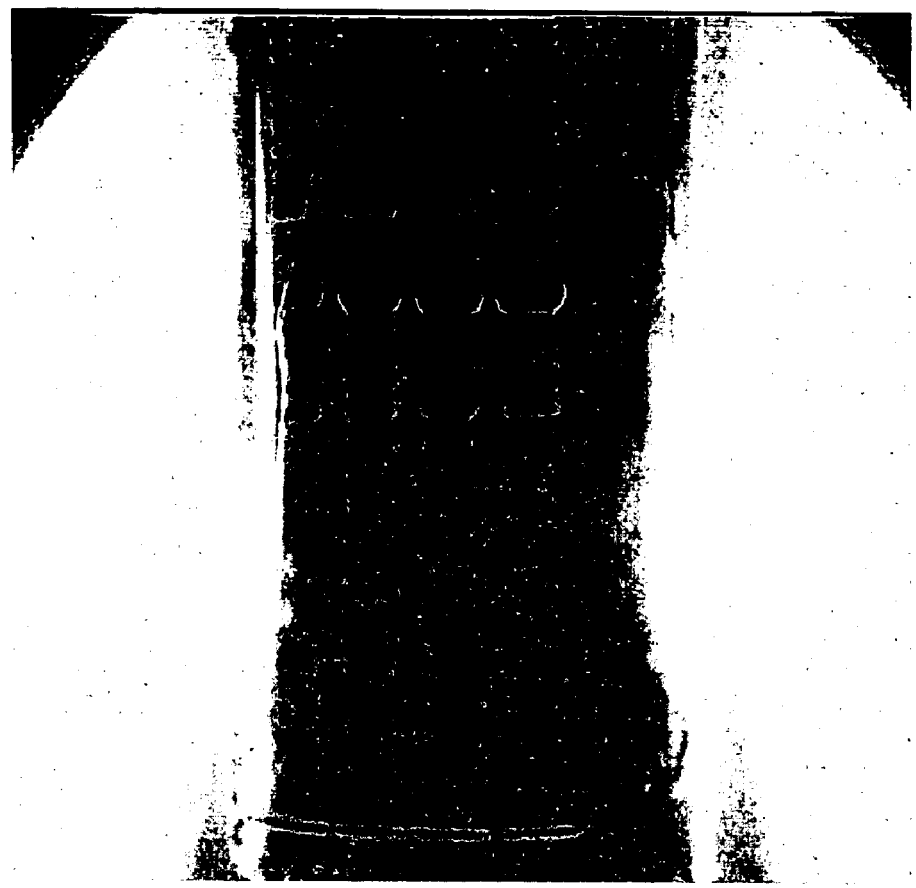
Figure 5: SDS-PAGE showing expression of HAL in *E. coli*.
Lanes:       1    2    3    4

Figure 6: SDS-PAGE showing purification of HAL from E. coli
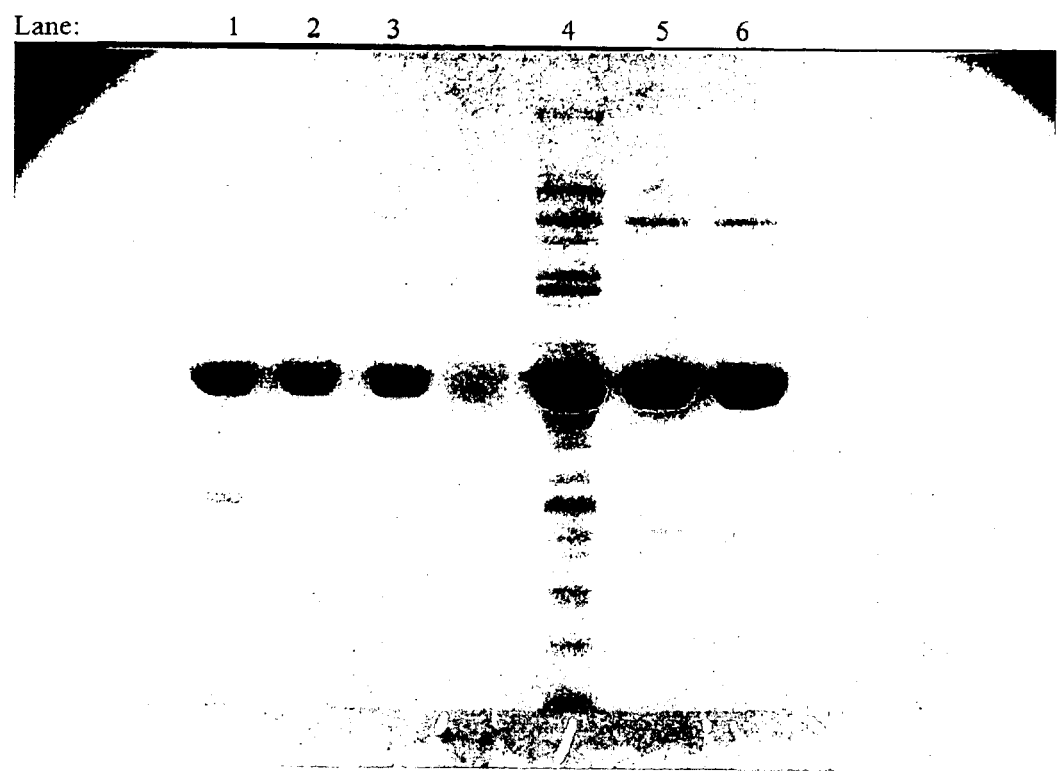

Figure 7: Effect of Temperature on HAL
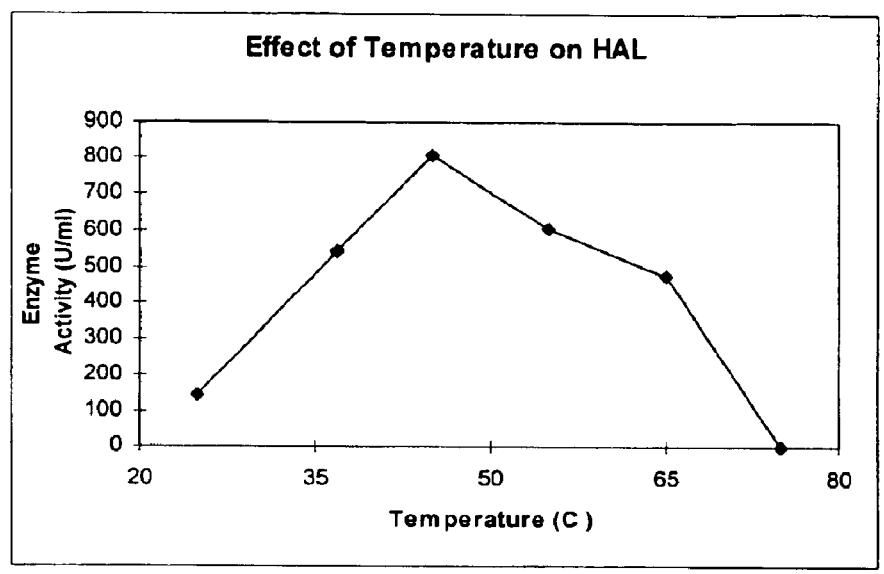

Figure 8: Effect of pH on HAL.
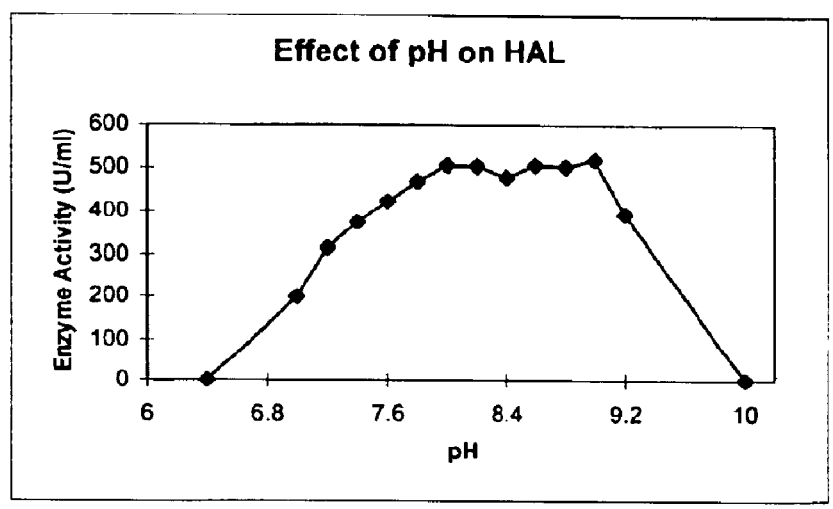

Figure 9: Effect of HAL and Histidinol on HSV.
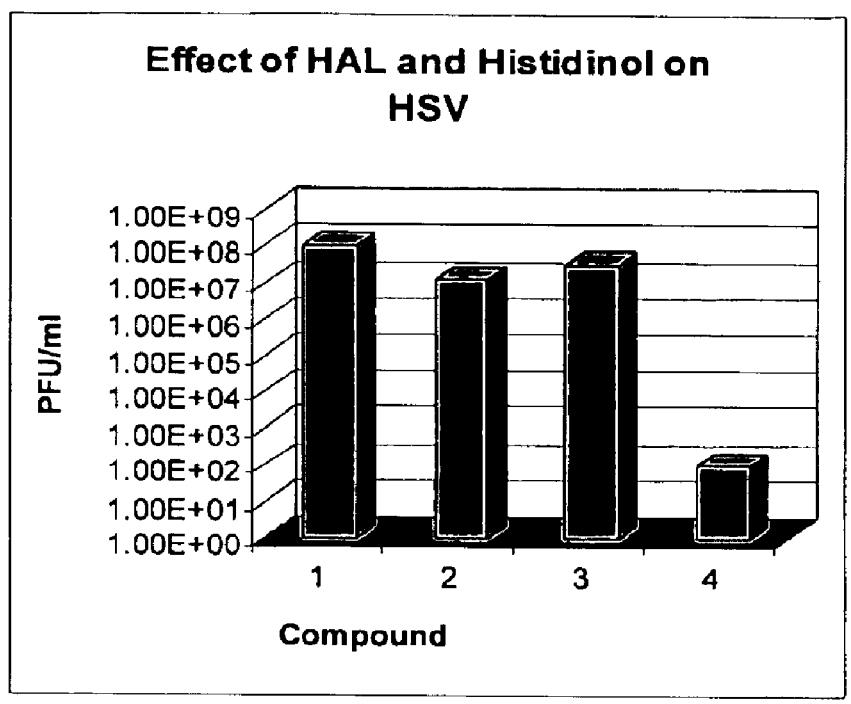

Figure 10: Effectiveness of L-histidinol as a Single Agent
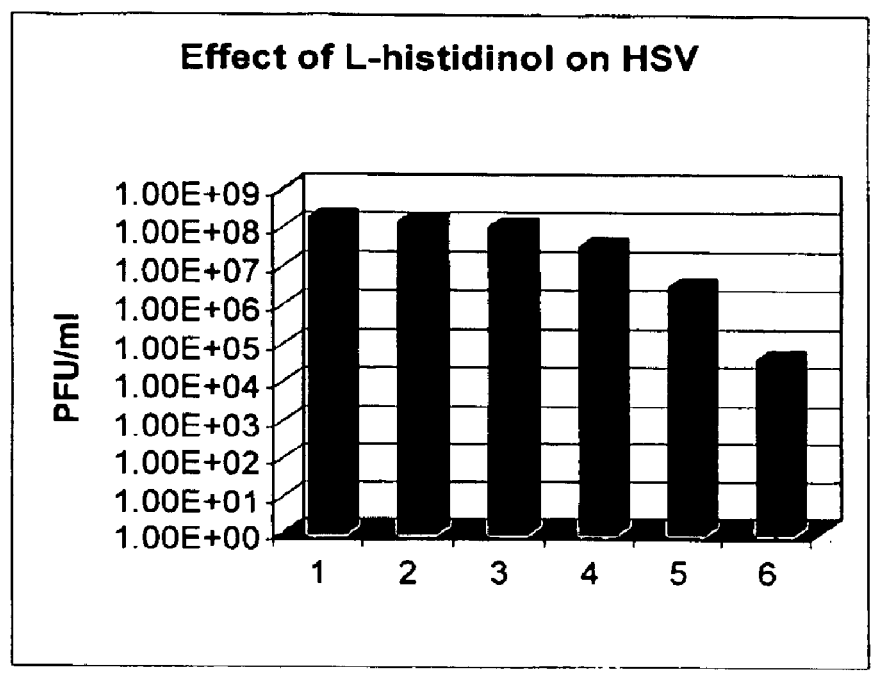

Figure 11: Effect of HAL and Histidinol on RSV.
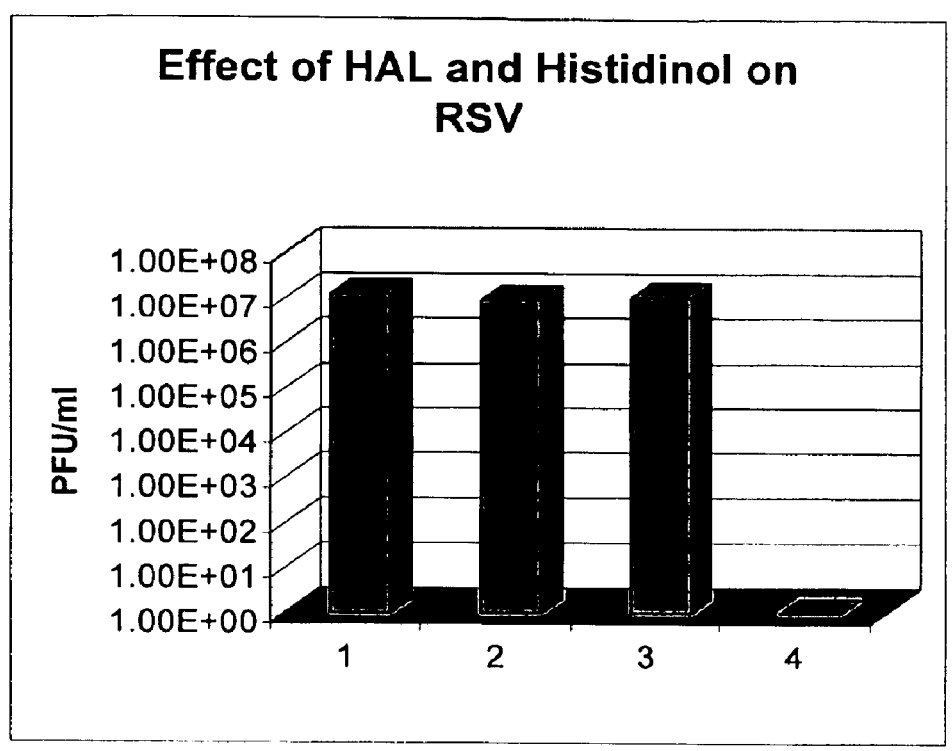

Figure 12: Effect of HAL on RMuLV.

Figure 13A

```
HUTH_PSEPU          ------------------------------------------------------------

HUTH_RHIME          ------------------------------------------------------------

HUTH_MOUSE
MPRYTVHVRGEWLAVPCQDGKLTVGWLGREAVRRYMKNKPDNGGFTSVDEVQFLVHRCKG
HUTH_RAT
MPRYTVHVRGEWLAVPCQDGKLSVGWLGREAVRRYMKNKPDNGGFTSVDEVRFLVRRCKG
HUTH_HUMAN
MPRYTVHVRGEWLAVPCQDAQLTVGWLGREAVRRYIKNKPDNGGFTSVDDAHFLVRRCKG
HUTH_CAEEL          -MRLQVQIGTECVVVPCKP-DDTIHAVAKKSVEKLRRLRPK----
LPLADDYFEVRRTVG
HUTH_BACS           ------------------------------------------------------------

HUTH_STRGR          ------------------------------------------------------------

HUTH_CORY           ------------------------------------------------------------

HUTH_PSEPU          ------------------------------------------------------------

HUTH_RHIME          ------------------------------------------------------------

HUTH_MOUSE          LGLLDNEDELEVALEDNEFVEVVIEGDVMS--------PDFIPSQPEGVFLYSKYR---

HUTH_RAT            LGLLDNEDLLEVALEDNEFVEVVIEGDVMS--------PDFIPSQPEGVFLYSKYR---

HUTH_HUMAN          LGLLDNEDRLEVALENNEFVEVVIEGDAMS--------PDFIPSQPEGVYLYSKYR---

HUTH_CAEEL
NSLLDPEDLVSDVLKDSDFIIVAASVEETEDAKEAKKQEEIDNARAEIEKIDNRRRKVSF
HUTH_BACS           ------------------------------------------------------------

HUTH_STRGR          ------------------------------------------------------------

HUTH_CORY           ------------------------------------------------------------

HUTH_PSEPU          -------------
TELTLKPGTLTLAQLRAIHAAPVRLQLDASAAPAIDASVACVEQIIA
HUTH_RHIME          -------------
MTVILRPGSVPLSDLETIYWTGAPARLDAAFDAGIAKAAARIAEIVA
HUTH_MOUSE          ----------
EPEKYIALDGDSLSTEDLVNLGKGRYKIKLTSIAEKKVQQSREVIDSIIK
HUTH_RAT            ----------
EPEKYIALDGDSLSTEDLVNLGKGHYKIKLTSIAEKKVQQSREVIDSIIK
HUTH_HUMAN          ----------
EPEKYIELDGDRLTTEDLVNLGKGRYKIKLTPTAEKRVQKSREVIDSIIK
HUTH_CAEEL
ADSLAPMVLAPPTKLLILDGNSLLPEDLVRCEKGECAIQLSMESEDRIRKARTFLEKIAS
HUTH_BACS           ---------------
MVTLDGSSLTTADVARVLFDFEEAAASEESMERVKKSRAAVERIVR
HUTH_STRGR          ----------
MDMHTVVVGTSGTTAEDVVAVARHGARVELSAAAVEALAAARLIVDALAA
HUTH_CORY           ---------
MASAPQITLGLSGATADDVIAVARHEARISISPQVLEELASVRAHIDALAS
```

Figure 13B

```
HUTH_PSEPU
EDRTAYGINTGFGLLASTRIASHDLENLQRSLVLSHAAGIGAPLDDDLVRLIMVLKINSL
HUTH_RHIME
GNAPVYGINTGFGKLASIKIDSSDVATLQRNLILSHCCGVGQPLTEDIVRLIMALKLISL
HUTH_MOUSE
ERTVVYGITTGFGKFARTVIPANKLQELQVNLVRSHSSGVGKPLSPERCRMLLALRINVL
HUTH_RAT
ERTVVYGITTGFGKFARTVIPANKLQELQVNLVRSHSSGVGKPLSPERCRMLLALRINVL
HUTH_HUMAN
EKTVVYGITTGFGKFARTVIPINKLQELQVNLVRSHSSGVGKPLSPERCRMLLALRINVL
HUTH_CAEEL
EHRAVYGVTTGFGTFSNVTIPPEKLKKLQLNLIRSHATGYGEPLAPNRARMLLALRINIL
HUTH_BACS
DEKTIYGINTGFGKFSDVLIQKEDSAALQLNLILSHACGVGDPFPECVSRAMLLLRANAL
HUTH_STRGR
KPEPVYGVSTGFGALASRHIGTELRAQLQRNIVRSHAAGMGPRVEREVVRALMFLRLKTV
HUTH_CORY
ADTPVYGISTGFGALATRHIAPEDRAKLQRSLIRSHAAGMGEPVEREVVRALMFLRAKTL

HUTH_PSEPU
SRGFSGIRRKVIDALIALVNAEVYPHIPLKGSVGASGDLAPLATMSLVLLGEGKARYKGQ
HUTH_RHIME
GRGASGVRLELVRLIEAMLDKGVIPLIPEKGSVGASGDLAPLAHMAAVMMGHGEAFFAGE
HUTH_MOUSE
AKGYSGISLETLKQVIEAFNASCLSYVPEKGTVGASGDLAPLSHLALGLIGEGKMWSPKS
HUTH_RAT
AKGYSGISLETLKQVIEVFNASCLSYVPEKGTVGASGDLAPLSHLALGLIGEGKMWSPKS
HUTH_HUMAN
AKGYSGISLETLKQVIEMFNASCLPYVPEKGTVGASGDLAPLSHLALGLVGEGKMWSPKS
HUTH_CAEEL
AKGHSGISVENIKKMIAAFNAFCVSYVPQQGTVGCSGDLCPLAHLALGLLGEGKMWSPTT
HUTH_BACS
LKGFSGVRAELIEQLLAFLNKRVHPVIPQQGSLGASGDLAPLSHLALALIGQGEVFFEGE
HUTH_STRGR
ASGHTGVRPEVAQTMADVLNAGITPVVHEYGSLGCSGDLAPLSHCALTLMGEGEAEGPDG
HUTH_CORY        ASGRS-
VRPVVLETMVGMLNAGITPVVREYGSLGCSGDLAPLSHCALVLMGEGEATDAHG

HUTH_PSEPU      -
WLSATEALAVAGLEPLTLAAKEGLALLNGTQASTAYALRGLFYAEDLYAAAIACGGLSV
HUTH_RHIME      -
RMKGDAALKAAGLSPVTLAAKEGLALINGTQVSTALALAGLFRAHRAGQAALITGALST
HUTH_MOUSE
GWADAKYVLEAHGLKPIVLKPKEGLALINGTQMITSLGCEALERASAIARQADIVAALTL
HUTH_RAT
GWADAKYVLEAHGLKPIVLKPKEGLALINGTQMITSLGCEAVERASAIARQADIVAALTL
HUTH_HUMAN
GWADAKYVLEAHGLKPVILKPKEGLALINGTQMITSLGCEAVERASAIARQADIVAALTL
HUTH_CAEEL
GWQPADVVLKKNNLEPLELGPKEGLALINGTQMVTALGAYTLERAHNIARQADVIAALSL
HUTH_BACS       -
RMPAMTGLKKAGIQPVTLTSKEGLALINGTQAMTAMGVVAYIEAEKLAYQTERIASLTI
HUTH_STRGR
TVRPAGELLAAHGIAPVELREKEGLALLNGTDGMLGMLVMALADLRNLYTSADITAALSL
HUTH_CORY
DIRPVPELFAEAGLTPVELAEKEGLALVNGTDGMLGQLIMALADLDELLDIADATAAMSV
```

Figure 13C

```
HUTH_PSEPU       EAVLGSRSPFDARIHE-ARGQRGQIDTAACFRDLLGDSSEVSLSHKNCD----
KVQDPYS
HUTH_RHIME       DAAMGSSAPFHPDIQH-CAAIRARSTRAAALRQLLTG-SPIRQSHIEGDE---
RVQDPYC
HUTH_MOUSE       EVLKGTTKAFDTDIHA-VRPHRGQIEVAFRFRSLLDS-
DHHPSEIAESHRFCDRVQDAYT
HUTH_RAT         EVLKGTTKAFDTDIHA-VRPHRGQIEVAFRFRSLLDS-
DHHPSEIAESHRFCDRVQDAYT
HUTH_HUMAN       EVLKGTTKAFDTDIHA-LRPHRGQIEVAFRFRSLLDS-
DHHPSEIAESHRFCDRVQDAYT
HUTH_CAEEL       DVLKGTTRAYDPDIHR-IRPHRGQNLSALRLRALLHS-
EANPSQIAESHRNCTKVQDAYT
HUTH_BACS        EGLQGITDAFDEDIHL-ARGYQEQIDVAERIRFYLSD-SGLTTSQGE-----
LRVQDAYS
HUTH_STRGR       EALLGTDKVLAPELHA-IRPHPGQGVSADNMSRVLAG-SGLTGHHQDDAP---
RVQDAYS
HUTH_CORY        EAQLGTDQVFRAELHEPLRPHPGQGRSAQNMFAFLAD-SPIVASHREGDG---
RVQDAYS

HUTH_PSEPU
LRCQPQVMGACLTQLRQAAEVLGIEANAVSDNPLVFAAEGDVISGGNFHAEPVAMAADNL
HUTH_RHIME       IRCQPQVDGACLDLLRSVAATLTIEANAVTDNPLVLSDN-
SVVSGGNFHAEPVAFAADQI
HUTH_MOUSE
LRCCPQVHGVVNDTIAFVKDIITTELNSATDNPMVFASRGETISGGNFHGEYPAKALDYL
HUTH_RAT
LRCCPQVHGVVNDTIAFVKDIITTELNSATDNPMVFASRGETISGGNFHGEYPAKALDYL
HUTH_HUMAN
LRCCPQVHGVVNDTIAFVKNIITTELNSATDNPMVFANRGETVSGGNFHGEYPAKALDYL
HUTH_CAEEL
LRCVPQVHGVVHDTIEFVREIITTEMNSATDNPLVFADREEIISGGNFHGEYPAKALDFL
HUTH_BACS
LRCIPQVHGATWQTLGYVKEKLEIEMNAATDNPLIFNDGDKVISGGNFHGQPIAFAMDFL
HUTH_STRGR       VRCAPQVNGAGRDTLDHAALVAGRELASSVDNPVVLPDG-
RVESNGNFHGAPVAYVLDFL
HUTH_CORY        LRCSPQVTGAARDTIAHARLVATRELAAAIDNPVVLPSG-
EVTSNGNFHGAPVAYVLDFL

HUTH_PSEPU       ALAIAEIGSLSERRISLMMDKHMS-
QLPPFLVENGGVNSGFMIAQVTAAALASENKALSH
HUTH_RHIME
ALAVCEIGAISQRRIALLVDPALSLRLPAFLAKKPGLNSGLMIAEVTSAALMSENKQLSH
HUTH_MOUSE       AIGVHELAAISERRIERLCNPSLS-
ELPAFLVAEGGLNSGFMIAHCTAAALVSESKALCH
HUTH_RAT         AIGVHELAAISERRIERLCNPSLS-
ELPAFLVAEGGLNSGFMIAHCTAAALVSESKALCH
HUTH_HUMAN       AIGIHELAAISERRIERLCNPSLS-
ELPAFLVAEGGLNSGFMIAHCTAAALVSENKALCH
HUTH_CAEEL       AIAVAELAQMSERRLERLVNKELS-
GLPTFLTPDGGLNSGFMTVQLCAASLVSENKVLCH
HUTH_BACS        KIAISELANIAERRIERLVNPQLN-
DLPPFLSPHPGLQSGAMIMQYAAASLVSENKTLAH
HUTH_STRGR
AIVAADLGSICERRTDRLLDKNRSHGLPPFLADDAGVDSGLMIAQYTQAALVSEMKRLAV
HUTH_CORY
AIAVADLGSIAERRTDRMLDPARSRDLPAFLADDPGVDSGMMIAQYTQAGLVAENKRLAV
```

Figure 13D

```
HUTH_PSEPU      PHSVDSLPTSANQEDHVSMAPAAGKRLWEMAENTRGVPAIEWLGACQGLDLRKG-LKTS
HUTH_RHIME      PASVDSTPTSANQEDHVSMACHGARRLLQMTENLFSIIGIEALAAVQGIEFRAP-LTTS
HUTH_MOUSE      PSSVDSLSTSAATEDHVSMGGWAARKALRVVEHVEQVLAIELLAACQGIEFLRP-LKTT
HUTH_RAT        PSSVDSLSTSAATEDHVSMGGWAARKALRVIEHVEQVLAIELLAACQGIEFLRP-LKTT
HUTH_HUMAN      PSSVDSLSTSAATEDHVSMGGWAARKALRVIEHVEQVLAIELLAACQGIEFLRP-LKTT
HUTH_CAEEL      PSSVDSIPTSCNQEDHVSMGGFAARKALTVVEHVEAVLAMELLAACQGIEFLKP-LIST
HUTH_BACS       PASVDSIPSSANQEDHVSMGTIAARHAYQVIANTRRVIAIEAICALQAVEYRGI-EHAA
HUTH_STRGR
PASADSIPSSAMQEDHVSMGWSAARKLRTAVDNLARIVAVELYAATRAIELRAAEGLTPA
HUTH_CORY       PA-VDSIPSSAMQEDHVSLGWHAARKLPTSVANLRRILAVEMLIAGRALDLRAP-LKPG

HUTH_PSEPU      AKLEKARQALRSEVA-HYDRDRFFAPDIEKAVELLAKG---S-LTGLLPAGVLPSL---
-
HUTH_RHIME      PELQKAAAAVRGVSS-SIEEDRYMADDLKAAGDLVASG---R-LAAAVSAGILPKLEN-
HUTH_MOUSE      TPLEKVYDLVRSVVR-
PWIKDRFMAPDIEAAHRLLLDQKVWEVAAPYIEKYRMEHIPESR
HUTH_RAT        TPLEKVYDLVRSVVR-
PWIKDRFMAPDIEAAHRLLLDQKVWEVAAPYIEKYRMEHIPESR
HUTH_HUMAN      TPLEKVYDLVRSVVR-
PWIKDRFMAPDIEAAHRLLLEQKVWEVAAPYIEKYRMEHIPESR
HUTH_CAEEL      APLHKIYQLVRSVAP-
PLNEDRYMKPEIDAVLEMIRENRIWEAVLPHLETLEAMEELDPD
HUTH_BACS       SYTKQLFQEMRKVVP-SIQQDRVFSYDIERLTDWLKK----ESLIPDHQNKELRGMNI-
HUTH_STRGR      PASEAVVAALRAAGAEGPGPDRFLAPDLAAADTFVREG---R-LVAAVEPVTGPLA---
-
HUTH_CORY       PATGAVLEVLRSKVA-GPGQDRFLSAELEAAYDLLANG---S-VHKALEAHLPE-----
-

HUTH_PSEPU      ------------------------
HUTH_RHIME      ------------------------
HUTH_MOUSE      PLSPTAFSLESLRKNSATIPESDDL----
HUTH_RAT        PLSPTAFSLESLRKNSATIPESDDL----
HUTH_HUMAN      PLSPTAFSLQFLHKKSTKIPESEDL----
HUTH_CAEEL      ALRQFTKTPTGIVQDRSMIPISDDEESIE
HUTH_BACS       ------------------------
HUTH_STRGR      ------------------------
HUTH_CORY       ------------------------
```

Figure 14A

```
                            1                                                                               . 80
   983831           100.0%  MASAPQITLGLSGATADDVIAVARHEARISISPQVLEELASVRAHIDALASADTPVYGISTGFGALATRHIAPEDRAKLQ
 1 SWALL:CAC21618    66.1%  ---MHTVVVGTSGVTASDVLAVARAGARIELSEEAVAALAAARSVVDALAAKPDPVYGVSTGFGALATRHISPELRGRLQ
 2 SWALL:HUTH_STRGR  65.4%  -MDMHTVVVGTSGTTAEDVVAVARHGARVELSAAAVEALAAARLIVDALAAKPEPVYGVSTGFGALASRHIGTELRAQLQ
 3 SWALL:HUTH_DEIRA  46.8%  ------MILDRDLNLEQFISVVRHGEQVELSAAARERIARARTVIEQIVEGDTPIYGFKFENVQIDRSQLAQLQ
 4 SWALL:BAB16159    42.0%  -------------VPLHHLADIYWNNGSAKLDPSFDAAVLKGAARIAELAAGNAPVYGINTGFGKLASIKIDAADLATLQ
 5 SWALL:Q9KWE4      42.0%  -------------VPLHHLADIYWNNGSAKLDPSFDAAVLKGAARIAEIAAGNAPVYGINTGFGKLASIKIDAADLATLQ
 6 SWALL:HUTH_BACSU  40.4%  ---MVTLDGSSLTTADVARVLFDFEEAAASEESMERVKKSRAAVERIVRDEKTIYGINTGFGKFSDVLIQKEDSAALQ
 7 SWALL:Q9KSQ4      42.2%  ---MLHLMIKPGQLSLKQLRQVSRSPVVLSLDPEAIPAIAESAQVVEQVISEGRTVYGINTGFGLLANTKIAPQDLETLQ
 8 SWALL:Q9HU85      41.7%  ---MSLHLKPGQLTLADLRQAYLAPVRLSLDPSADAPIAASVACVENIIAEGRTAYGINTGFLLASTRISPADLEKLQ
 9 SWALL:Q9KBE6      39.3%  ---MTNLKLLDGRSLSLHDLHRIIYEGETVGASDESMEKVKQSRKAVEQIVADEKIIYGITTGFGKFESDIFIDPDDVENLQ
10 SWALL:HUTH_PSEPU  41.7%  ----TELTLKPGTLTLAQLRAIHAAPVRLQLDASAAPAIDASVACVEQIIAEDRTAYGINTGFGLLASTRIASHDLENLQ
11 SWALL:HUTH_RHIME  40.6%  ----LRPGSVPLSDLETIYWTGAPARLDAAFDAGIAKAAARIAEIVAGNAPVYGINTGFGKLASIKIDSSDVATLQ
12 SWALL:Q9HU90      40.7%  MSDLPSVVFGDGPLRWQELVAVARHGARLELSAAAWARIDNARAIVCRIVANGERAYGISTGLGALCDVLLEGEQLAELS
13 SWALL:HUTH_HUMAN  39.2%  KYREPEKYIELDGLTTEDLVNLGKGRYKIKLTPTAEKRVQKSREVIDSIIKERTVVYGITTGFGKFA-RTVIPINKLQLQ
14 SWALL:HUTH_CAEEL  38.8%  VLAPPTKLLILDGNSPEDLVRCEKGECAIQLSMESEDRIRKARTFLEKIASEHRAVYGVTTGFGTFSNVTIPPEKLKKLQ
15 SWALL:Q9HLI6      41.0%  ------MIEIDGRSLRVEDVYAVAVEYDRVSISDDTLKAVEEKHEAFLKLINSGKTVYGVNTGFGSLLNVHIERDQEIELQ
16 SWALL:HUTH_MOUSE  38.6%  KYREPEKYIALDGDSTEDLVNLGKGRYKIKLTSIAEKKVQQSREVIDSIIKERTVVYGITTGFGKFA-RTVIPANKLQLQ
17 SWALL:BAB29407    38.6%  KYREPEKYIALDGDSTEDLVNLGKGRYKIKLTSIAEKKVQQSREVIDSIIKERTVVYGITTGFGKFA-RTVIPANKLQLQ
18 SWALL:HUTH_RAT    38.2%  KYREPEKYIALDGDSTEDLVNLGKGHYKIKLTSIAEKKVQQSREVIDSIIKERTVVYGITTGFGKFA-RTVIPANKLQLQ
19 SWALL:AAG53586    39.8%  ---MNALTLTPGTLTLAQLRQVWQQPLQLTLDESAHEAINDSVACVEAIVAEGRTAYGINTGFGLLAQTRIATHDLENLQ
20 SWALL:Q9KKE0      38.9%  ---MGEMISLDGPLTWREIASIAEGASLDLSGPARLRIAQARRIVDALVERGIRGYGINTGVGALCDVISRENQQALS
21 SWALL:Q9HQD5      42.2%  --------------------------------MSDTRIDAADREALQ
```

Figure 14B

```
                        1                                                                               160
            |           .         .         .         .         .         .         .         .         |
   983831   RSLIRSHAAGMGEPVEREVVRALMFLRAKTLASGRTGVRPVVLETMVGMLNAGITPVVREYGSLGCSGDLAPLSHCALVL   100.0%
 1 SWALL:CAC21618    RNIVRSHAAGMGPRVEREVVRALMFLRLRKTVCSGRTGVRPEVAQTMADVLNAGITPVVHEYGSLGCSGDLAPLSHCALTL   66.1%
 2 SWALL:HUTH_STRGR  RNIVRSHAAGMGPRVEREVVRALMFLRLRKTVASGHTGVRPEVAQTMADVLNAGITPVVHEYGSLGCSGDLAPLSHCALTI   65.4%
 3 SWALL:HUTH_DEIRA  HNLIVSHAIGMGEPLPAEVVRGMLLRAQSLSLGHSGVRVEVELLLALLNADALPVPSQGSVGASGDLAPLAHLALGL       46.8%
 4 SWALL:BAB16159    RNLILSHCCGVGAPLPENVVRLIMALKLISLGRGASGVRIELIRLIEGMLEKGVIPVIPEKGSVGASGDLAPLAHMSATM   42.0%
 5 SWALL:Q9KWE4      RNLILSHCCGVGAPLPENVVRLIMALKLISLGRGASGVRIELIRLIEGMLEKGVIPVIPEKGSVGASGDLAPLAHMSATM   42.0%
 6 SWALL:HUTH_BACSU  LNLILSHACGVGDPFPECVSRAMLLRANALLKGFSGVRAELIEQLLAFLNKRVHPVIPQQGSLGASGDLAPLSHLALAL    40.4%
 7 SWALL:Q9KSQ4      KSIVLSHAAGIGELMSDETVRLMMLLKINSLARGYSGIRLEVIQALIELVNNQIYPCVPKKGSVGASGDLAPLAHMSTVL   42.2%
 8 SWALL:Q9HU85      RSIVLSHAAGVGEALDDAMVRLIVMLLKVNSLARGFSGIRRKVIDALIALINAEVYPHIPLKGSVGASGDLAPLAHMSLVL   41.7%
 9 SWALL:Q9KBE6      HNLIYSHACGVGSPFPETVSRTMLVLRANALLKGFSGVRPLVIERLLALVNANIHPVIPQQGSLGASGDLAPLSHLALVL    39.3%
10 SWALL:HUTH_PSEPU  RSLVLSHAAGIGAPLDDDLVRLIMVLKINSLSRGFSGIRRKVIDALIALVNAEVYPHIPLKGSVGASGDLAPLAHMSLVL   41.7%
11 SWALL:HUTH_RHIME  RNLILSHCCGVGQPLTEDIVRLIMALKLISLGRGASGVRLELVRLIEAMLDKGVIPLIPEKGSVGASGDLAPLAHMAAVM   40.6%
12 SWALL:Q9HU90      RNTLLSHACGVGEPLRDEQTRAIICAAVANYSQGKSGLDRSLVEGLLALLNHGITPQVPAQGSVGY---LTHMAHVGIAL   40.7%
13 SWALL:HUTH_HUMAN  VNLVRSHSSGVGKPLSPERCRMLLALRINVLAKGYSGISLETLKQVIEMFNASCLPYVVPEKGTVGASGDLAPLSHLALGL   39.2%
14 SWALL:HUTH_CAEEL  LNIRSHATGYGEPLAPNRARMLLALRINILAKGHSGISVENIKKMIAAFNAFCVSYVPQQGTVGCSGDLCPLAHLALGL    38.8%
15 SWALL:Q9HLI6      LNLIRSHSSGVGDYLENRYVRAIMAVRLNSLAAGYSAVSADLLNMMVEMLNRDVIPAVPKYGSVGASGDLAPLAHIGLAM   41.0%
16 SWALL:HUTH_MOUSE  VNLIRSHSSGVGKPLSPERCRMLLALRINVLAKGYSGISLETLKQVIEAFNASCLSYVPEKGTVGASGDLAPLSHLALGL   38.6%
17 SWALL:BAB29407    VNLVRSHSSGVGKPLSPERCRMLLALRINVLAKGYSGISLETLKQVIEAFNASCLSYVPEKGTVGASGDLAPLSHLALGL   38.6%
18 SWALL:HUTH_RAT    VNLVRSHSSGVGKPLSPERCRMLLALRINVLAKGYSGISLETLKQVIEVFNASCLSYVPEKGTVGASGDLAPLSHLALGL   38.2%
19 SWALL:AAG53586    RSLVLSHAAGVGEPLDDDIVRLMMVLKINSLARGFSGIRLSVIQALIALVNAGVYSVDPAKGSVGASGDLAPLAHMSLTL   39.8%
20 SWALL:Q9KKE0      RNIILSHACGVGDPLGRVEARAVMAAQIANLTHGYSGVRVETAEMLLALLNADIIPLIPSRGSVGY------LTHAALVL   38.9%
21 SWALL:Q9HQD5      ANLVRSHAAGAGSELDTAAVRALLVTRLNALAKGYSGIRERVLDVLVGLLNEGVHPVVPSRGSLGASGDLAPLAHMSRVL   42.2%
```

Figure 14C

```
                         161                                                                                                                                                         240
    983831          100.0%  MGEGEATDAHGDIRPVPELFAEAGLTPVELAEKEGLALVNGTDGMLGQLIMALADLDELLDIADATAAMSVEAQLGTDQV
 1  SWALL:CAC21618   66.1%  MGEGDAEGPDGTVRPAGELLAAHGIAPVELREKEGLALLNGTDGMLGMLVMALADLDTLYKSADITAALTMEALLGTDRV
 2  SWALL:HUTH_STRGR 65.4%  MGEGEAEGPDGTVRPAGELLAAHGIAPVELREKEGLALLNGTDGMLGMLVMALADLRNLYTSADITAALSLEALLGTDKV
 3  SWALL:HUTH_DEIRA 46.8%  IGLGDI-EYQGQVRPAADVLAELGLSPVQLQAKEGLALINGTQLMGSLLALALHDAQVLLGTANLAAAMTVEARYGSHRP
 4  SWALL:BAB16159   42.0%  MGEGEAF-YQGVQMPSKDALAKAGLSPVVLAAKEGLALINGTQTSTALALAGLFRAHRAAQSALVTGALSTDAAMGSSAP
 5  SWALL:Q9KWE4     42.0%  MGEGEAF-YQGVQMPSKDALAKAGLSPVVLAAKEGLALINGTQTSTALALAGLFRAHRAAQSALVTGALSTDAAMGSSAP
 6  SWALL:HUTH_BACSU 40.4%  IGQGEVF-FEGERMPAMTGLKKAGIQPVTLTSKEGLALINGTQAMTAMGVVAYIEAEKLAYQTERIASLTIEGLQGIIDA
 7  SWALL:Q9KSQ4     42.2%  LGEGQAR-YNGKIISGLEAMKIAGLEPITLAPKEGLTLAAKEGLALINGTQASTAFALEGLFVAEDLFASATVCGAMSVEAALGSRRP
 8  SWALL:Q9HU85     41.7%  IGESRARH-RGEWLPAAEALAVAGLEPLTLAAKEGLALINGTQVSTAYALRGLFEAEDLFAAATVCGGLSVEAMLGSRAP
 9  SWALL:Q9KBE6     39.3%  LGEGEVF-YKGTKTKASFALKEEIEPITLTAKEGLALINGTQASTAYALRGLFYAEDIYAAAIACGGLSVEAVLGSRSP
10  SWALL:HUTH_PSEPU 41.7%  LGEGKAR-YKGQWLSATEALAVAGLEPLTLAAKEGLALINGTQASTAYALRGLFYAEDIYAAAIACGGLSVEAVLGSRSP
11  SWALL:HUTH_RHIME 40.6%  MGHGEAFFAGERMKGDAALKA-AGLSPVTLAAKEGLALINGTQVSTALALAGLFRAHRAGQAALITGALSTDAAMGSSAP
12  SWALL:Q9HU90     40.7%  LGIGEVS-YRGSVVPAAAIAAEGLATVRLGAKDGLCLVNGTPCMTGLACLAIDDAQRLAQWADVIGAMSFEALRGQLAA
13  SWALL:HUTH_HUMAN 39.2%  VGEGKMWSPKSGWADAKYVLEAHGIKPVILKPKEGLALINGTQMITSLGCEAVERASAIARQADIVAALTLEVLKGTTKA
14  SWALL:HUTH_CAEEL 38.8%  LGEGKMWSPTTGWQPADVVLKKNNLEPLELGPKEGLALINGTQMVTALGAYTLERAHNIARQADVIAALSLDVLKGTTRA
15  SWALL:Q9HLI6     41.0%  MGEGKAF-FEGRLMDSARALEKAGLKPYQFKEKEBGVALINGTSFMSGILSIAVMDAHDILENAIRSALLSFEALGGTSKA
16  SWALL:HUTH_MOUSE 38.6%  IGEGKMWSPKSGWADAKYVLEAHGIKPIVLKPIVLKPIVIKPKEGLALINGTQMITSLGCEALERASAIARQADIVAALTLEVLKGTTKA
17  SWALL:BAB29407   38.6%  IGEGKMWSPKSGWADAKYVLEAHGIKPIVLKPIVIKPKEGLALINGTQMITSLGCEALERASAIARQADIVAALTLEVLKGTTKA
18  SWALL:HUTH_RAT   38.2%  IGEGKMWSPKSGWADAKYVLEAHGIKPIVLKPIVIKPKEGLALINGTQMITSLGCEAVERASAIARQADIVAALTLEVLKGTTKA
19  SWALL:AAG53586   39.8%  LGEGKAR-YRGEWLPAATALQKAGLAPVTLAAKEGLALINGTQASTAFALRGLFEAEDLFASAVVCGALTTEAVIGSRRP
20  SWALL:Q9KKE0     38.9%  IGHGSAMQGTERLSGADAL-ARLGLAPLRLEAKEGLSLVNGTPCATGLAALALARTERLFAWADAAAAMTYE-NLGSQAN
21  SWALL:Q9HQD5     42.2%  IGEGQA-DVAGERMPAAEALAAADLEPVTLQAKEGLALINGTQLTTGVAALALVDAERVLRSADTAGALTTEVTMSTTAS
```

Figure 14D

```
                         241                                                                                                                     320
                                                                    .                                .                                .
 983831           100.0%      FRAELHEPLRPHPGQGRSAQNMFAFLADSPIVASHREGDGRVQDAYSLRCSPQVTGAARDTIAHARLVATRELAAAIDNP
 1 SWALL:CAC21618  66.1%      LAPELHA-IRPHPGQAASAANMAAVLKGSGLTGHHQDDAPRVQDAYSVRCAPQVAGAGRDTMAHAGLVAERELAAAVDNP
 2 SWALL:HUTH_STRGR 65.4%     LAPELHA-IRPHPGQGVSADNMSRVLAGSGLTGHHQDDAPRVQDAYSVRCAPQVNGAGRDTLDHAALVAGRELASSVDNP
 3 SWALL:HUTH_DEIRA 46.8%     FQPDV-VGLRPHPGALAVAAELREFLAGSEIAPSHLTGDGKVQDAYSLRAVPQVHGATWDALAQAERVLAVEFASVTDNP
 4 SWALL:BAB16159   42.0%     FHPDIHT-LRGHKGQIDAGSALRNLLQGSEIRESHIEGDERVQDPYCIRCQPQVDGACLDLLASVARTLEIEANAVTDNP
 5 SWALL:Q9KWE4     42.0%     FHPDIHT-LRGHKGQIDAGSALRNLLQGSEIRESHIEGDERVQDPYCIRCQPQVDGACLDLLASVARTLEIEANAVTDNP
 6 SWALL:HUTH_BACSU 40.4%     FDEDIHLA-RGYQEQIDVAERIRFYLSDSGLTTS--QGELRVQDAYSLRCIPQVHGATWQTLGYVKEKLEIEMNAATDNP
 7 SWALL:Q9KSQ4     42.2%     FDPRIHR-VRGHKTQMDAATAYRHLLVSSEIGQSHSNCE-KVQDPYSLRCQPQVMGACLQQIRSAAEVLEVEANSVSDNP
 8 SWALL:Q9HU85     41.7%     FDARIHAA-RGQRGQIDVAAAYRDLLASSEVARSHEKCD-KVQDPYSLRCQPQVMGACLTQMRQAAEVLEIEANAVSDNP
 9 SWALL:Q9KBE6     39.3%     FDEQIHFA-RGYVEQVDVARRMESYLQDSQLTT--RQGELRVQDAYSLRCIPQVHGATWQTLRYVKEKLEIEMNAATDNP
10 SWALL:HUTH_PSEPU 41.7%     FDARIHEA-RGQRGQIDTAACFRDLLGDSSEVSSHKNCD-KVQDPYSLRCQPQVMGACLTQLRQAAEVLGIEANAVSDNP
11 SWALL:HUTH_RHIME 40.6%     FHPDIQHCAAIRARSTRAAA-LRQLLTGSPIRQSHIEGDERVQDPYCIRCQPQVDGACLDLLRSVAATLTIEANAVTDNP
12 SWALL:Q9HU90     40.7%     FDAEI-VALKPHPGMQRVAANLRALLAGSQVLENAR--GIRTQDALSIRSIPQIHGACRDQLAHARQIET-ELNSATDNP
13 SWALL:HUTH_HUMAN 39.2%     FDTDIHA-LRPHRGQIEVAFRFRSLLSDSEIAESHRFCD-RVQDAYTLRCCPQVHGVVNDTIAFVKNITTTELNSATDNP
14 SWALL:HUTH_CAEEL 38.8%     YDPDIHR-IRPHRGQNLSALRLRALLNPSQIAESHRNCT-KVQDAYTLRCVPQVHGVVHDTIEFVREIITTEMNSATDNP
15 SWALL:Q9HLI6     41.0%     FTPWILGA-RPHLGQVAIGNRFREYLTGSDIV--KRADSVKVQDAYTLRCIPQVYGSVADVIDYENVLSVEINSATDNP
16 SWALL:HUTH_MOUSE 38.6%     FDTDIHA-VRPHRGQIEVAFRFRSLLSDSEIAESHRFCD-RVQDAYTLRCCPQVHGVVNDTIAFVKDITTTELNSATDNP
17 SWALL:BAB29407   38.6%     FDTDIHA-VRPHRGQIEVAFRFRSLLSDSEIAESHRFCD-RVQDAYTLRCCPQVHGVVNDTIAFVKDITTTELNSATDNP
18 SWALL:HUTH_RAT   38.2%     FDTDIHA-VRPHRGQIEVAFRFRSLLSDSEIAESHRFCD-RVQDAYTLRCCPQVHGVVNDTIAFVKDITTTELNSATDNP
19 SWALL:AAG53586   39.8%     FDARIHE-VRGQRGQIDAAALFRHVLTDTSAIASHHNCD-KVQDPYSLRAVPQVMGACLTQMRQVAEVLLVESNAVSDNP
20 SWALL:Q9KKE0     38.9%     AFAELPLALRQSPGLSAVGEGLRDWLADSPMLAG--TAGTRTQDPLSLRAVPQVHGAARDAFGQVAEIVDRELASVTDNP
21 SWALL:Q9HQD5     42.2%     CAPAIHE-VRPHDGQAVSARHIRNLTAGSEVLDHHRDCD-RVQDAYSIRCLPQVHGAVRDALDHLRAAVATELNSATDNP
```

Figure 14E

```
                          321                                                                                                   400
     983831          100.0%  VVLPSGEVTSNGNFHGAPVAYVLDFLATAVADLGSIAERRTDRMLDPARSRDLPAFLADDPGVDSGMMIAQYTQAGLVAE
 1  SWALL:CAC21618    66.1%  VVLPDGRVESNGNFHGAPVAYVLDFLAVAVADLGSIAERRTDRLLDKNRSHGLPPFLADDAGVDSGLMIAQYTQAALVGE
 2  SWALL:HUTH_STRGR  65.4%  VVLPDGRVESNGNFHGAPVAYVLDFLAIVADLGSICERRTDRLLDKNRSHGLPPFLADDAGVDSGLMIAQYTQAALVSE
 3  SWALL:HUTH_DEIRA  46.8%  LIFPTGEVVSGGNFHGQPLAVTIDALKVAVAELGSISERRTEQLLNPALS-GLPAFLTPNGGLNSGFMIAQYTSAALVSE
 4  SWALL:BAB16159    42.0%  LVLSDNSVVSGGNFHAEPVAFAADQTALAVCEIGAIAQRRIALLVDPALSYGLPAFLSKKPGLNSGLMIAEVTSAALMSE
 5  SWALL:Q9KWE4      42.0%  LVLSDNSVVSGGNFHAEPVAFAADQTALAVCEIGAIAQRRIALLVDPALSYGLPAFLSKKPGLNSGLMIAEVTSAALMSE
 6  SWALL:HUTH_BACSU  40.4%  LIFNDGDVISGGNFHGQPIAFAMDFLKIAISELANIAERRIERLVNPQLN-DLPPFLSPHPGLQSGAMIMQYAAASLVSE
 7  SWALL:Q9KSQ4      42.2%  LVFADGDIISGGNFHAEPVAMAADNLALAIAEIGSLSERRMALLIDSALSK-LPPFLVDNGGVNSGFMIAQVTAAALASE
 8  SWALL:Q9HU85      41.7%  LVFAAGDVISGGNFHAEPVAMAADNLALALAEIGSLSERRISLMMDMHMSQ-LPPFLVANGGVNSGFMIAQVTAAALASD
 9  SWALL:Q9KBE6      39.3%  LIFDNGQVISGGNFHGQQIALAMDFLGIAMAELANISERRIERLVNPQLN-DLPPFLSAAPGVQSGVMILQYCAASLVSE
10  SWALL:HUTH_PSEPU  41.7%  LVFAAGDVISGGNFHAEPVAMAADNLALALAEIGSLSERRISLMMDKHMSQ-LPPFLVENGGVNSGFMIAQVTAAALASE
11  SWALL:HUTH_RHIME  40.6%  LVLSDNSVVSGGNFHAEPVAFAADQIALAVCEIGAISQRRIALLVDPALSLRLPAFLAKKPGLNSGLMIAEVTSAALMSE
12  SWALL:Q9HU90      40.7%  LLLGTPEVVSQANPHGESVAMAADLLAIAVAELGVAERRLDRLVNPLVS-GLPAFLVGKPGVNSGMMITQYVAASLAGE
13  SWALL:HUTH_HUMAN  39.2%  MVFANGETVSGGNFHGEYPAKALDYPAKALDYLAIGIHELAAISERRIERLCNPSLS-ELPAFLVAEGGLNSGFMIAHCTAAALVSE
14  SWALL:HUTH_CAEEL  38.8%  LVFADREIISGGNFHGEYPAKALDFLAIAVAELAQMSERRLERLVNKELS-GLPTFLTPDGGLNSGFMTVQLCAASLVSE
15  SWALL:Q9HLI6      41.0%  L-FNGEEVSGGNFHGEPVALAADFLAIALTDLGNMVERRIARLVDTNLS-GLPPFLTPDSGLNSGYMIPQYTAAALCNR
16  SWALL:HUTH_MOUSE  38.6%  MVFASGETISGGNFHGEYPAKALDYLAIGVHELAAISERRIERLCNPSLS-ELPAFLVAEGGLNSGFMIAHCTAAALVSE
17  SWALL:BAB29407    38.6%  MVFASGETISGGNFHGEYPAKALDYLAIGVHELAAISERRIERLCNPSIS-ELPAFLVAEGGLNSGFMIAHCTAAALVSE
18  SWALL:HUTH_RAT    38.2%  MVFASGETISGGNFHGEYPAKALDYLAIGVHELAAISERRIERLCNPSLS-ELPAFLVAEGGLNSGFMIAHCTAAALVSE
19  SWALL:AAG53586    39.8%  LVFAANEMVFRGNFHAEPVAMAADNLALAIAEIGALSERRIALMMDKHMSQ-LPPFLVRNGGVNSGFMIAQVTAAALASE
20  SWALL:Q9KKE0      38.9%  AVAGSPEVHSQAHAVGAALGLAMDSLAVAVAEVAAISERRIDRLVNPLVS-GLPAFLAGDSGVSSGFMIAQYTAAALVAE
21  SWALL:Q9HQD5      42.2%  LVFPSGTVVSGGNFHGEVLALRLGYAASALAELAAISERRTDRLLNPETQEPLEPFLAPDSGLHSGLMIPQYTAASLVND
```

Figure 14F

```
                              401                                                                                                    480
   983831              100.0%    NKRLAVPASVDSIPSSAMQEDHVSLGWHAARKLRTSVANLRRILAVEMLIAGRALDLRAPLKPGPATGAVLEVLRSKVAG
 1 SWALL:CAC21618       66.1%   LKRLAVPASADSIPSSAMQEDHVSMGWSAARKLRTAVDNLARVIAVELYAATRAIQLREGLTPAPASQAVVEAVRAAVEG
 2 SWALL:HUTH_STRGR     65.4%   MKRLAVPASADSIPSSAMQEDHVSMGWSAARKLRTAVDNLARIVAVELYAATRAIELRAALTPAPASEAVVAALRAAGAG
 3 SWALL:HUTH_DEIRA     46.8%   NKVLSHPASVDSIPTSANQEDHVSMGAHAARQLRQIVANVQTVLSIELLCAAQGLDFQQ-LRAGRGVQAAYEYVRTFVPT
 4 SWALL:BAB16159       42.0%   NKQMSHPASVDSTPTSANQEDHVSMACHGARRLLAMTDNLFGILGIEALAAVQGVELRGPLKTSPELEKAAAVLRSAVPV
 5 SWALL:Q9KWE4         42.0%   NKQMSHPASVDSTPTSANQEDHVSMACHGARRLLAMTDNLFGILGIEALAAVQGVELRGPLKTSPELEKAAAVLRSAVPV
 6 SWALL:HUTH_BACSU     40.4%   NKTLAHPASVDSIPSSANQEDHVSMGTIAARHAYQVIANTRRVIAIEAICALQAVEYRGIEHAASYTKQLFQEMRKVVPS
 7 SWALL:Q9KSQ4         42.2%   NKTLAHPASVDSLPTSANQEDHVSMATFAARRLRDMGENTRGILAVEYLAAAQGLDFRAPLKSSPRIEEARQILREKVPF
 8 SWALL:Q9HU85         41.7%   NKALAHPASVDSLPTSANQEDHVSMAPNAGKRLWAMAENVRGILAVEWLGACQGLDFREGLKSSPKLEQARRLLRDKVPY
 9 SWALL:Q9KBE6         39.3%   NKTLAHPASVDSIPSSANQEDHVSMGTIGSRHAYQIIQNVRNVLAIELICAMQAVDIRGREKMASFTKKILEKGREHVPY
10 SWALL:HUTH_PSEPU     41.7%   NKALSHPHSVDSLPTSANQEDHVSMAPAAGKRLWEMAENTRGVLAIEWLGACQGLDLRKGLKTSAKLEKARQALRSEVAH
11 SWALL:HUTH_RHIME     40.6%   NKALSHPASVDSTPTSANQEDHVSMACHGARRLLQMTENLFSIIGIEALAAVQGIEFRAPLTTSPELQKAAAAVRGVSSS
12 SWALL:Q9HU90         40.7%   NRQLAQPAVVDNFVTSALQEDHLSLGTSAALKLGRALENLRRILAIEYLLAAQAFEFLAPQRFGQGTAAAWGILRERVPA
13 SWALL:HUTH_HUMAN     39.2%   NKALCHPSSVDSLSTSAATEDHVSMGGWAARKALRVIEHVEQVLAIELLAACQGIEFLRPLKTTTPLEKVYDLVRSVVRP
14 SWALL:HUTH_CAEEL     38.8%   NKVLCHPSSVDSIPTSCNQEDHVSMGGFAARKALTVVEHVEAVLAMELLAACQGIEFLKPLISTAPLHKIYQLVRS-VAP
15 SWALL:Q9HLI6         41.0%   NKVLAYPSSADTIPTSANQEDHVSMGATGSLKLLEIIDNVRYIIAIEYLLGSQALEFTDK-GMSPSTRKIYEKIREKVEK
16 SWALL:HUTH_MOUSE     38.6%   SKALCHPSSVDSLSTSAATEDHVSMGGWAARKALRVVEHVEQVLAIELLAACQGIEFLRPLKTTTPLEKVYDLVRSVVRP
17 SWALL:BAB29407       38.6%   SKALCHPSSVDSLSTSAATEDHVSMGGWAARKALRVVEHVEQVLAIELLAACQGIEFLRPLKTTTPLEKVYDLVRSVVRP
18 SWALL:HUTH_RAT       38.2%   SKALCHPSSVDSLSTSAATEDHVSMGGWAARKALRVIEHVEQVLAIELLAACQGIEFLRPLKTTTPLEKVYDLVRSVVRP
19 SWALL:AAG53586       39.8%   NKGLCHPTSVDK-PPSANQEDHVSMAPAAGRRLWEMAGNTRGVLAVEWLAACQGADLRDGLTSSPLLEQARQSCGEQVAH
20 SWALL:Q9KKE0         38.9%   NRRLAAPASLDGGITSALQEDMLTHATPAAWKALSIVDNLERILAIELLAAHRPMSCSRKRARRNAPLPFTGTYARRSP
21 SWALL:Q9HQD5         42.2%   LRSLGQP-TLDNASVSGAQEDHVSMSAGAAYNFREAVEKAATVVGVELLCGAQGREFLDPLALGAGTAAAYDLVR-EVSE
```

Figure 14G

```
                           481                                                          513
   983831               100.0%   [ PGQDRFLSAELEAAYDLLANGSVHKALEAHLPA          ]
 1 SWALL:CAC21618        66.1%     PGPDRHLAPDLAAADAFVRAGHLVAAAESVTGP
 2 SWALL:HUTH_STRGR      65.4%     PGPDRFLAPDLAAADTFVREGRLVAAVEPVTGP
 3 SWALL:HUTH_DEIRA      46.8%     LTEDRYFRPDLLRLRGELVSGRVAQAADTQAPA
 4 SWALL:BAB16159        42.0%     LEDDRYMATDLKAAIEVVASGALVSAISSGLPV
 5 SWALL:Q9KWE4          42.0%     LEDDRYMATDLKAAIEVVASGALVSAISSGLPV
 6 SWALL:HUTH_BACSU      40.4%     IQQDRVFSYDIERLTDWLKKESLIPDHQNKELR
 7 SWALL:Q9KSQ4          42.2%     YDKDRYFAPDIEKANALL-QLAVHNRLMPDQLL
 8 SWALL:Q9HU85          41.7%     YQEDRFFAPDIEAASQLLASGCLNALLPARLLP
 9 SWALL:Q9KBE6          39.3%     IDQDRMFAKDIERAAKWLKDGSWDFTKMREKER
10 SWALL:HUTH_PSEPU      41.7%     YDRDRFFAPDIEKAVELLAKGSLTGLLPAGLPS
11 SWALL:HUTH_RHIME      40.6%     IEEDRFMADDLKAAGDLVASGRLAAAVSAGLPK
12 SWALL:Q9HU90          40.7%     YDTDRWLAPDIASAAAILGERKSLARLAASIGD
13 SWALL:HUTH_HUMAN      39.2%     WIKDRFMAPDIEAAHRLLLEQKVWEVAAPYIEK
14 SWALL:HUTH_CAEEL      38.8%     PNEDRYMKPEIDAVLEMIRENRIWEAVLPHLET
15 SWALL:Q9HLI6          41.0%     LDHDRPPSFDIETIRKMDKKEFISALP------
16 SWALL:HUTH_MOUSE      38.6%     WIKDRFMAPDIEAAHRLLLDQKVWEVAAPYIEK
17 SWALL:BAB29407        38.6%     WIKDRFMAPDIEAAHRLLLDQKVWEVAAPYIEK
18 SWALL:HUTH_RAT        38.2%     WIKDRFMAPDIEAAHRLLLDQKVWEVAAPYIEK
19 SWALL:AAG53586        39.8%     YDDDRFFAPDIEAAISLLNKGSLVGLLPAFL--
20 SWALL:Q9KKE0          38.9%     PIATIVR--------------------------
21 SWALL:Q9HQD5          42.2%     PAGDRALADDMAAVGDLVRAGLVEDAVARALDA
```

Figure 14H

KEY:

```
983831     : HAL
 1 CAC21618    : Streptomyces coelicolor
 2 HUTH_STRGR  : Streptomyces griseus
 3 HUTH_DEIRA  : Deinococcus radiodurans
 4 BAB16159    : Agrobacterium rhizogenes
 5 Q9KWE4      : Agrobacterium rhizogenes
 6 HUTH_BACSU  : Bacillus subtilis
 7 Q9KSQ4      : Vibrio cholerae
 8 Q9HU85      : Pseudomonas aeruginosa
 9 Q9KBE6      : Bacillus halodurans
10 HUTH_PSEPU  : Pseudomonas putida
11 HUTH_RHIME  : Rhizobium meliloti
12 Q9HU90      : Pseudomonas aeruginosa
13 HUTH_HUMAN  : Human
14 HUTH_CAEEL  : Caenorhabditis elegans
15 Q9HLI6      : Thermoplasma acidophilum
16 HUTH_MOUSE  : Mouse
17 BAB29407    : Mus musculus (Mouse)
18 HUTH_RAT    : Rat
18 AAG53586    : uncultured bacterium pCosAS1
20 Q9KKE0      : Rhizobium meliloti
21 Q9HQD5      : Halobacterium sp
```

Figure 15A

```
STRG    6   VVVGTSGTTAEDVVAVARHGARVELSAAAVEALAAARLIVDALAAKPEPVYGVSTGFGAL
"HAL"   7   ITLGISGATADDVIAVARHEARISISPQVLEELASVRAHIDALASADTPVYGISTGFGAL
            * ** ** * ****** **        *  **  *    ****    ****  ******

STRG,   66  ASRHIGTELRAQLQRNIVRSHAAGMGPRVEREVVRALMFLRLKTVASGHTGVRPEVAQTM
HAL     67  ATRHIAPEDRAKLQRSLIRSHAAGMGEPVEREVVRALMFLRAKTLASGRTGVRPVVLETM
            * ***    *  *  * ********* ************ ** ***  *****  * **

STRG    126 ADVLNAGITPVVHEYGSLGCSGDLAPLSHCALTLMGEGEAEGPDGTVRPAGELLAAHGIA
HAL     127 VGMLNAGITPVVREYGSLGCSGDLAPLSHCALVLMGEGEATDAHGDIRPVPELFAEAGLT
              ********* *******************  ******   *  * **  **    *

STRG    186 PVELREKEGLALLNGTDGMLGMLVMALADLRNLYTSADITAALSLEALLGTDKVLAPELH
HAL     187 PVELAEKEGLALVNGTDGMIGQLIMALADLDELLDIADATAAMSVEAQLGTDQVFRAELH
            **** ******* ****** * * ***** *    * * *** * ** **** *  ***

STRG    246 A-IRPHPGQGVSADNMSRVLAGSGLTGHHQDDAPRVQDAYSVRCAPQVNGAGRDTLDHAA
HAL     247 EPLRPHPGQGRSAQNMFAFLADSPIVASHREGDGRVQDAYSLRCSPQVTGAARDTIAHAR
              ********  * **    * *  * *    * ******* ** *** ** ***  **

STRG    305 LVAGRELASSVDNPVVLPDGRVESNGNFHGAPVAYVLDFLAIVAADLGSICERRTDRLLD
HAL     307 LVATRELAAAIDNPVVLPSGEVTSNGNFHGAPVAYVLDFLAIAVADLGSIAERRTDRMLD
            *** ****   ******* *   ****************** ******  ******  *
```

Figure 15B

```
STRG  365  KNRSHGLPPFLADDAGVDSGLMIAQYTQAALVSEMKRLAVPASADSIPSSAMQEDHVSMG
HAL   367  PARSRDLPAFLADDPGVDSGMMIAQYTQAGLVAENKRLAVPASVDSIPSSAMQEDHVSLG
             *  **  *****  *******  ****  *********  ****************  *

STRG  425  WSAARKLRTAVDNLARIVAVELYAATRAIELRAAEGLTPAPASEAVVAALRAAGAEGPGP
HAL   427  WHAARKLRTSVANLRRILAVEMLIAGRALDLRAP--LKPGPATGAVLEVLRSKVA-GPGQ
           * ******* * *** * *** *   **  * *    *  *  ** *  *   * ***

STRG  485  DRFLAPDLAAADTFVREGRLVAAVE
HAL   484  DRFLSAELEAAYDLLANGSVHKALE
           ****  **  *  *     *  * *
```

CLONING, OVEREXPRESSION AND THERAPEUTIC USE OF BIOACTIVE HISTIDINE AMMONIA LYASE

This Application claims the benefit of provisional application 60/197,770, filed Apr. 14, 2000 now abandoned.

FIELD OF THE INVENTION

The present invention relates generally to bioactive, amino acid-degrading enzymes, more specifically to a histidine ammonia lyase derived from a bacterium belonging to the family Corynebacteriaceae, and to conservative variants thereto. Also described is the use of histidine ammonia lyase, singly or combined with L-histidinol, for treating various viral diseases.

BACKGROUND OF THE INVENTION

Histidine ammonia lyase (EC 4.3.1.3) catalyzes the conversion of L-histidine to urocanic acid and ammonia. This is the first step in the degradation of histidine in both mammals and bacteria. A deficiency in this enzyme results in histidinemia, which is characterized by high serum histidine levels.

An isolated histidine ammonia lyase enzyme is one agent for treating increased histidine levels. Several lines of evidence indicate that in vivo depletion of serum histidine concentrations by histidine ammonia lyase could have additional therapeutic value. For example, histidine ammonia lyases have been shown in in vivo animal models to have potential therapeutic value against certain tumors. Roberts et al., *Cancer Treat. Rep.* 63:1045 (1979); Jack et al., *Leukemia Res.* 7:421 (1983).

Therapeutically useful (bioactive) enzymes generally display characteristics that are predictors of usefulness in vivo. These factors are outlined in Holcenberg and Roberts et al., *Ann. Rev. Pharmacol. Toxicol.* 17: 97 (1977), and include high activity at physiological pH and no requirement for exogenous cofactors. The histidine ammonia lyase isolated from a bacterium of the family Corynebacteriaceae, herein denoted as "HAL," has been partially characterized by Roberts et al., *Cancer Treat. Rep.* 63: 1045 (1979). HAL demonstrates a broad useful pH range with approximately 75% of activity being retained at pH 7.2. The plasma half-life of HAL in mice is eight hours. The usefulness of this enzyme for histidine depletion in vivo is evident from the observation that single intraperitonial injections of 400 IU/kg effectively depleted plasma histidine in mice for up to 24 hours. However, the Corynebacteriaceae HAL which Roberts et al. described was not in purified form. As a result, many of the therapeutically beneficial properties associated with this HAL were unknown.

Histidine ammonia lyases have been isolated from several bacterial, animal, mammalian and plant sources. Shibatani et al., *Eur. J. Biochem.* 55: 263–269 (1975). Km values of these enzymes range between 1 and 20 mM. Shibatani (1975), supra; Wu et al., *Gene.* 115: 19–25 (1992); Jack et al., *Leukemia Research*, 7: 421–429 (1983); Khanna and Chang, *Int'l J. Artificial Organs* 13: 189–195 (1990). Genes coding for histidine ammonia lyases have been cloned from a number of organisms (Consevage, M. W. and A. T. Phillips. 1990. *Journal of Bacteriology.* 172 (5): 2224–2229; Oda, M. Sugishita, A. and K. Furukawa. 1988. *J. Bacteriology.* 170(7): 3199–3205; Wu, P. C., Kroening, T. A., White, P. J. and Kendrick, K. E. 1992. *J. Bacteriology.* 174(5): 1647–1655; Taylor, R. G., Lambert, M. A., Sexsmith, E., Sadler, S. J., Ray, P. N., Mahuran, D. J. and McInnes, R. R. 1990. *J. Biol. Chem.* 265(30): 18192–18199). Biochemical characterization has shown that most histidine ammonia lyases are inhibited by EDTA and thiol reagents (Shibatani, T., Kakimoto, T. and I. Chibata. 1975. *Eur. J. Biochem.* 55: 263–269; Okamura, H., Nishida, T. and H. Nakajawa. 1974. *J. Biochem.* 75: 139–152). A bioactive histidine ammonia lyase from a bacterium identified as *Kurthia* species was described by Jack, et al. in 1983 (Jack, G. W., Wiblin, C. N. and P. C. McMahon. 1983. *Leukemia Research*, 7(3): 421–429.) The *Kurthia* species histidine ammonia lyase was reported to have a $K_m$ of 1.25 mM with a half-life of 6–7 hours in mice. Chemical modification of the *Kurthia* histidine ammonia lyase did not increase the biological half-life of this enzyme. However, while HAL isolated from Corynebacteriaceae was effective in reducing ascites tumors in mice with high cell challenge ($10^7$ cells per mouse), the histidine ammonia lyase isolated from *Kurthia* was reported to be effective only at low tumor cell challenge levels ($10^3$ to $10^5$ cells per mouse).

L-histidinol is an analog of histidine that is capable of altering histidine metabolism. Alteration of histidine metabolism by L-histidinol has provided therapeutic benefit. Histidine is required for several cellular processes, including protein synthesis and formation of histamine, both of which are required for tumor growth (Watanabe, et al, 1982. *Biochem. and Biophys. Res. Comm.* 109:478–485; Bartholeyns and Bouclier. 1982. *Cancer Res.* 44:639–645; Hakii, et al, 1986. *J. Cancer Res. and Clin. Oncol.* 111:177–181). Histidine is a direct precursor of histamine and is converted to histamine by the enzyme histidine decarboxylase (HDC). L-histidinol interferes with this conversion by inhibiting HDC. Therefore, L-histidinol can act therapeutically by inhibiting HDC, which is induced by strong tumor promoting phorbol esters (Mitra, et al, 1993. *J. Cellular Physiol.*, 156:348–357). L-histidinol possesses some anti-tumor activity, as well as an ability to reverse resistance of certain tumor cell lines to some antineoplastic compounds (Stolfi, R. L. and Martin, D. S. 1990. *Chemotherapy*, 36 (6): 435–440; Warrington, R. C., Fang W. D. and L. U. Zhang, 1996. *Anticancer Research* 16 (6B): 3641–3646; Warrington, R. C. and Fang W. D. 1989. *Journal of the National Cancer Institute.* 81 (10): 798–803). L-histidinol is also able to enhance the efficacy of certain anti-cancer drugs, when both are administered to a patient simultaneously. (Warrington, R. C. and W. D. Fang. 1991. *Anticancer Research*, 11 (5): 1869–1874; Warrington, R. C., Cheng, I. And W. D. Fang. 1994. *Anticancer Research*, 14 (2A): 367–372; Warrington, R. C., Cheng, I., Zhang, L. and W. D. Fang. 1993. *Anticancer Research*, 13 (6A): 2107–2112; Warrington, R. C. 1992. *Biochemistry and Cell Biology*, 70 (5): 365–375; Zaharko, D., Plowman, J., Waud, W., Dykes, D. and L. Malspeis. 1992. *Cancer Research*, 52 (13): 3604–3609). For example, the therapeutic index of chemotherapeutic agents is increased by combining treatment with L-histidinol, since L-histidinol reduces the toxicity of normal chemotherapeutic agents to normal cells but not to cancer cells (Warrington, R. C., Fang, W. D., Zhang, L. Shieh, M. and M. H. Saier, Jr. 1996. *Anticancer Research*, 16 (6B): 3635–3639; Warrington, R. C., Fang W. D., Zhang, L., Shieh, M. and M. H. Saier, Jr. 1996. *Anticancer Research*, 16 (6B): 3629–3633; Badary, O. A., Nagi, M. N., Al-Sawaf, H. A, Al-Harbi, M., and A. M. Al-Bekairia. 1997. *Nephron*, 77 (4): 435–439; Al-Shabanah, O. A., Badary, O. A., Al-Gharably, N. M. and H. A. Al-Sawaf. 1998. *Pharmacological Research*, 38 (3): 225–230; Badary, O. A. 1999. *Experimental Nephrology*, 7 (4): 323–327).

In theory, the use of L-histidinol with a histidine ammonia lyase offers a therapeutic approach to depleting serum histamine and lowering histidine levels. L-histidinol has limited usefulness as a single agent due to its low half-life (Zaharko, D., Plowman, J., Ward, W., Dykes, D., and L. Malspeis, 1992. *Cancer Research*. 52: 3604–3609) and its mode of action as a competitive inhibitor. Accordingly, L-histidinol must be present in very high concentrations in order to competitively inhibit cellular processes involving histidine. Reduced histidine levels would enhance the effectiveness of L-histidinol, by allowing cells to uptake the L-histidinol more readily.

Nevertheless, a histidine ammonia lyase suitable for combination therapy with a histidine analog, such as L-histidinol, must have the additional property of not being inhibited by L-histidinol. One prevalent characteristic of all known isolated histidine ammonia lyases is their inhibition in the presence of a histidine analog, like histidinol. For example, histidine ammonia lyases isolated from bacteria such as *Achromobacter liquidum* and *Streptomyces griseus* are inhibited by L-histidinol and L-histidinol phosphate, respectively, with a $K_i$ of 4.58 and 0.27 mM, respectively (Shibatani, T. et al. 1975. *Eur. J. Biochem*. 55: 263–269; Wu, P. C. et al. 1995. *Gene*. 115(1–2): 19–25).

Due to their enzymatic inhibition by histidinol, previously described histidine ammonia lyases have not been suitable candidates for use in combination therapies with these histidine analogs for treating pathologies such as cancer. Accordingly, there is a present and unmet need for a histidine ammonia lyase that possesses the relevant properties associated with previously isolated histidine ammonia lyases, yet maintains the ability to deplete histidine in the presence of L-histidinol.

In addition to cancer, viral diseases such as Human Respiratory Syncytial Virus (RSV), Herpes Simplex Virus (HSV) and Human Immunodeficiency Virus (HIV), infect millions worldwide and cause major health problems. RSV, a common cause of winter outbreaks of acute respiratory disease, in 1998 resulted in 90,000 hospitalizations and 4,500 deaths and is the largest cause of lower respiratory tract disease among infants and young children in the United States (CDC. 1997. *MMWR*. 46(49); 1163–1165). Herpes Simplex Virus infects an even larger portion of the population. The Centers for Disease Control estimated that in 1998, 45 million people ages 12 and older, or one out of five of total adolescent and adult population, was infected with the Herpes Simplex Virus. The Joint United Nation Programme on HIV/AIDS (UNAIDS) estimates that worldwide 33.6 million persons are infected with HIV/AIDS and 2.6 million people died in 1999 from this disease.

Human infectious viruses vary widely in the way they enter cells, replicate inside the cells, and subsequently get released from infected cells. RNA viruses have single- or double-stranded RNA as their genomes, which are naked or enveloped. The RNA strand can be either in a positive or negative form. RNA viruses enter the cell, make copies of their RNA genome, and direct the synthesis of messenger RNA to code for structural and regulatory proteins. Finally, the genome is assembled with structural proteins and the virus is released. DNA viruses have single- or double-stranded DNA genomes that can be either non-enveloped or enveloped. Retroviruses are also RNA viruses but they involve DNA in their replication process. Thus, each virus is unique in its infection and multiplication process.

One common theme in viral replication is the ability of a virus to utilize the human cellular machinery for its multiplication. This makes drug development against viruses very difficult. In the past, antiviral therapy has focused on development of appropriate vaccines or inhibiting unique processes in viral replication. This often renders such therapy very specific for a type or subtype of viruses. Currently, vaccines are the main line of defense against viruses. Vaccines are developed specifically for each virus type and subtype, and are useful only against that particular virus type/subtype.

Therapies also have been developed that take advantage of unique processes in viral replication. For example, reverse transcriptase is unique to retroviruses. Nucleotide analogs and non-nucleotide reverse transcriptase inhibitors have been developed that inhibit reverse transcriptase without affecting other polymerases. However, such therapy is limited to combating only retroviruses. Yet another approach that targets a unique viral replication process is the use of protease inhibitors against HIV. But since these inhibitors target a specific enzyme, HIV protease, they cannot be effective against a wide range of viruses. Yet another example of a virus-specific therapy is the use of the antiviral compound ganciclovir, which is effective against Herpes Simplex Virus. Ganciclovir is specifically cytotoxic to herpes infected cells. Although ganciclovir therapy may be beneficial to combating the Herpes Simplex Virus, it has limited or no application for treating other viruses.

Accordingly, there is a great need for a therapeutic agent that can be effective against a broad spectrum of viruses. There has been no indication heretofore that a peptide having a histidine ammonia lyase activity could effectively treat infectious viral agents. Thus, a substantial therapeutic and market potential exists for a histidine ammonia lyase that is effective against infectious viral agents.

SUMMARY OF THE INVENTION

Accordingly, it is an object of the invention to provide a purified polypeptide having a histidine ammonia lyase activity that is not substantially inhibited by a histidine analog, such as histidinol.

It is a further object of the invention to provide a method for treating cancer, using a histidine analog, such as histidinol and a purified polypeptide having a histidine ammonia lyase activity that is not substantially inhibited by such compounds.

It is still a further object of the invention to provide a method for treating a viral Infection, using a purified polypeptide having a histidine ammonia lyase activity.

These and other objects of the invention will become apparent to one of ordinary skill in the art upon reading the present application.

In one aspect, the invention provides an isolated polypeptide having histidine ammonia lyase activity, wherein the histidine ammonia lyase activity is not substantially decreased in the presence of a histidine analog such as histidinol. The invention also provides a polypeptide having the preceding characteristics, which comprises a peptide sequence selected from the group consisting of SEQ ID NO: 1, SEQ ID NO: 2, SEQ ID NO: 3, SEQ ID NO: 4, SEQ ID NO: 5, and SEQ ID NO: 6. The invention also provides a polypeptide having the preceding characteristics, which comprises a peptide sequence selected from the group consisting of SEQ ID NO: 8, SEQ ID NO: 9, SEQ ID NO: 10, and SEQ ID NO: 11. The invention further provides a method for PEGylating an isolated polypeptide having the preceding characteristics, comprising reacting a PEG with the polypeptide.

In a methodological aspect, the invention provides a method for treating a patient suffering from a viral disorder, comprising administering to a patient suffering from a viral infection a therapeutic amount of a polypeptide having histidine ammonia lyase activity.

The invention further provides a method for treating a patient suffering from a cancer, comprising administering to the patient suffering from the cancer 1) a therapeutic amount of an isolated polypeptide having histidine ammonia lyase activity, wherein said histidine ammonia lyase activity is not substantially decreased in the presence of a histidine analog such as histidinol and 2) a therapeutic amount of a histidine analog.

In a further methodological approach, the invention provides a method for treating disease, comprising administering to a patient 1) a therapeutically effective amount of a polypeptide having histidine ammonia lyase activity and 2) administering to the patient a therapeutically effective amount of a chemotherapeutic agent or a retroviral vector. Consistent with this methodology, the invention provides a method for treating disease according to the previous method, wherein upon the administration of the polypeptide, non-diseased cells of the patient enter a reversible quiescent state.

The invention also provides a method for delivering an immunosuppressant to a patient, comprising: 1) administering to a patient a therapeutically effective amount of a polypeptide having histidine ammonia lyase activity, wherein the polypeptide generates trans-urocanic acid (t-UA) in vivo; and 2) subjecting the patient to an irradiating agent, wherein the irradiating agent causes the photoisomerization of t-UA to its cis isomer (c-UA), and wherein said cis isomer comprises an immunosuppressive property.

The present invention also includes an isolated DNA sequence comprising SEQ ID NO: 7, as well as an expression vector comprising SEQ ID NO: 7. In addition, the invention provides a method for treating a patient comprising constructing an expression vector comprising SEQ ID NO: 7 and introducing the expression vector into the patient.

The present invention further includes an isolated DNA sequence comprising SEQ ID NO: 12, as well as an expression vector comprising SEQ ID NO: 12. In addition, the invention provides a method for treating a patient comprising constructing an expression vector comprising SEQ ID NO: 12 and introducing the expression vector into the patient.

BRIEF DESCRIPTION OF THE DRAWINGS

FIG. 1 shows the restriction pattern of the HAL coding region cut with selected enzymes.

FIG. 2 lists the experimentally derived peptide sequences of HAL (portion of SEQ ID NO: 3—n-terminal— and SEQ ID NOS 32–33—internal).

FIG. 3 depicts the SphI digestion pattern of HAL gene showing oligonucleotide and subclones.

FIG. 4 depicts a histidine ammonia lyase overexpressing plasmid.

FIG. 5 is an SDS-PAGE illustration, showing expression of HAL in E. coli. 30 μg samples were loaded onto a 10% SDS-PAGE gel. Lane 1: Sample taken at 1 hour following induction. Lane 2: Sample taken at 2 hours following induction. Lane 3: Sample taken at 3 hours following induction. Lane 4: Sample taken at 4 hour following induction.

FIG. 6 is a picture of the SDS-PAGE showing purification of HAL from E. coli. Lanes 1 and 4 contain 10 and 20 μg respectively of crude extract. Lanes 2 and 5 contain 5 and 10 μg respectively of phenyl sepharose pooled fractions. Lanes 3 and 6 contain 5 and 10 μg respectively of Q-sepharose pooled fractions.

FIG. 7 is a graph depicting the effect of temperature on HAL.

FIG. 8 is a graph depicting the effect of pH on HAL.

FIG. 9 is a chart illustrating the effect of HAL and Histidinol on HSV. Lane 1: Control. Lane 2: HAL alone (0.003 U/ml) Lane 3: L-histidinol alone (0.5 mM). Lane 4: HAL and L-histidinol (0.003 U/ml and 0.5 mM respectively).

FIG. 10 depicts the effectiveness of L-histidinol as a single agent. Lane 1: Control. Lane 2: L-histidinol (0.1 mM). Lane 3: L-histidinol (0.5 mM). Lane 4: L-histidinol (1.0 mM). Lane 5: L-histidinol (1.5 mM). Lane 6: L-histidinol 3.0 mM).

FIG. 11 depicts the effect of HAL and Histidinol on RSV. Lane 1: Control. Lane 2: HAL alone (0.005 U/ml). Lane 3: L-histidinol alone (3.0 mM). Lane 4: HAL and L-histidinol (0.005 U/ml and 3.0 mM respectively).

FIG. 12 depicts the effect of HAL on RMuLV. Lane 1: Control. Lane 2: HAL (0.001 U/ml). Lane 3: HAL (0.002 U/ml). Lane 4: HAL (0.004 U/ml).

FIG. 13 (SEQ ID NOS 34–42, respectively, in order of appearance) illustrates a first peptide sequence pileup of HAL from various bacteria, including Corynebacteriaceae, B. subtilis, S. griseus, P. putida.

FIG. 14 (SEQ ID NOS 43–64, respectively, in order of appearance) is a second peptide sequence pileup of HAL from various bacteria, including Corynebacteriaceae, S. griseus, and D. radiodurans.

FIG. 15 (SEQ ID NOS 65–66, respectively, in order of appearance) is a comparison between the amino acid sequence of S. griseus ("STRG") and Corynebacteriaceae ("HAL"); positions of an amino acid identity are delineated by "*".

DETAILED DESCRIPTION OF THE PREFERRED EMBODIMENTS

The present inventors have discovered that certain polypeptides, known as histidase or histidine ammonia lyases, can decrease serum histidine levels and induce accumulation of urocanic acid, and yet are not inhibited by analogs of histidine, such as histidinol. By virtue of this discovery, a bioactive histidine ammonia lyase according to the invention can be used to treat allergic reactions and pathologies characterized by increased levels of or need for histidine and/or histamine, such as cancer and infectious viruses.

The Inventive Polypeptides and Nucleic Acids

In one of its aspects, the present invention provides a polypeptide, commonly known as "histidase" or "histidine ammonia lyase," that depletes L-histidine serum levels, in turn producing urocanic acid—a beneficial by-product of histidine breakdown. A histidine ammonia lyase (EC 4.3.1.3) catalyzes the nonoxidative elimination of the alpha-amino group of histidine. Although L-histidinol is able to alter histidine metabolism, alteration of histidine metabolism via depletion of histidine with a histidine ammonia lyase would provide similar therapeutic benefits, yet would do so in an even more effective and potentially less toxic manner than L-histidinol. An additional advantage for treatment with histidine ammonia lyase is that one of the products of its action, urocanic acid, promises to have protective and beneficial effects on the immune system, as reported by Noonan et al., *Immunol. Today* 13: 250–254 (1992).

In another aspect, the invention contemplates a polypeptide that is able to retain its histidine ammonia lyase activity in the presence of a histidine analog, like histidinol. As defined herein, a "histidine analog" refers to histidine variants, like histidinol, including therapeutic salts thereof. Histidinol, as a representative histidine analog, possesses many beneficial therapeutic uses, including the ability to inhibit the production of histamine from histidine. Histidinol is also able to alter protein synthesis pathways, by causing deacylation of histidyl tRNA. Because the histidine ammonia lyase activity of a polypeptide according to this invention is not substantially decreased in the presence of a histidine analog, like histidinol, it is uniquely suitable among all other known histidine ammonia lyases for combination therapy with such compounds.

Nucleic acids encoding the inventive peptides also are contemplated, as are conservative variants thereof, in accordance with the "sequence identity" discussion below. The inventive nucleic acids are, of course, useful in preparing the inventive proteins by recombinant means and in implementing gene therapy treatments analogous to the protein-based treatments, discussed below.

Histidine analogs, according to the invention, include compounds of the following structure:

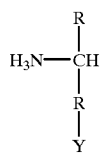

wherein each R is independently a 1-, 2- or 3-carbon alkyl, a 2- to 3-carbon alkene, or a 2- to 3-carbon alkyne, wherein each R independently is optionally substituted one or members of the group consisting of —OH, —SH and =O; and Y is a 5- or 6-membered heterocyclic ring, having one or two hetero atoms selected from the group consisting of N, S and O, including esters and therapeutically effective salts thereof. In some preferred analogs Y is a five-membered ring, having one or two N hetero atoms and in more preferred compounds Y is an imidazole moiety. In certain preferred compounds N is 1. R specifically may be a 1-carbon alkyl. Representative esters include phosphoric acid esters and carboxylic acid esters (especially C1–3). Analogs can include histidinol, histidinal, imidazole glycerol phosphate, imidazole acetol phosphate, and histidinol phosphate. Histidinol has the following structure:

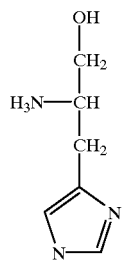

The polypeptides of the present invention have a molecular structure that confers the functional characteristics described herein. In a preferred embodiment, the region is conserved that corresponds to the active site, denoted by SEQ ID NO: 1. Accordingly, the peptide sequences delineated by SEQ ID NOS: 2, 3, 4, and 5 are encompassed by the invention because they conserve the active site of the novel polypeptide. Likewise, SEQ ID NOS: 8, 9, and 10 conserve the active site of the novel polypeptide and, accordingly, are contemplated by the invention.

Within the present invention, moreover, are molecules that do not contain the active site, but are variants of the aforementioned peptides by virtue of one or more conservative substitution, such as cysteine for serine—both of which are sulfur-containing amino acids—that maintain histidine ammonia lyase activity in the presence of a histidinol analog. A "conservative substitution" may be made, for instance, on the basis of similarity in polarity, charge, solubility, hydrophobicity, hydrophilicity, and/or the amphipathic nature of the residues involved.

Thus, the overall structure and composition of inventive polypeptides are important only insofar as they confer the appropriate functional characteristics, i.e., histidine-depleting and relative resistance to a histidine analog, such as histidinol. Given the properties of the individual amino acids comprising the disclosed protein products, some rational substitutions will be recognized by the skilled worker. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)–(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices; while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist can readily construct DNAs encoding the conservative amino acid variants.

In general, both the DNA and protein molecules of the invention can be defined with reference to "sequence identity." Some molecules have at least 60% identity. Preferred molecules are those having at least about 65% sequence identity, more preferably at least 65% or 70% sequence identity. Other preferred molecules have at least 80%, more preferably at least 80% or 85%, sequence identity. Particularly preferred molecules have at least about 90% sequence identity, more preferably at least 90% sequence identity. Most preferred molecules have at least about 95%, more preferably at least 95%, sequence identity. As used herein, two nucleic acid molecules or proteins are said to "share significant sequence identity" if the two contain regions which possess greater than 85% sequence (amino acid or nucleic acid) identity.

"Sequence identity" is defined herein with reference the Blast 2 algorithm, which is available at the NCBI (http://www.ncbi.nlm.nih.gov/BLAST), using default parameters. References pertaining to this algorithm include: those found at http://www.ncbi.nlm.nih.gov/BLAST/blast_references.html; Altschul, S. F., Gish, W., Miller, W., Myers, E. W. & Lipman, D. J. 1990. *J. Mol. Biol.* 215:403–410; Gish, W. & States, D. J. 1993. *Nature Genet.* 3:266–272; Madden, T. L., Tatusov, R. L. & Zhang, J. 1996. *Meth. Enzymol.* 266:131–141; Altschul, S. F., Madden, T. L., Sch affer, A. A., Zhang, J., Zhang, Z., Miller, W. & Lipman, D. J. 1997. *Nucleic Acids Res*. 25:3389–3402; and Zhang, J. & Madden, T. L. 1997. *Genome Res*. 7:649–656.

To this end, SEQ ID NO: 6, for example, delineates sequence variations that are contemplated by the invention. The amino acid positions not represented by "X" represent 1) highly conserved regions among known histidine ammonia lyases (see e.g., FIG. 15), as well as 2) amino acids that are unique to the polypeptide isolated from Corynebacteriaceae. Regions corresponding to the absence of an amino acid are denoted by "-", shown in FIG. 14. Amino acid positions delineated by "X" represent regions where the amino acid can vary without departing from the invention. According to SEQ ID NO: 6, the amino acids represented by "X" can be an amino acid that is present in the corresponding position of any other histidine ammonia lyase. For instance, FIG. 14 denotes Alanine at position 14 of the HAL isolated from Corynebacteriaceae. In histidine ammonia lyases isolated from those species depicted in FIG. 14, the amino acid at the position corresponding to position 14 in Corynebacteriaceae are: threonine, alanine, valine, leucine, asparagine, aspartic acid, and proline, as shown in FIG. 14. Accordingly, position 14 of the polypeptide contemplated by the invention can be represented by any one of these amino acids. To further illustrate the contemplated variation, the amino acid corresponding to position 241 can be Phenylalanine, leucine, tyrosine, alanine, or cysteine.

The Following Legend is used to describe the species associated with the peptides disclosed in FIG. 14.

```
983831        : HAL
              CAC21618    : Streptomyces coelicolor
HUTH_STRGR  : Streptomyces griseus
HUTH_DEIRA  : Deinococcus radiodurans
4             BAB16159    : Agrobacterium rhizogenes
5             Q9KWE4      : Agrobacterium rhizogenes
HUTH_BACSU  : Bacillus subtilis
7             Q9KSQ4      : Vibrio cholerae
8             Q9HU85      : Pseudomonas aeruginosa
9             Q9KBE6      : Bacillus halodurans
HUTH_PSEPU  : Pseudomonas putida
HUTH_RHIME  : Rhizobium meliloti
12            Q9HU90      : Pseudomonas aeruginosa
HUTH_HUMAN  : Human
HUTH_CAEEL  : Caenorhabditis elegans
15            Q9HLI6      : Thermoplasma acidophilum
HUTH_MOUSE  : Mouse
17            BAB29407    : Mus musculus (Mouse)
18            HUTH_RAT    : Rat
18            AAG53586    : uncultured bacterium pCosAS1
20            Q9KKEO      : Rhizobium meliloti
21            Q9HQD5      : Halobacterium sp
```

A further example, as shown by SEQ ID NO: 11, delineates other contemplated peptides, which can be formulated by referencing the histidine ammonia lyases set forth in FIG. 13. As in SEQ ID NO: 6, the amino acid positions not represented by "X" represent 1) highly conserved regions among known histidine ammonia lyases, as well as 2) amino acids that are unique to the polypeptide isolated from Corynebacteriaceae. Regions that may correspond to the absence of an amino acid are denoted by "-", shown in FIG. 13. Amino acid positions delineated by "X" represent regions where the amino acid can vary without departing from the invention. The amino acids represented by "X" can be an amino acid that is present in the corresponding position of any other histidine ammonia lyase. For instance, FIG. 13 denotes Threonine at position 8 of the HAL isolated from Corynebacteriaceae. In histidine ammonia lyases isolated from other species, the amino acid at the position corresponding to position 8 in Corynebacteriaceae are threonine, isoleucine, alanine, glutamate, and valine, also shown in FIG. 13. Accordingly, position 8 of the polypeptide contemplated by the invention can be represented by any one of these amino acids. To further illustrate the contemplated variation, the amino acid corresponding to position 307 can be alanine, aspartate, glycine, glutamate, or arginine.

In addition to having varying peptide sequences, the polypeptides contemplated by the invention can possess varying molecular weights, without departing from the invention, so long as one or more of the novel properties, as disclosed herein, are maintained. Accordingly, a polypeptide can have a monomeric molecular weight between about 30,000 to 67,000 daltons. More preferably, the monomeric molecular weight is between about 45,000 and 60,000 daltons. It is most preferred that the monomeric molecular weight is about 56,000 daltons.

Therapeutic Compositions

The proteins of the present invention can be formulated according to known methods to prepare pharmaceutically useful compositions, whereby the inventive molecules, or their functional derivatives, are combined in a mixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of one or more of the proteins of the present invention, together with a suitable amount of carrier vehicle.

Pharmaceutical compositions for use in accordance with the present invention may be formulated in conventional manner using one or more physiologically acceptable carriers or excipients. Thus, the inventive polypeptides and their physiologically acceptable salts and solvate may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the composition may take the form of tablets or lozenges formulated in conventional manner.

For administration by inhalation, the novel polypeptide for use according to the present invention is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The novel polypeptide may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the novel polypeptide may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which contain one or more unit dosage forms containing the active ingredient. The pack may for example comprise metal or plastic foil, such as a blister pack. The pack or dispenser device may be accompanied by instructions for administration.

Methods of the Invention:
Therapeutic Rationale
Viral Fighting Properties

In one embodiment, the inventive polypeptides possess hitherto unknown uses for treating human infectious viruses, including DNA and RNA viruses. It has been discovered by the present inventors the novel polypeptides are surprisingly potent inhibitors of RNA, DNA and retroviruses viruses. Histidine ammonia lyase therapy by itself and in combination with histidinol is effective against these three main groups of viruses. The unique broad-spectrum antiviral activity of HAL is a highly desirable characteristic for an antiviral agent.

Specific viruses that can be treated according to the invention include, but are not limited to, human Respiratory Syncytial Virus (RSV), Herpes Simplex Virus (HSV) and Human Immunodeficiency Virus (HIV). The latter virus can be treated in accordance with the present invention, based on the observation that inventive polypeptide was able to inhibit viral replication in the Rauscher Murine Leukemia Virus, a model virus for HIV. Other treatable viruses include the following closely related viruses.

Respiratory syncytial virus belongs to the family Paramyxoviridae. The other human infectious viruses belonging to the family Paramyxoviridae include: Parainfluenza 1, 2, 3, 4 viruses which cause upper respiratory disease, bronchitis/bronchiolitis, pneumonia; mumps virus, and measles virus. The family Paramyxoviridae is very closely related to Rhabdoviridae and Filoviridae because the viruses belonging to these families contain a single-stranded RNA (negative sense) genome which is non-segmented and enveloped. Human infectious viruses belonging to Rhabdoviridae are vesicular stomatitis-Indiana, New Jersey, cocal viruses, chandipura virus, Piry virus, Isfahan virus, rabies virus, Mokola virus, and Duvenhage virus. Human infectious viruses belonging to the family Filoviridae include Marburg and Ebola viruses. More broadly, Respiratory Syncytial Virus is an RNA virus.

Other RNA viruses that cause human infections include the following: polioviruses 1, 2, and 3; coxsackieviruses B1–B6; human echoviruses 1–9, 11–27, and 29–34; human enteroviruses 1–113; Norwalk virus and similar viruses that belong to the family Caliciviruses that cause gastroenteritis in humans; eastern equine encephalitis virus; western equine encephalitis virus; Venezualan equine encephalitis virus; chikungunya virus; O'nyong-nyong virus; Ross River virus; Mayarovirus; rubella virus; yellow fever virus; dengue viruses; Western Nile virus; St. Louis encephalitis virus; Japanese encephalitis virus; Murray Valley encephalitis virus; Rocio virus; tick-borne encephalitis viruses; human coronaviruses 229-E and OC43; upper respiratory tract infection, probably pneumonia and possibly gastroenteritis; influenza A, B, and C viruses; Bunyamwera virus; Bwamba virus; Oriboca virus; Oropouche virus; Gwama virus; California encephalitis virus; LaCrosse virus; Tahyna virus; Sandfly fever-Naples virus; Crimean-Congo hemorrhagic fever virus; Hantaan virus (Korean hemorrhagic fever, hemorrhagic fever with renal syndrome, nephropalthia epidemica); lymphocytic choriomeningitis (LCM) virus; Lassa virus; Machupa virus (Bolivian hemorrhagic fever); Junin virus (Argentine hemorrhagic fever); reovirus 1, 2, and 3; Orungo virus (febrile illness in Nigeria and Uganda); Kemerovo virus (febrile illness in Russia and Egypt); human rotaviruses, Colorado tick fever virus.

Rauscher Murine Leukemia virus belongs to the family Retroviridae. Viruses that belong to this family have a single-stranded (positive sense), non-segmented enveloped genome, but they involve a DNA step in replication. Human infectious viruses belonging to this family include type C oncoviruses such as human T-lymphotropic virus 1 (HTLV-I, adult T-cell leukemia) and human T-lymphotropic virus 2 (HTLV-II, possibly associated with hairy-cell leukemia), human immunodeficiency viruses 1 and 2 (HIV 1 and HIV 2) that cause acquired immunodeficiency syndrome (AIDS) and other viruses, related to HIV 1 and HIV 2, which cause AIDS-like disease.

Herpes Simplex Virus belongs to the family Herpesviridae. Viruses belonging to the family Herpesviridae have a double-stranded enveloped genome, a property that they share with viruses belonging to the families Poxviridae and Iridoviridae. Human infectious viruses belonging to the family Herpesviridae include Herpes Simplex Viruses 1 and 2, cercopilthecine, herpesvirus 1 (B-virus), varicella-Zoster virus, human cytomegalovirus, EB virus, and human herpesvirus 6. Human infectious viruses belonging to Poxviridae include variola virus (smallpox, alastrim), vaccinia virus, monkeypox virus, cowpox virus, orf virus (contagious pustular dermatitis), pseudo-cowpox (milker's nodule) virus, yabapox virus, tanapox virus, and molluscum contagiosum virus. More broadly, Herpes Simplex Virus is a DNA virus and other human infectious viruses in this category are hepatitis B virus; human parvovirus B-19, parvovirus RA-1, and other parvoviruses that cause gastroenteritis; human papillomaviruses (HPV) 1–48); polyomaviruses such as JC, SV40 and BK; and Adenoviruses such as Mastadenovirus h1–h49.

Polypeptides that have a histidase activity are able to combat viruses by inhibiting viral replication, for example, in the absence of a histidine analog. However, a greater therapeutic benefit is achieved, when treating viruses, if the polypeptides of the invention are employed in conjunction with a histidine analog, like histidinol, as shown in Example 11. In fact, a synergistic effect is observed when HAL- and histidine analog-directed therapies are combined, also shown in Example 11. Accordingly, the invention contemplates polypeptides that can be used to treat infectious viruses by virtue of the polypeptide's histidine depleting activity, either alone or in combination with a histidine analog.

Cancer Fighting Properties

In another aspect, the inventive polypeptide is able to function as an anticancer agent. In vitro, the polypeptides of the invention are effective in controlling the growth of a variety of human tumors. For example, the growth of different prostate and ovarian cancer cell lines has been inhibited by the inventive polypeptides, as shown in Example 12.

By virtue of their anti-carcinogenic activity in vitro, the polypeptides of the invention can also be used to inhibit malignant tumor proliferation in vivo. In addition, any of the novel polypeptides are a suitable candidate for an anticancer agent that can be used in combination therapy with other anticancer agents, as described below. In particular, the polypeptides of the present invention can be administered to a patient in the presence of a histidine analog, like histidinol, due to the novel polypeptides' ability to retain histidine ammonia lyase activity in the presence of such compounds.

There are numerous types of cancers that can be treated according to the invention, including prostate and ovarian cancer, and glioblastomas. Other types of cancers that may be treated include: chronic and acute leukemia, cancer of the bone, brain, breast cartilage, cervix, esophagus, kidney, larynx, liver, lung, pancreas, and uterus. In addition, the polypeptides of the invention may be used to combat Hodgkin's Disease, lymphoma, melanoma, multiple myeloma, colo-rectal, and testicular cancer.

Quiescent-inducing Properties

It has been discovered that incubation in histidine-deficient medium has been able to cause non-transformed mammalian cells to enter a reversible inactive, or "quiescent," state at a specific point during the cell cycle, called the "restriction point." Newman et al. 1983. *Anticancer Research.* 43:4703. This quiescent state is characterized by an absence of DNA synthesis and reduced rates of ribosomal RNA and protein synthesis. These and a series of other metabolic events associated with growth quiescence are reversible, and have been termed the "negative pleiotypic response." In contrast to the reversible arrest of normal cells by nutritional manipulations, transformed cell lines seem to have lost their ability to stop proliferation at the restriction point, as reported by Pardee et al. *Annual Rev. Biochem.* 47:715–750 (1974); and Pardee, *Proc. Natl. Acad. Sci. U.S.A.* 71: 1286–1290 (1974) and Newman et al., (1983), supra.

This fundamental difference between normal and malignant cells can be exploited to selectively kill transformed cells under conditions that leave normal cells intact. For example, chemotherapeutic drugs function preferentially against proliferating cells, with no significant capacity to discriminate between cycling normal and cycling tumor tissues. Previously, Newman et al., *Anticancer Res.* 43: 4703 (1983) were able to drive a cell line (BALB/3T3) into a quiescent state by incubating the cell line in a histidine-deficient medium. This methodology protected the cells from the lethal effects of Methotrexate. Warrington, *Anticancer Res.* 6: 451 (1986), and Biochem. *Cell Biol.* 70: 365 (1992), reported similar findings, but instead used a histidine analog in place of a histidine-deficient medium. These findings led to the conclusion by Warrington (1986), supra, that cancer chemotherapeutic agents are selective when the tumor cell population has a higher growth fraction than normal cells. Thus, arresting the growth of normal cells without impacting the growth of tumor cells would confer selectivity to the anti-proliferative drugs commonly used in cancer chemotherapy.

In this context, a histidine ammonia lyase is a suitable candidate to selectively deplete the circulating histidine, since the histidine depleting activity of histidine ammonia lyase will cause growth arrest in normal cells, without affecting the growth of tumor cells. A histidine ammonia lyase can also be used in combination with a histidine analog such as L-histidinol, where the histidine ammonia lyase activity is not substantially decreased in the presence of the histidine analog. Accordingly, chemotherapeutic drugs would be less inclined to react with quiescent cells and confer less toxicity to a patient, thereby increasing the therapeutic index of cancer chemotherapy.

In one embodiment, patients who would undergo cancer chemotherapy first can be given an injection of an effective dose of a histidine ammonia lyase (e.g. between 1 $\mu$g and 1 gram per kg body weight, administered intravenously). About twenty-four hours after histidine ammonia lyase injection, a conventional chemotherapeutic agent, such as one of those described herein, can then be administered to the patient. However, the invention also contemplates a method of administering several doses of a conventional chemotherapeutic agent to a patient after about 24 hours following the injection of a histidine ammonia lyase. The type of chemotherapy will vary with the type of cancer and also will be based on the suitability of the chemotherapeutic agent to a particular patient.

In yet another aspect of the invention, a histidine ammonia lyase can be used to enhance the specificity of cancer gene therapy. Retroviral vectors are one of the commonly used vehicles to deliver therapeutic genes for selectively killing tumor cells. However, retroviruses deliver DNA into growing cells without significant capacity to discriminate between cycling normal and cycling tumor tissues. Accordingly, retroviral therapy also suffers from the problem of killing high concentrations of non-targeted, healthy (i.e. non-tumor) cells that are proliferating at a given time in the human body. To obviate these problems, a histidine ammonia lyase can be first administered to a patient, thereby causing normal (i.e. non-tumor) cells to enter a reversible quiescent state. For example, an intravenous injection of 1 $\mu$g to 1 g of HAL reacted with polyethylene glycol ("PEGylated HAL") per kg body weight can be given to a patient 24 hours prior to the injection of retroviral vector. This treatment would arrest the growth of normal cells without affecting the growth of cancer cells. As a result, retroviral vectors would selectively target proliferating tumor cells.

Immunosuppressant Properties

In another embodiment, the invention contemplates methodologies for delivering an immunosuppressant to a patient. The products of the enzymatic action of histidine ammonia lyase are trans-urocanic acid (t-UA) and ammonia. Irradiation at approximately 310 nm causes the photoisomerization of t-UA to its cis isomer (c-UA), as noted by Hanson et al., *Proc. Natl. Acad. Sci. U.S.A.* 95: 10576–10578 (1998). Cis-urocanic acid is believed to play the role of one of the UVB-induced immunosuppressive mediators (Kripke, *Cancer Res.* 54: 6102–6105 (1994); and Norval et al., *Photochem. Photobiol.* 62: 209–217 (1995)). This immunosuppressive property of urocanic acid can be used, for example, to treat immune system disorders and to prevent rejection of transplanted organs.

Although in theory, such an approach promises to provide a therapeutic benefit, small molecules like urocanic acid are rapidly cleared from circulation, thereby limiting their use as effective immunosuppressors over prolonged periods of time. However, it has been discovered that PEGylated HAL has a long circulatory half-life in mice (over 48 hours). Thus, an effective dose (1 $\mu$g to 1 g per kg body weight) of a histidine ammonia lyase can be used to generate circulating urocanic acid for prolonged periods of time. In turn, a cis-isomerizing agent, such as UVB irradiation, can be used to cause local immunosuppression (for conditions such as psoriasis), or systemic immunosuppression, the process of which subjects the patient to whole body irradiation. In one example, whole body irradiation can be employed according to the invention, to combat organ rejection following transplantation.

In another embodiment, selective immunosuppression can be achieved by targeting the UVB irradiation. For example, psoriasis could be treated by an injection of a histidine ammonia lyase followed by selective irradiation of the affected areas. Selective UVB irradiation, following the injection of a histidine ammonia lyase into a patient, can also be used to treat conditions like arthritis.

In a further embodiment, localization and/or specificity of immunosuppression could also be achieved by targeting a histidine ammonia lyase to specific organs. To this end, the invention contemplates a fusion protein comprising one or more targeting peptide sequences in addition to the coding regions of a selected histidine ammonia lyase. Pasqualini et al. *Nature* 380: 364–366 (1996), have reported the success of targeting various proteins to specific organs via this methodology.

Treatment Methods

Therapeutic methods involve administering to a subject in need of treatment a therapeutically effective amount of a polypeptide contemplated by the invention. "Therapeutically effective" is employed here to denote the amount of a peptide that is of sufficient quantity to inhibit or reverse cancer growth (e.g., induce apoptosis). Some methods contemplate combination therapy with known cancer medicaments or therapies, for example, chemotherapy (preferably using compounds of the sort listed above) or radiation. The patient may be a human or non-human animal. A patient typically will be in need of treatment when suffering from a pathology such as a cancer or virus described above.

As previously demonstrated, the histidine ammonia lyase activity of the novel polypeptide is not substantially decreased in the presence of a histidine analog, like histidinol. A typical method, accordingly, involves administering to a patient both the novel polypeptide and the selected histidinol according to the methods described herein. In one embodiment, the novel polypeptide can be administered simultaneously with a chosen histidinol. In another embodiment, the novel polypeptide is first administered to a patient, followed by a selected histidinol. In yet another embodiment, a histidine analog, such as histidinol, is first administered to a patient followed by the novel polypeptide. The invention also contemplates administering multiple dosages of the novel polypeptide or chosen histidinol in conjunction with the methods described herein (i.e. administering two or more dosages of the novel polypeptide, followed by at least one dosage of a histidine analog, like histidinol).

Administration during in vivo treatment may be by any number of routes, including parenteral and oral, but preferably parenteral. Intracapsular, intravenous, intrathecal, and intraperitoneal routes of administration may be employed, and generally intravenous is preferred. The skilled artisan will recognize that the route of administration will vary depending on the disorder to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484–528 (Mack Publishing Company 1990).

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the induction or substantial induction of T lymphocyte cytotoxicity at the targeted tissue or a decrease in mass of the targeted tissue.

Suitable dosages can be preferably from about one microgram per kg body weight to one gram per kg body weight, and more preferably from 2 milligrams to 10 mg per kg body weight.

The compositions, since they are useful in cancer treatment, may be formulated in conjunction with other conventional methods of treatment. Conventional methods include administering a histidine analog, like histidinol. Such forms of treatment also include conventional chemotherapeutic agents. Conventional chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tomoxifen, testosterone propionate and fluoxymesterone. In treating breast cancer, for example, tamoxifen is particularly preferred.

The invention further contemplates the administering to a patient a peptide of the invention in conjunction with alkylating agents, antimetabolites, various natural products (e.g., vinca alkaloids, epipodophyllotoxins, antibiotics, or amino acid-depleting enzymes) hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tomoxifen, testosterone propionate and fluoxymesterone.

Construction of the Inventive Polypeptide

A polypeptide according to this invention can be isolated by conventional means and the present invention is not limited to any particular method of producing the desired polypeptide contemplated herein. According to the contemplated recombinant methods of production, however, the invention provides recombinant DNA constructs comprising one or more of the nucleotide sequences of the domains described in the present invention. The recombinant constructs of the present invention comprise a vector, such as a plasmid or viral vector, into which a DNA or DNA fragment, typically bearing an open reading frame, is inserted, in either orientation. The invention further contemplates cells containing these vectors.

To this end, the DNA that encodes a novel polypeptide is first isolated using well known techniques. For instance, Example 1 provides one non-limiting method for isolating such targeted genomic DNA. This methodology includes culturing selected cells before extracting the genomic DNA from the culture, followed by subjecting the DNA to a series of restriction enzymes, whereby generated genomic DNA fragments can be studied and isolated by conventional techniques, for example, agarose gel electrophoresis.

Next, a vector can be selected and, likewise, cut with a restriction enzyme to generate a vector fragment by a methodology that is consistent with the procedure used to isolate the genomic DNA. Suitable vectors include bacterial and mammalian expression systems, as described below. After a suitable vector is selected, varying concentrations of the DNA fragment ("insert") can be placed into contact with the vector, as shown in Example 1, to determine the best insert:vector ratio for transformation of the DNA fragments. The transformants can then be cultured to generate copies of the DNA fragments.

To isolate the domains of a novel polypeptide from the generated DNA fragment, DNA probes can be designed by virtue of selecting sequences that are highly conserved in known histidine ammonia lyases. As shown in Example 1, the Wisconsin Graphics GCG package pileup program provides one method of determining highly conserved regions. A selected probe can be used to screen the targeted genomic DNA library, for example, using technology as disclosed by Ausubel et al., CURRENT PROTOCOLS IN MOLECULAR BIOLOGY, (John Wiley & Sons, 1994). Example 1 provides a non-limiting embodiment for utilizing suitable probes to screen the genomic library, followed by a series of steps to purify the genomic clones.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may, also be employed as a matter of choice. In a preferred embodiment, the prokaryotic host is *E. coli,* as shown in Example 3.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBS, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is Bluescript vector (pBSSK)—(Stratagene).

These "backbone" sections are combined with an appropriate promoter and the structural sequence to be expressed. Bacterial promoters include lac, T3, T7, lambda $P_R$ or $P_L$, trp, and ara. The T7 promoter is preferred.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems can also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-I. Exemplary mammalian vectors include pWLneo, pSV2cat, pOG44, pXT1, pSG (Stratagene) pSVK3, pBPV, pMSG, and pSVL (Pharmacia).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, *Proc. Natl. Acad. Sci.* USA 81:3655–3659).

Extension of Half-life and Prevention of Antibody Formation to the Inventive Peptide (PEGylating)

The invention also contemplates a polypeptide that can be induced to have an increased half-life. To this end, the polypeptide is manipulated by conventional techniques, such as modification with polyethylene glycol (PEGylation). According to this methodology, a suitable amount of a PEGylating agent is reacted with a polypeptide of the invention before introducing the polypeptide to a targeted cell culture or tissue. In one embodiment, the PEGylating agent is BTC-PEG 5000 (Shearwater Polymers, Inc.); however, the invention contemplates other PEGylating agents. Example 10 provides a non-limiting method to construct a PEGylated peptide in accordance with the invention.

A PEGylated polypeptide has practical applications both in vitro and in vivo. For example, a polypeptide's ability to sustain its enzymatic properties for an increased amount of time would permit a decrease in the dosage necessary to ameliorate one or more symptoms associated with a targeted pathology. In addition, a PEGylated polypeptide can possess an increased resistance to antibody-mediated depletion in the host. According to this embodiment, the PEGylating agent is believed to inhibit a host's antibody-mediated response against the polypeptide.

Gene Therapy Applications:

By virtue of discovering the DNA sequences that encode the novel polypeptides disclosed herein, the invention contemplates the use of these sequences in gene therapy approaches. To this end, a promoter and the DNA that encodes a polypeptide according to the invention is inserted into a vector, which is then introduced into a subject suffering from a pathology, such as a cancer or infectious virus.

The construction of a suitable vector can be achieved by any of the methods well-known in the art for the insertion of exogenous DNA into a vector. See, e.g., Sambrook et al., *Molecular Cloning* (Cold Spring Harbor Press 2d ed. 1989), which is incorporated herein by reference. In addition, the prior art teaches various methods of introducing exogenous genes into cells in vivo. See Rosenberg et al., *Science* 242:1575–1578 (1988), and Wolff et al., *PNAS* 86:9011–9014 (1989), which are incorporated herein by reference. The routes of delivery include systemic administration and administration in situ. Well-known techniques include systemic administration with cationic liposomes, and administration in situ with viral vectors. Any one of the gene delivery methodologies described in the prior art is suitable for the introduction of a recombinant vector containing an inventive gene according to the invention into a MTX-resistant, transport-deficient cancer cell. A listing of present-day vectors suitable for the purpose of this invention is set forth in Hodgson, *Bio/Technology* 13: 222 (1995), which is incorporated by reference.

For example, liposome-mediated gene transfer is a suitable method for the introduction of a recombinant vector containing an inventive gene according to the invention into a MTX-resistant, transport-deficient cancer cell. The use of a cationic liposome, such as DC-Chol/DOPE liposome, has been widely documented as an appropriate vehicle to deliver DNA to a wide range of tissues through intravenous injection of DNA/cationic liposome complexes. See Caplen et al., *Nature Med.* 1:39–46 (1995) and Zhu et al., *Science* 261:209–211 (1993), which are herein incorporated by reference. Liposomes transfer genes to the target cells by fusing with the plasma membrane. The entry process is relatively efficient, but once inside the cell, the liposome-DNA complex has no inherent mechanism to deliver the DNA to the nucleus. As such, the most of the lipid and DNA gets shunted to cytoplasmic waste systems and destroyed. The obvious advantage of liposomes as a gene therapy vector is that liposomes contain no proteins, which thus minimizes the potential of host immune responses.

As another example, viral vector-mediated gene transfer is also a suitable method for the introduction of the vector into a target cell. Appropriate viral vectors include adenovirus vectors and adeno-associated virus vectors, retrovirus vectors and herpesvirus vectors.

Adenoviruses are linear, double stranded DNA viruses complexed with core proteins and surrounded by capsid proteins. The common serotypes 2 and 5, which are not associated with any human malignancies, are typically the base vectors. By deleting parts of the virus genome and inserting the desired gene under the control of a constitutive viral promoter, the virus becomes a replication deficient vector capable of transferring the exogenous DNA to differentiated, non-proliferating cells. To enter cells, the adenovirus fibre interacts with specific receptors on the cell surface, and the adenovirus surface proteins interact with the cell surface integrins. The virus penton-cell integrin interaction provides the signal that brings the exogenous gene-containing virus into a cytoplasmic endosome. The adenovirus breaks out of the endosome and moves to the nucleus, the viral capsid falls apart, and the exogenous DNA enters the cell nucleus where it functions, in an epichromosomal fashion, to express the exogenous gene. Detailed discussions of the use of adenoviral vectors for gene therapy can be found in Berkner, *Biotechniques* 6:616–629 (1988) and Trapnell, *Advanced Drug Delivery Rev.* 12:185–199 (1993), which are herein incorporated by reference. Adenovirus-derived vectors, particularly non-replicative adenovirus vectors, are characterized by their ability to accommodate exogenous DNA of 7.5 kB, relative stability, wide host range, low pathogenicity in man, and high titers ($10^4$ to $10^5$ plaque forming units per cell). See Stratford-Perricaudet et al., *PNAS* 89:2581 (1992).

Adeno-associated virus (AAV) vectors also can be used for the present invention. AAV is a linear single-stranded DNA parvovirus that is endogenous to many mammalian species. AAV has a broad host range despite the limitation that AAV is a defective parvovirus which is dependent totally on either adenovirus or herpesvirus for its reproduction in vivo. The use of AAV as a vector for the introduction into target cells of exogenous DNA is well-known in the art. See, e.g., Lebkowski et al., *Mole. & Cell. Biol.* 8:3988 (1988), which is incorporated herein by reference. In these vectors, the capsid gene of AAV is replaced by a desired DNA fragment, and transcomplementation of the deleted capsid function is used to create a recombinant virus stock. Upon infection the recombinant virus uncoats in the nucleus and integrates into the host genome.

Another suitable virus-based gene delivery mechanism is retroviral vector-mediated gene transfer. In general, retroviral vectors are well-known in the art. See Breakfield et al., *Mole. Neuro. Biol.* 1:339 (1987) and Shih et al., in *Vaccines* 85: 177 (Cold Spring Harbor Press 1985). A variety of retroviral vectors and retroviral vector-producing cell lines can be used for the present invention. Appropriate retroviral vectors include Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. These vectors include replication-competent and replication-defective retroviral vectors. In addition, amphotropic and xenotropic retroviral vectors can be used. In carrying out the invention, retroviral vectors can be introduced to a tumor directly or in the form of free retroviral vector producing-cell lines. Suitable producer cells include fibroblasts, neurons, glial cells, keratinocytes, hepatocytes, connective tissue cells, ependymal cells, chromaffin cells. See Wolff et al., *PNAS* 84:3344 (1989).

Retroviral vectors generally are constructed such that the majority of its structural genes are deleted or replaced by exogenous DNA of interest, and such that the likelihood is reduced that viral proteins will be expressed. See Bender et al., *J. Virol.* 61:1639 (1987) and Armento et al., *J. Virol.* 61:1647 (1987), which are herein incorporated by reference. To facilitate expression of the novel protein, a retroviral vector employed in the present invention must integrate into the genome of the host cell genome, an event which occurs only in mitotically active cells. The necessity for host cell replication effectively limits retroviral gene expression to tumor cells, which are highly replicative, and to a few normal tissues. The normal tissue cells theoretically most likely to be transduced by a retroviral vector, therefore, are the endothelial cells that line the blood vessels that supply blood to the tumor. In addition, it is also possible that a retroviral vector would integrate into white blood cells both in the tumor or in the blood circulating through the tumor.

The spread of retroviral vector to normal tissues, however, is limited. The local administration to a tumor of a retroviral vector or retroviral vector producing cells will restrict vector propagation to the local region of the tumor, minimizing transduction, integration, expression and subsequent cytotoxic effect on surrounding cells that are mitotically active.

Both replicatively deficient and replicatively competent retroviral vectors can be used in the invention, subject to their respective advantages and disadvantages. For instance, for tumors that have spread regionally, such as lung cancers, the direct injection of cell lines that produce replication-deficient vectors may not deliver the vector to a large enough area to completely eradicate the tumor, since the vector will be released only from the original producer cells and their progeny, and diffusion is limited. Similar constraints apply to the application of replication deficient vectors to tumors that grow slowly, such as human breast cancers which typically have doubling times of 30 days versus the 24 hours common among human gliomas. The much shortened survival-time of the producer cells, probably no more than 7–14 days in the absence of immunosuppression, limits to only a portion of their replicative cycle the exposure of the tumor cells to the retroviral vector.

The use of replication-defective retroviruses for treating tumors requires producer cells and is limited because each replication-defective retrovirus particle can enter only a single cell and cannot productively infect others thereafter. Because these replication-defective retroviruses cannot spread to other tumor cells, they would be unable to completely penetrate a deep, multilayered tumor in vivo. See Markert et al., *Neurosurg.* 77: 590 (1992). The injection of replication-competent retroviral vector particles or a cell line that produces a replication-competent retroviral vector virus may prove to be a more effective therapeutic because a replication competent retroviral vector will establish a productive infection that will transduce cells as long as it persists. Moreover, replicatively competent retroviral vectors may follow the tumor as it metastasizes, carried along and propagated by transduced tumor cells. The risks for complications are greater, with replicatively competent vectors, however. Such vectors may pose a greater risk then replicatively deficient vectors of transducing normal tissues, for instance. The risks of undesired vector propagation for each type of cancer and affected body area can be weighed against the advantages in the situation of replicatively competent verses replicatively deficient retroviral vector to determine an optimum treatment.

Both amphotropic and xenotropic retroviral vectors may be used in the invention. Amphotropic viruses have a very broad host range that includes most or all mammalian cells, as is well known to the art. Xenotropic viruses can infect all mammalian cells except mouse cells. Thus, amphotropic and xenotropic retroviruses from many species, including cows, sheep, pigs, dogs, cats, rats, and mice, inter alia can be used to provide retroviral vectors in accordance with the invention, provided the vectors can transfer genes into proliferating human cells in vivo.

Clinical trials employing retroviral vector therapy treatment of cancer have been approved in the United States. See Culver, *Clin. Chem.* 40: 510 (1994). Retroviral vector-containing cells have been implanted into brain tumors growing in human patients. See Oldfield et al., *Hum. Gene Ther.* 4: 39 (1993). These retroviral vectors carried the HSV-1 thymidine kinase (HSV-tk) gene into the surrounding brain tumor cells, which conferred sensitivity of the tumor cells to the antiviral drug ganciclovir. Some of the limitations of current retroviral based cancer therapy, as described by Oldfield are: (1) the low titer of virus produced, (2) virus spread is limited to the region surrounding the producer cell implant, (3) possible immune response to the producer cell line, (4) possible insertional mutagenesis and transformation of retroviral infected cells, (5) only a single treatment regimen of pro-drug, ganciclovir, is possible because the "suicide" product kills retrovirally infected cells and producer cells and (6) the bystander effect is limited to cells in direct contact with retrovirally transformed cells. See Bi et al., *Human Gene Therapy* 4: 725 (1993).

Yet another suitable virus-based gene delivery mechanism is herpesvirus vector-mediated gene transfer. While much less is known about the use of herpesvirus vectors, replication-competent HSV-1 viral vectors have been described in the context of antitumor therapy. See Martuza et al., *Science* 252: 854 (1991), which is incorporated herein by reference.

The following examples are intended to be illustrative and not limiting.

WORKING EXAMPLES

Example 1

Isolation of the DNA Encoding HAL

The bacterium from the family Corynebacteriaceae that produces bioactive histidine ammonia lyase (HAL) was grown in 100 ml of Luria broth overnight at 30° C. The cells were harvested and resuspended in 10 ml of 50 mM Tris (pH 7.5) with 10 mM EDTA. Solid lysozyme was added to 0.2 mg/ml and the suspension was incubated at 4° C. for 30 minutes. Following this incubation, the suspension was frozen for several hours at −70° C. Upon thawing, SDS was added to 0.1% and proteinase K was added to 0.2 mg/ml and was incubated at 37° C. overnight. Next, RNAse was added to 0.1 mg/ml and the mixture incubated at 55° C. for 30 minutes. The resulting DNA was extracted five times with an equal volume of phenol/chloroform (1:1) and precipitated with 2 volumes of absolute ethanol. The DNA was spooled out on a glass Pasteur pipette, washed with ice cold 70% ethanol, and resuspended in a minimal amount of TE buffer.

Genomic DNA was restricted with Sau3AI over a time course of 1 hour. Every ten minutes, an aliquot was removed, taken to 10 mM EDTA, and analyzed by agarose gel electrophoresis. The time point that showed an average fragment size of 1–5 kb was loaded in its entirety and resolved on an agarose gel. The 1–5 kb fragments were isolated with DEAE filter paper, phenol extracted and ethanol precipitated.

The Bluescript vector pBSSK—(Stratagene) was restricted with BamHI and treated with arctic shrimp alkaline phosphatase (USB). The treated, linearized vector was subjected to agarose gel electrophoresis and the linear species were isolated as above with DEAE filter paper.

The resulting vector and genomic DNA fragment concentrations were measured and ligations conducted. These were done using 150 ng of vector in a 10 µl reaction volume. Vector concentration was kept constant and insert was varied at stoichiometries of 0×, 0.5×, 1×, 2×, and 5× that of the vector. Ligations were performed at 4° C. overnight. After ligation, reactions were diluted to 30 µl with water and heated to 65° C. for ten minutes.

The diluted ligation reactions were used to transform freshly prepared electrocompetent XL-1Blue MRF' (Stratagene) cells. Transformed ligations were test plated on MacConkey agar to judge the best insert:vector ratio. Once the optimum ratio had been determined, this was used exclusively for transformation.

Transformants were plated at a cell density of 3 000–10 000 cfu per nylon filter on 150 mm plates containing LB agar with 50 µg/ml ampicillin. Duplicate replica filters were produced and processed for colony hybridization.

DNA probes were designed using regions of known histidine ammonia lyases that had a strong probability of being conserved in HAL. Using the Wisconsin Graphics GCG package pileup program, the peptide sequences of the known histidine ammonia lyases from *B. subtilis, S. griseus, P. putida*, and rat were aligned and examined for highly conserved regions. Several of these were chosen as candidates for probe design. Using the DNA sequences of cloned genes from *Corynebacterium*, a codon preference table was derived. From this a backtranslation was performed resulting in the most likely DNA sequence for the protein region of interest.

Two of the resulting probes (TM63 and TM74), shown in Table 1, below, were labeled, mixed, and used to screen the above genomic library. Oligos were labeled with $\gamma^{32}$PATP using T4 polynucleotide kinase as described (Ausubel, et al, eds, 1994. "Current Protocols in Molecular Biology," John Wiley and Sons, Inc.) and cleaned up using Elutips (Schleicher & Schuell). Hybridization of duplicate filters was carried out in a Bellco hybridization oven at 37° C. using the SSPE protocol as described (Ausubel, et at., eds, "Current Protocols in Molecular Biology," John Wiley and Sons, Inc., 1994). Filters were washed in 6×SSC with 0.5% SDS (Ausubel, et al, eds, "Current Protocols in Molecular Biology," John Wiley and Sons, Inc., 1994) at 37° C. Filters were then washed at successively higher temperatures in 3 M TMAC (Ausubel, et al, eds, "Current Protocols in Molecular Biology," John Wiley and Sons, Inc., 1994) until very little radioactivity could be detected with a survey meter (generally 45–55° C.). Upon exposure to X-Ray film (Kodak X-Omat), colonies which were evident on both replicate filters were picked with a wooden toothpick and transferred to a fresh nylon filter overlaid onto an LB/ampicillin plate. This procedure was repeated until a homogeneous population was achieved.

TABLE 1 oligonucleotides (SEQ ID NOS: 13–31, respectively, in order of appearance) with DNA sequence and approximate coordinates relative to the ATG start codon.

| Name | Length | Sequence (5' to 3') | Coordinates |
|---|---|---|---|
| TM63 | 30 | CGCGTTCAGGACGCATACTCCGTTCGCTGC | 838–867 |
| TM74 | 24 | GCCCATGGAAACGTGGTCTTCCTG | 1370–1393 |
| TM85 | 21 | ATCATCATGCCCGAGTCCACA | 1156–1176 |
| TM87 | 21 | GCCATCAGGAAGACCACGTTT | 990–971 |
| TM89 | 20 | ATGCAGGAAGACCACGTTTC | 1246–1265 |
| TM91 | 21 | ATCGAGGTCCGCCAATGCCAT | 648–628 |
| TM92 | 18 | ACCGGAGCAGCCCAGTGA | 441–424 |
| TM93 | 20 | TGCTTGAAGTATTGCGCCAG | 1403–1422 |
| TM94 | 18 | GATCCTCGGGTGCGATGT | 226–209 |
| TM95 | 18 | ATGCTGATCGGGCTTCGT | 92–74 |
| TM96 | 27 | ATTTGATT<u>CATAT</u>GGCTTCCGCTCCTC | −11→+16 |
| TM97 | 28 | ATCTT<u>GGATCC</u>GAACATGGTGCGTTGCA | Beyond C-Terminus |
| TM98 | 18 | AGCACCAGAT CGATGCAC | 128–145 |

TABLE 1-continued oligonucleotides (SEQ ID NOS: 13-31, respectively,
in order of appearance) with DNA sequence and
approximate coordinates relative to the ATG start codon.

| Name | Length | Sequence (5' to 3') | Coordinates |
|------|--------|---------------------|-------------|
| TM99 | 18 | TGGCATGGGTGAACCGGT | 267–284 |
| TM101 | 18 | ATCAGCGTTGAAGCCCAG | 682–699 |
| TM103 | 18 | ACGTGCTGGACTTCCTTG | 1019–1036 |
| TM105 | 18 | GTGCATAAGGCCCTCGAA | 1501–1518 |
| TM106 | 18 | GAGCTTCGAGGGCCTTAT | 1522–1505 |
| TM109 | 18 | CGAGCAACGCAGCGAGTA | 870–853 |

Purified clones were confirmed by DNA sequencing and comparison to known peptide sequence and to known histidine ammonia lyases from the literature as well as peptide sequence from authentic histidine ammonia lyase from a bacterium belonging to the family Corynebacteriaceae. Using this protocol a primary clone, pHUT23, was isolated and identified as containing HAL coding sequence.

An oligo, TM85, was synthesized to the N-terminal-most region of pHUT23 and used to further screen the genomic library. This resulted in two clones, pHUT26 and pHUT28 which contain sequences more toward the N-terminus of the gene. These clones represent the C-terminal ⅔ of the gene. Another oligo, TM91, was synthesized based on the N-terminal-most sequence. This oligo was used to re-screen existing library plates. This resulted in the isolation of pHUT30, containing the N-terminal ⅓ of the gene. The authenticity of this gene was confirmed by comparison of peptide sequences obtained from the original enzyme isolated from a bacterium from the family Corynebacteriaceae.

Using both the full-length gene and the genomic subclones, the histidine ammonia lyase gene was sequenced in both directions by Sanger's chain-termination DNA sequencing method (USB). The purified double-stranded templates, shown with the primers used in Table 1, were denatured by the standard alkaline-denaturation method.

The sequence data revealed that the intact gene encompasses 1533 base pairs (see SEQ ID NO: 12), encoding a protein of 511 amino acids (see SEQ ID NO: 10). Expression of this open reading frame in E. coli results in a single, approximately 55 kDa polypeptide, as detected by denaturing polyacrylamide gel electrophoresis (see FIG. 5). Appearance of this 55 kDa peptide corresponds with induction of histidine ammonia lyase activity (conversion of L-histidine to urocanic acid), an activity detected by us under these conditions exclusively in E. coli harboring a plasmid containing the full-length HAL gene.

Example 2

Peptide Sequencing of HAL

HAL from a bacterium from the family Corynebacteriaceae that had been partially purified using ammonium sulfate and DEAE—Sephadex was resolved by SDS-PAGE. The separated material was electrophoretically transferred to Immobilon-P and stained with Coomassie Brilliant Blue. The major band of 55 000 daltons was excised and subjected to N-terminal sequencing. This fraction was sent to Commonwealth Biotechnologies, Inc. (Richmond, Va.), cleaved with BrCN, HPLC purified, and fractions sequenced.

Example 3

Expression of Histidine Ammonia Lyase from a Bacterium from the Family Corynebacteriaceae Using a High-Efficiency Prokaryotic Expression System The E. coli expression plasmid pHUT102, depicted in FIG. 4, is designed to express HAL DNA sequences from the strong phage T7 gene 10 promoter using T7 RNA Polymerase. This vector, pSN75, is a derivative of pET11b (Novagen) that has an additional transcriptional terminator inserted upstream of the T7 promoter. This provides the target cassette in as transcriptionally silent a context as possible.

Two mutagenic oligonucleotides, TM96 and TM97 (see Table 1), were synthesized based on histidine ammonia lyase sequence. The N-terminal oligo adds an NdeI site at the ATG start codon and the C-terminal oligo adds a BamHI site just beyond the C-terminus. These were used to thermal cycle amplify the HAL gene out of the genome of a bacterium from the family Corynebacteriaceae. The resulting fragment was restricted with NdeI and BamHI and cloned into pSN75, resulting in pHUT102. This provides histidine ammonia lyase under the control of a T7 promoter with flanking transcriptional terminators to prevent readthrough transcription.

A T7 expression system containing kanamycin as a selectable marker was constructed by cloning the 1 kb kanamycin resistance Pst I cassette excised from pUC4K into the unique Pst I site of pSN75. The new vector, pSN75K is ampicillin sensitive and kanamycin resistant. The Nde I–BamHI fragment containing the HAL coding region was excised from pHUT102 and cloned into NdeI+BamHI cut pSN75K. This expression construct, pHUT200, could readily be used for clinical production of HAL since there is no need to use penicillin antibiotics during the production.

For the purpose of expression, pHUT200 was transformed into BL21(λDE3) harboring pLysS and grown in Terrific broth at 28° C. to OD600 of 0.6. The culture was induced for 4 hours with 0.4 mM IPTG and harvested. Cells were lysed and analyzed by SDS-PAGE and enzyme assay. As measured by these assays, we estimate that the HAL is produced to approximately 30% of the total cell protein (see FIG. 5) and 8% of the soluble protein, representing about 0.2 g per liter of culture.

Example 4

Expression of HAL in a Vector that Directs Periplasmic Localization

The NdeI/BamHI fragment from pHUT102 was excised and purified. The vector, pET12c (Novagen), was likewise cut with NdeI/BamHI and purified. These fragments were ligated and transformed into XL-1 Blue MRF'. The clone, pHUT114, containing the HAL gene as a fusion with a T7 phage periplasmic localization signal under control of a T7 promoter.

For the purpose of expression, pHUT114 was transformed into BL21(λDE3) and grown in Terrific broth supplemented with 75 mM NaCl at 28° C. to OD600 of 0.6 under antibiotic selection. The culture was induced for 4 hours with 0.4 mM IPTG and harvested. Spheroplasts were prepared (Ausubel, et al, eds, "Current Protocols in Molecular Biology," John Wiley and Sons, Inc., 1994) and the supernatant was assayed for enzyme.

This approach yielded active, periplasmic HAL. However, microscopic examination showed the formation of inclusion bodies. This resulted in relatively low per volume yield and a specific activity comparable to the cellularly localized material. At this point, this approach offers no clear advantage. However, if inclusion body formation could be minimized by altering growth and induction conditions, it is possible that the enzyme could be purified directly from the culture medium.

Example 5

Fed Batch Fermentation for the Production of HAL from a Bacterium from the Family Corynebacteriaceae Fermentation of pHUT200 in BL21λ21(DE3)pLysS is performed at 30° C. in the following media: Base media—20 g/L yeast extract and 1.67 g/L $(NH_4)_2SO_4$, supplemented with 17.2 ml of 1 M $KH_2PO_4$, 36.7 ml of 1 M $K_2HPO_4$, 1 ml/L of 2% $CaCl_2.H_2O$, 1 ml/L of 10% thiamine-HCl, 10 ml/L of Trace Metal Solution (6 g/liter Fe(III)Citrate, 1.5 g/L $MnCl_2.H_2O$, 0.8 g/L $Zn(CH_3COO)_2.2H_2O$, 0.3 g/L $H_3BO_3$, 0.25 g/L $Na_2MoO_4.2H_2O$, 0.25 g/L $CoCl_2.6H_2O$, 0.15 g/L $CuCl_2.2H_2O$, 0.84 g/L EDTA), 10 ml/L of 20% $MgSO_4.7H_2O$, and 10 ml/L of 50% glucose. Bring to final volume of 1 Liter with $ddH_2O$. When pH increases by 0.01 the feed media is initiated. The feed media is as follows: 1.5 g/L $(NH_4)_2SO_4$, 274 g/L yeast extract, 7.5 ml/L $MgSO_4.7H_2O$, and 400 ml 50% glucose. The feed was stopped when the pH decreased by 0.01. Thus, pH was maintained by the feed control loop. The fermentation run is induced at $OD_{600}$=5.0 with 1 mM IPTG. The dissolved oxygen is maintained at 20%, and induction is continued for 4 hours. The final $OD_{600}$=32, and the yield is approximately 1 gram of HAL per liter. The amount of protein following different periods of induction is shown in the SDS-PAGE gel in FIG. 5.

Example 6

Purification of HAL from E. coli

A simple purification method involving two acetone precipitation steps and one Q-sepharose column. Following resuspension of the cell paste in one-tenth volume of 50 mM TRIS pH 8.0 the pellet is sonicated four times and centrifuged. An equal volume of acetone is added to the supernatant. The solution is then centrifuged at 14,000 rpm for 15 minutes. The supernatant is retained and an equal volume of acetone is again added and again centrifuged. Following the second acetone precipitation the pellet is resuspended in 50 mM TRIS pH 8.0. The resuspension is then loaded onto a Q-sepharose column (5 mg protein/ml Q-sepharose) in 20 mM TRIS pH 8.0. The column is then washed with 20 mM TRIS pH 8.0 with 0.1 M KCl. Elution is performed with a 200 ml gradient from 0.1 M to 0.6 M KCl at a flow rate of 1 ml/min. Phenyl sepharose can then be used to further purify the enzyme. An example of purification via this scheme is depicted in FIG. 6.

Several potential alternate methods of purification have also been used successfully. HAL is resistant to heating at 70° C. Thus, heating and centrifugation can be used to remove precipitated contaminant proteins. Additionally, HAL does not precipitate with the addition of ammonium sulfate to 30% saturation. Therefore, addition of 30% ammonium sulfate and centrifugation can also be used to remove contaminant proteins. This precipitation can then be followed by purification via a phenyl sepharose column.

Example 7

Recovery of HAL from Inclusion Bodies

The pellet obtained from the sonicate of EXAMPLE 6 was washed in 100 mM sodium phosphate, pH6 containing 0.5% Triton X-100 by trituration. The washed inclusion bodies were collected by centrifugation at 4° C. in an SS34 rotor at 10 000 rpm for 10 minutes. This was repeated twice more, resulting in purified inclusion bodies.

A small amount of this material was solubilized in 50 mM Tris, pH8 with 8 M urea. Two hundred micrograms of this material was bound to 0.5 ml of DEAE—sephadex equilibrated in the same buffer. The resin was collected by centrifugation and eluted with 1 ml of 50 mMTris, pH8 with 0.5 M NaCl. This material was directly assayed for histidine ammonia lyase activity. A typical recovery yielded approximately 1–5% of the total histidine ammonia lyase in the active conformation.

Example 8

Characterization of HAL

Purified HAL has been determined to have approximately 40 I.U./mg of activity at 37° C. The temperature optimum was found to be 45° C. (FIG. 7). The graph shows that the enzyme maintains a significant level of activity at physiological temperature conditions. The activity profile of HAL at various pH is depicted in FIG. 8. The enzyme is active over a wide range of pH, with highest activity around pH 8.2 and high activity in physiological conditions.

Both reduced glutathione and DTT caused inhibition of HAL, but the inhibition was not complete. Both compounds were required at 15 mM concentrations to reduce the activity by half. EDTA was found to completely inhibit the reaction in concentrations as low as 1 mM. This inhibition was reversible with the presence of $Mn^{2+}$ at $1\times10^5$ M concentration.

Histidine ammonia lyase produced in E. coli was purified to near homogeneity as detailed above. Female mice weighing 18–22 grams were injected intraperitoneally with 1500 IU/kg body weight. HAL activity was monitored by assaying plasma obtained via retro-orbital bleeding two and ten hours following injection. These experiments using the recombinant enzyme showed an in vivo half-life of approximately 3 hours.

Example 9

Comparison of HAL to Other Histidine Ammonia Lyases

HAL has a significant advantage over other histidine ammonia lyases in that it is relatively resistant to inhibition by L-histidinol. L-histidinol is a histidine analog. Because L-histidinol acts as a competitive inhibitor it must be present in high concentrations to have an effect on histidine dependent reactions. Using HAL to reduce the overall histidine pool would therefore greatly increase the effectiveness of L-histidinol. However, brother histidine ammonia lyase enzymes have been shown to be strongly inhibited by L-histidinol. Because the Corynebacteriaceae histidine ammonia lyase (HAL) is not inhibited by L-histidinol at therapeutic L-histidinol levels it has a great advantage over other histidine ammonia lyases. Histidine ammonia lyase isolated from *Achromobacter liquidum* and *Streptomyces griseus* have been shown to be inhibited by L-histidinol and L-histidinol phosphate respectively with a Ki of 4.58 and 0.27 mM (Shibatani, T. et al. 1975; Wu, P. C. et al. 1995). Enzyme kinetic studies in our laboratory using *Streptomyces griseus* histidine ammonia lyase, showed that L-histidinol was able to completely inhibit the enzyme even at equal molar concentration to histidine. However, with HAL 20% of activity still is retained when L-histidinol is present at 10 times the concentration of L-histidine. We demonstrated the Ki of L-histidinol for HAL to be 24.3 to 33.4 mM.

Example 10

Extension of Half-life and Prevention of Antibody Formation to HAL Using PEGylation A PEGylation strategy has been developed using BTC-PEG 5000 (Shearwater Polymers, Inc.). HAL is reconstituted in 50 mM sodium phosphate buffer pH 8.0 and dialyzed against that same buffer. Dialysis is continued for three hours. Following dialysis the protein concentration is adjusted to 5 mg/ml. BTC-PEG is added in a ratio of 1:10 and incubated for one hour at RT after dissolving the BTC-PEG. The solution is then dialyzed against 50 mM sodium phosphate pH 7.5 to remove unbound PEG. The extent of PEGylation is then determined by using a fluorescamine assay. Different ratios of PEG to enzyme were tested to determine the % PEGylation each ratio would yield. Repeated fluorescamine assays showed that 1:10 PEGylation with BTC-PEG provided about 40–45% PEGylation protection of the enzyme.

When HAL was injected into mice, the bioactive half-life was determined to be less than four hours. To determine the half-life of the enzyme a known amount of units of enzyme is injected intraperitonially into several mice. Blood is then drawn retro-orbitally from different mice at 4-hour intervals. The blood is then centrifuged and serum is used to perform the histidine ammonia lyase assay as previously described. The half-life is then determined by comparing the time at which units/ml in serum is half of its value following the first four hour time-point.

A 30 Unit HAL intraperitonial injection yielded only 3 Units of active HAL in the blood following four hours and the half-life was found to be less than one hour. HAL was then PEGylated using BTC-PEG. This increased the half-life of the enzyme in the blood to more than 48 hours. The PEGylation of the enzyme also affords it protection against antibody-mediated depletion in the host. UnPEGylated protein will elicit an antibody response that will clear the enzyme from the blood following one week of treatment. The antibody response is greatly delayed in mice receiving PEGylated HAL. In three out of five mice active enzyme was still being recovered following 79 days of treatment and following 119 days in 2 of the five mice.

We have also used a higher molecular weight PEG, BTC 20,000, as well as other PEGs to successfully modify HAL.

Example 11

Anti-viral Activity of HAL

HAL was tested for its anti-viral activity against a variety of infectious viruses in vitro. Effectiveness against Herpes Simplex Virus (HSV) was assayed using the following method. Confluent VERO cells from a T-175 flask are tyrpsinized and split into as many T-25 flasks as the experiment requires. The cells are grown in RPMI-1640 with 10% newborn calf serum-heat inactivated, and L-glutamine. After cells have grown to confluence remove the media and add 0.5 ml of diluted virus (make a series of 1:5 dilution). Dilution of virus is prepared in RPMI-1640 with 2% NCS. The cells are then incubated for 1 hour at 37° C. and then 5 ml of RPMI-1640 with 2% NCS with or without the test compounds is added and incubation is allowed to continue for 1 day. After 24 hours the flasks are sealed with parafilm and frozen at −70° C. The cells are then allowed to thaw at RT to lyse dead intact cells, releasing virus. The viral suspension is then centrifuged to remove cell debris. The viral dilution that caused complete lysis will be used in the plaque assay. The plaque assay is set up by trypsinizing cells from a T-75 and resuspending the cells in RPMI-1640 with 10% NCS and poured into 6-well plate at 2 ml/well. The cells are incubated overnight at 37° C. The media is then removed by suction and 0.2 ml of the viral dilution is added and allowed to incubate for one hour. During this hour the agar is prepared and stored at 41° C. to prevent hardening. The agar concentrations are as follows: ½ vol. 2×BME (Gibco), 2% Pen/Strep, 2% NCS, and 1% agar. After the hour incubation 2 ml of the BME/agar is carefully added to the wells, so as not to disturb the cell monolayer. The plate is left at RT for twenty to thirty minutes to allow the agar to harden, and then the cells are incubated for 48 hours at 37° C. The cells are then stained used BME/agar containing neutral red. The BME/agar is prepared as before with the addition of neutral red stain (Gibco) to a final concentration of 5%. 2 ml of this agar is added and allowed to harden before 24 hour incubation at 37° C. Plaques are then counted and the cells fixed for a permanent record.

One positive experimental result has been seen against HSV. Herpes Simplex Viruses are double-stranded DNA viruses belonging to the family Herpesviridae. Several viruses in this group, including Herpes Simplex Virus Type 1, Herpes Simplex Virus Type 2, Varicella-Zoster Virus, Epstein-Barr Virus, and Cytomegalo Virus cause serious and often fatal infections in human beings. Results of the experiments using HSV have indicated that HAL does inhibit HSV replication and that when given in conjunction with L-histidinol even significantly greater inhibition is observed. Use of HAL alone in a concentration of 0.005 U/ml resulted in a reduction in plaque forming units of approximately 200 fold versus control. Use of 0.01 U/ml HAL resulted in over 1,000-fold decrease in plaque forming units/ml. However, when given in conjunction with L-histidinol the effect is greatly enhanced and the concentration of both compounds can be significantly lowered while inhibition is increased. When L-histidinol is given at 0.1 and 0.5 mM concentrations no inhibition is observed, and only 5-fold inhibition is observed at 1 mM. However, when 0.5 mM L-histidinol is given in combination with 0.003 U/ml HAL the inhibition is near 100% (less than 500 PFU versus $1.25 \times 10^8$ in control). These results are shown in FIG. 9.

Another successful study has been with Respiratory Syncytial Virus (RSV). RSV is another highly infectious disease causing agent. It causes lower respiratory-tract infections such as bronchitis and pneumonia in infancy and early childhood, with nearly 50% of infants suffering from an RSV infection during their first winter. Experiments were performed in tissue culture using the RSV Plaque Assay. The RSV plaque assay is performed similarly to the HSV assay. When performing the RSV assay Hep2 cells are used to propagate the RSV and the cells are grown in EMEM media with 2% FBS, L-glutamine and Antibiotic-Antimycotic. The virus stock is diluted in the medium and added to each well with or without the desired testing compound. The plates are incubated for 2 hours at 37° C. and the virus is removed. 0.5% agarose is added to the media and incubated for 5 days at 37° C. The plates are then fixed with 10% formalin and stained with crystal violet. When HAL and L-histidinol were present in 0.005 U/ml and 3 mM respectively, no inhibition of RSV plaque numbers is seen, as is shown in FIG. 11. However, when these same concentrations were used in combination the resulting plaque assay showed no higher than background levels of plaques. These results indicate the strong synergy that exists with these two drugs and provides promise for HAL as an effective antiviral therapy.

Use of HAL in combination with L-histidinol is thus shown to greatly reduce the therapeutic index of both drugs. This makes effective treatment of these highly infectious diseases with low toxicity a good possibility.

Figure 12:
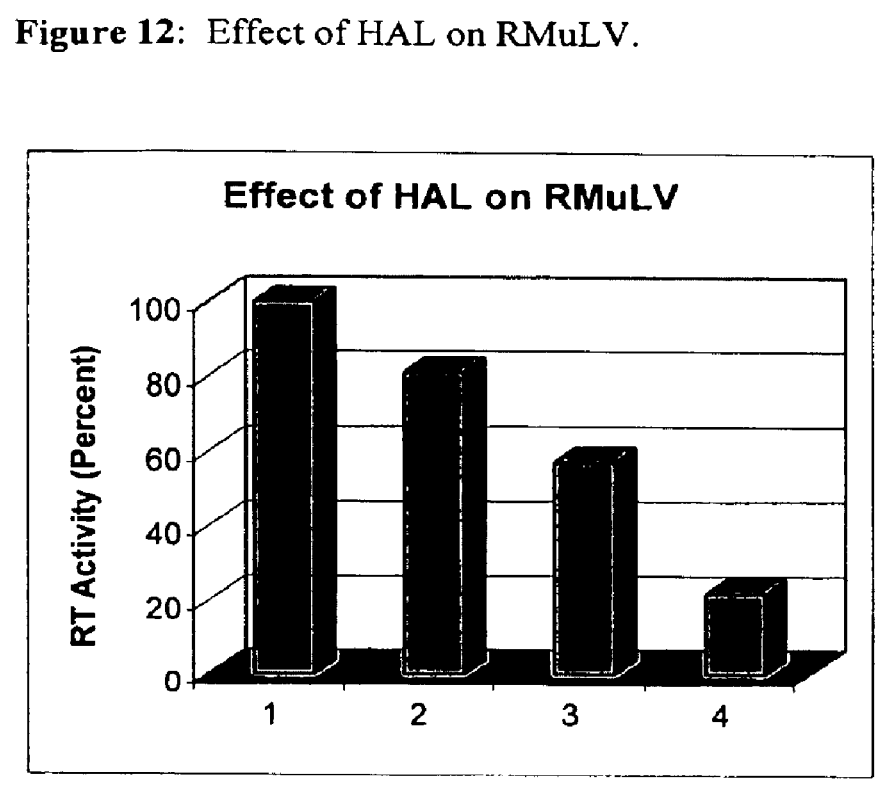

Rauscher Murine Leukemia Virus (RMuLV) belongs to the family retroviradae, the group of viruses that also includes the Human Immunodeficiency Virus (HIV). We have used RMuLV as a model for drug development against HIV. In these studies we use mouse SC-1 cells persistently infected with RMuLV to test the effect of HAL against virus replication. Briefly, the cells are plated on a 96-well plate in RPMI medium containing 10% Fetal Calf Serum and glutamine. After 24 hours of growth, the cells are treated with various test compounds for 24 hours. The supernatant is then tested for reverse transcriptase activity as described in Roberts, J. and W. G. McGregor (Roberts, J. and W. G. McGregor. 1991. *J. General Virology*. 72: 299–305). Results depicted in FIG. 12 show that HAL given at 0.004 U/ml inhibits reverse transcription by over 70%.

Example 12

Effectiveness of HAL as an Anticancer Agent

We have used a sensitive in vitro cancer drug screening assay to study the effect of HAL on various tumor cell lines. Briefly, each cell line is inoculated into microtiter plates, and pre-incubated for 24 hours at 37° C. Subsequently, the test agents are added and the culture is incubated for an additional 48 hours at 37° C. End-point determination of cell growth is performed by in situ fixation of cells, followed by staining with a protein-binding dye, sulforchodamine B (SRB) (Monks, A., Scudiero, D. Skehan, P., Shoemaker, R., Paull, L., Vistica, D., Hose, C., Langley, J., Cronise, P., Vaigro-Wolff, A. et al. 1991. *Journal of National Cancer Institute*. 83(11): 757–766). Two human prostate cancer cell lines, LNCaP and PC-3, were tested using this assay. We found the growth of human prostate cancer cell line LNCaP was inhibited by 69% by 0.005 U/ml HAL, and PC-3 is inhibited by 81% by 0.01 U/ml HAL In addition to prostate cancer, three cell lines of human ovarian cancer were tested. The growth of ovarian cancer cell lines SKOV-3 and MA148 were inhibited by 78% and 95% respectively by 0.01 U/ml HAL, and OVCA3 is inhibited by 53% with 0.005 U/ml HAL. In addition to the prostate and ovarian cancer cell lines C6 glioblastoma cells were tested and HAL was found to inhibit growth by 95% at a concentration of 0.01 U/ml.

The results of this widely accepted assay are very encouraging. Clearly, HAL is very effective in controlling the growth of a wide variety of human tumors in vitro and is potentially an effectively anticancer therapeutic.

What is claimed is:

1. A method of treating a viral infection, comprising administering to a patient suffering from the viral infection a therapeutic amount of a polypeptide having histidine ammonia lyase activity.

2. The method according to claim 1, wherein the histidine ammonia lyase activity is about 40 IU/mg protein and the polypeptide corresponds in sequence to histidine ammonia lyase of Corynebacteriaceae.

3. The method according to claim 1, wherein the histidine ammonia lyase activity is not substantially decreased in the presence of L-histidinol or a therapeutic salt thereof.

4. The method according to claim 3, further comprising administering a therapeutic amount of L-histidinol or a therapeutic salt thereof.

5. The method according to claim 1, wherein the viral infection is caused by a virus is selected from the group consisting of Herpes Virus Type 1, Herpes Simplex Virus Type 2, Varicella-Zoster Virus, Epstein-Barr virus, Cytomegalovirus, Respiratory Syncytial Virus, and Human Immunodeficiency Virus.

6. The method according to claim 1, wherein the polypeptide is selected from the group consisting of SEQ ID NOS: 1–5, 8–10, and 12.

7. The method according to claim 1, wherein the polypeptide comprises conservative substitutions relative to the sequence of histidine ammonia lyase of Corynebacteriaceae and wherein the polypeptide maintains the histidine ammonia lyase activity.

8. The method according to claim 7, wherein the polypeptide comprises SEQ ID NOS: 6 or 11, wherein each amino acid represented by an "X" is substituted with an amino acid from the corresponding position of the histidine ammonia lyase selected from the group consisting of Corynebacteriaceae, *Streptomyces coelicolor, Agrobacterium rhizogenes, Vibrio cholerae, Pseudomonas aeruginosa, Bacillus halodurans, Pseudomonas aeruginosa, Thermoplasma acidophilum, Mus musculus*, rat, uncultured bacterium pCosAS1, *Rhizobium meiloti*, and *Halobacterium* sp and wherein at least one of the amino acids represented by an "X" is not substituted with an amino acid from the corresponding position of the histidine ammonia lyase of Corynebacteriaceae.

9. A method for treating a patient suffering from a cancer, comprising administering to the patient suffering from said cancer a therapeutic amount of a polypeptide having about 40 IU/mg protein of histidine ammonia lyase activity, wherein said histidine ammonia lyase activity is not substantially decreased in the presence of L-histidinol or a therapeutic salt thereof and the polypeptide corresponds in sequence to histidine ammonia lyase of Corynebacteriaceae, and a therapeutic amount of L-histidinol or a therapeutic salt thereof.

10. The method according to claim 9, wherein the polypeptide is selected from the group consisting of SEQ ID NOS: 1–5, 8–10, and 12.

11. The method according to claim 9, wherein the polypeptide comprises conservative substitutions relative to the sequence of histidine ammonia lyase of Corynebacteriaceae and wherein the polypeptide maintains the histidine ammonia lyase activity.

12. The method according to claim 11, wherein the polypeptide comprises SEQ ID NOS: 6 or 11, wherein each amino acid represented by an "X" is substituted with an amino acid from the corresponding position of the histidine ammonia lyase selected consisting of Corynebacteriaceae, *Streptomyces coelicolor, Agrobacterium rhizogenes, Vibrio cholerae, Pseudomonas aeruginosa, Bacillus halodurans, Pseudomonas aeruginosa, Thermoplasma acidophilum, Mus musculus*, rat, uncultured bacterium pCosAS1, *Rhizobium meiloti*, and *Halobacterium* sp and wherein at least one of the amino acids represented by an "X" is not substituted with an amino acid from the corresponding position of the histidine ammonia lyase of Corynebacteriaceae.

13. A method for reducing toxicity to normal cells from chemotherapeutic agents, comprising
   (i) administering to a patient a therapeutically effective amount of a polypeptide having histidine ammonia lyase activity, and
   (ii) additionally administering to said patient a therapeutically effective amount of a chemotherapeutic agent, whereby said polypeptide having histidine ammonia lyase activity selectively depletes circulating histidine and causes growth arrest in normal cells, without affecting the growth of tumor cells.

14. The method according to claim 13, wherein upon the administration of said polypeptide, non-diseased cells of said patient enter a reversible quiescent state.

15. The method according to claim 13, wherein the polypeptide is a modified polypeptide that comprises polyethylene glycol.

16. A method for delivering an immunosuppressant to a patient, comprising: administering to a patient a therapeutically effective amount of a polypeptide having histidine ammonia lyase activity, wherein said polypeptide is PEGylated and wherein said polypeptide generates trans-urocanic acid (t-UA) in vivo; and subjecting the patient to an irradiating agent, wherein said irradiating agent causes the photoisomerization of t-UA to its cis isomer (c-UA), and wherein said cis isomer comprises an immunosuppressive property.

17. The method according to claim 16, wherein the irradiating agent is UVB irradiation, and wherein the polypeptide comprises polyethylene glycol.

18. The method according to claim 17, wherein the patient has an immune system disorder.

19. The method according to claim 18, wherein the UVB radiation is localized.

20. The method according to claim 16, further comprising administering to the patient a transplanted organ.

21. A method of treating a viral infection comprising administering to a patient suffering from the viral infection a therapeutic amount of a histidine analog and a polypeptide having histidine ammonia lyase activity.

* * * * *

SEQUENCE LISTING

```
<160> NUMBER OF SEQ ID NOS: 66

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Asn Ala Gly Ile Thr Pro Val Val Arg Glu Tyr Gly Ser Leu Gly
 1               5                  10                  15

Cys Ser Gly Asp Leu Ala Pro Leu Ser His Cys Ala Leu Val Leu Met
            20                  25                  30

Gly Glu Gly Glu Ala
        35

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Gly Met Leu Asn Ala Gly Ile Thr Pro Val Val Arg Glu Tyr Gly Ser
 1               5                  10                  15

Leu Gly Cys Ser Gly Asp Leu Ala Pro Leu Ser His Cys Ala Leu Val
                20                  25                  30

Leu Met Gly Glu Gly Glu Ala Thr
            35                  40

<210> SEQ ID NO 3
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Ser Ala Pro Gln Ile Thr Leu Gly Leu Ser Gly Ala Thr Ala
 1               5                  10                  15

Asp Asp Val Ile Ala Val Ala Arg His Glu Ala Arg Ile Ser Ile Ser
                20                  25                  30

Pro Gln Val Leu Glu Glu Leu Ala Ser Val Arg Ala His Ile Asp Ala
            35                  40                  45

Leu Ala Ser Ala Asp Thr Pro Val Tyr Gly Ile Ser Thr Gly Phe Gly
        50                  55                  60

Ala Leu Ala Thr Arg His Ile Ala Pro Glu Asp Arg Ala Lys Leu Gln
65                  70                  75                  80

Arg Ser Leu Ile Arg Ser His Ala Ala Gly Met Gly Glu Pro Val Glu
                85                  90                  95

Arg Glu Val Val Arg Ala Leu Met Phe Leu Arg Ala Lys Thr Leu Ala
            100                 105                 110

Ser Gly Arg Thr Gly Val Arg Pro Val Val Leu Glu Thr Met Val Gly
        115                 120                 125

Met Leu Asn Ala Gly Ile Thr Pro Val Val Arg Glu Tyr Gly Ser Leu
130                 135                 140

Gly Cys Ser Gly Asp Leu Ala Pro Leu Ser His Cys Ala Leu Val Leu
145                 150                 155                 160

Met Gly Glu Gly Glu Ala Thr Asp Ala His Gly Asp Ile Arg Pro Val
                165                 170                 175

Pro Glu Leu Phe Ala Glu Ala Gly Leu Thr Pro Val Glu Leu Ala Glu
            180                 185                 190

Lys Glu Gly Leu Ala Leu Val Asn Gly Thr Asp Gly Met Leu Gly Gln
        195                 200                 205

Leu Ile Met Ala Leu Ala Asp Leu Asp Glu Leu Leu Asp Ile Ala Asp
    210                 215                 220

Ala Thr Ala Ala Met Ser Val Glu Ala Gln Leu Gly Thr Asp Gln Val
225                 230                 235                 240

Phe Arg Ala Glu Leu His Glu Pro Leu Arg Pro His Pro Gly Gln Gly
                245                 250                 255

Arg Ser Ala Gln Asn Met Phe Ala Phe Leu Ala Asp Ser Pro Ile Val
            260                 265                 270

Ala Ser His Arg Glu Gly Asp Gly Arg Val Gln Asp Ala Tyr Ser
        275                 280                 285

<210> SEQ ID NO 4
```

<211> LENGTH: 405
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Ala Ser Ala Pro Gln Ile Thr Leu Gly Leu Ser Gly Ala Thr Ala
 1               5                  10                  15

Asp Asp Val Ile Ala Val Ala Arg His Glu Ala Arg Ile Ser Ile Ser
             20                  25                  30

Pro Gln Val Leu Glu Glu Leu Ala Ser Val Arg Ala His Ile Asp Ala
         35                  40                  45

Leu Ala Ser Ala Asp Thr Pro Val Tyr Gly Ile Ser Thr Gly Phe Gly
     50                  55                  60

Ala Leu Ala Thr Arg His Ile Ala Pro Glu Asp Arg Ala Lys Leu Gln
 65                  70                  75                  80

Arg Ser Leu Ile Arg Ser His Ala Ala Gly Met Gly Glu Pro Val Glu
                 85                  90                  95

Arg Glu Val Val Arg Ala Leu Met Phe Leu Arg Ala Lys Thr Leu Ala
            100                 105                 110

Ser Gly Arg Thr Gly Val Arg Pro Val Val Leu Glu Thr Met Val Gly
        115                 120                 125

Met Leu Asn Ala Gly Ile Thr Pro Val Val Arg Glu Tyr Gly Ser Leu
130                 135                 140

Gly Cys Ser Gly Asp Leu Ala Pro Leu Ser His Cys Ala Leu Val Leu
145                 150                 155                 160

Met Gly Glu Gly Glu Ala Thr Asp Ala His Gly Asp Ile Arg Pro Val
                165                 170                 175

Pro Glu Leu Phe Ala Glu Ala Gly Leu Thr Pro Val Glu Leu Ala Glu
            180                 185                 190

Lys Glu Gly Leu Ala Leu Val Asn Gly Thr Asp Gly Met Leu Gly Gln
        195                 200                 205

Leu Ile Met Ala Leu Ala Asp Leu Asp Glu Leu Leu Asp Ile Ala Asp
210                 215                 220

Ala Thr Ala Ala Met Ser Val Glu Ala Gln Leu Gly Thr Asp Gln Val
225                 230                 235                 240

Phe Arg Ala Glu Leu His Glu Pro Leu Arg Pro His Pro Gly Gln Gly
                245                 250                 255

Arg Ser Ala Gln Asn Met Phe Ala Phe Leu Ala Asp Ser Pro Ile Val
            260                 265                 270

Ala Ser His Arg Glu Gly Asp Gly Arg Val Gln Asp Ala Tyr Ser Leu
        275                 280                 285

Arg Cys Ser Pro Gln Val Thr Gly Ala Ala Arg Asp Thr Ile Ala His
290                 295                 300

Ala Arg Leu Val Ala Thr Arg Glu Leu Ala Ala Ile Asp Asn Pro
305                 310                 315                 320

Val Val Leu Pro Ser Gly Glu Val Thr Ser Asn Gly Asn Phe His Gly
                325                 330                 335

Ala Pro Val Ala Tyr Val Leu Asp Phe Leu Ala Ile Ala Val Ala Asp
            340                 345                 350

Leu Gly Ser Ile Ala Glu Arg Arg Thr Asp Arg Met Leu Asp Pro Ala
        355                 360                 365

Arg Ser Arg Asp Leu Pro Ala Phe Leu Ala Asp Asp Pro Gly Val Asp
```

-continued

```
                      370                 375                 380
Ser Gly Met Met Ile Ala Gln Tyr Thr Gln Ala Gly Leu Val Ala Glu
385                 390                 395                 400

Asn Lys Arg Leu Ala
            405

<210> SEQ ID NO 5
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ser Ala Pro Gln Ile Thr Leu Gly Leu Ser Gly Ala Thr Ala
  1               5                  10                  15

Asp Asp Val Ile Ala Val Ala Arg His Glu Ala Arg Ile Ser Ile Ser
                 20                  25                  30

Pro Gln Val Leu Glu Glu Leu Ala Ser Val Arg Ala His Ile Asp Ala
             35                  40                  45

Leu Ala Ser Ala Asp Thr Pro Val Tyr Gly Ile Ser Thr Gly Phe Gly
 50                  55                  60

Ala Leu Ala Thr Arg His Ile Ala Pro Glu Asp Arg Ala Lys Leu Gln
 65                  70                  75                  80

Arg Ser Leu Ile Arg Ser His Ala Ala Gly Met Gly Glu Pro Val Glu
                 85                  90                  95

Arg Glu Val Val Arg Ala Leu Met Phe Leu Arg Ala Lys Thr Leu Ala
            100                 105                 110

Ser Gly Arg Thr Gly Val Arg Pro Val Val Leu Glu Thr Met Val Gly
            115                 120                 125

Met Leu Asn Ala Gly Ile Thr Pro Val Val Arg Glu Tyr Gly Ser Leu
130                 135                 140

Gly Cys Ser Gly Asp Leu Ala Pro Leu Ser His Cys Ala Leu Val Leu
145                 150                 155                 160

Met Gly Glu Gly Glu Ala Thr Asp Ala His Gly Asp Ile Arg Pro Val
                165                 170                 175

Pro Glu Leu Phe Ala Glu Ala Gly Leu Thr Pro Val Glu Leu Ala Glu
            180                 185                 190

Lys Glu Gly Leu Ala Leu Val Asn Gly Thr Asp Gly Met Leu Gly Gln
            195                 200                 205

Leu Ile Met Ala Leu Ala Asp Leu Asp Glu Leu Leu Asp Ile Ala Asp
210                 215                 220

Ala Thr Ala Ala Met Ser Val Glu Ala Gln Leu Gly Thr Asp Gln Val
225                 230                 235                 240

Phe Arg Ala Glu Leu His Glu Pro Leu Arg Pro His Pro Gly Gln Gly
                245                 250                 255

Arg Ser Ala Gln Asn Met Phe Ala Phe Leu Ala Asp Ser Pro Ile Val
            260                 265                 270

Ala Ser His Arg Glu Gly Asp Gly Arg Val Gln Asp Ala Tyr Ser Leu
            275                 280                 285

Arg Cys Ser Pro Gln Val Thr Gly Ala Ala Arg Asp Thr Ile Ala His
290                 295                 300

Ala Arg Leu Val Ala Thr Arg Glu Leu Ala Ala Ala Ile Asp Asn Pro
305                 310                 315                 320
```

```
Val Val Leu Pro Ser Gly Glu Val Thr Ser Asn Gly Asn Phe His Gly
                325                 330                 335

Ala Pro Val Ala Tyr Val Leu Asp Phe Leu Ala Ile Ala Val Ala Asp
                340                 345                 350

Leu Gly Ser Ile Ala Glu Arg Arg Thr Asp Arg Met Leu Asp Pro Ala
                355                 360                 365

Arg Ser Arg Asp Leu Pro Ala Phe Leu Ala Asp Pro Gly Val Asp
        370                 375                 380

Ser Gly Met Met Ile Ala Gln Tyr Thr Gln Ala Gly Leu Val Ala Glu
385                 390                 395                 400

Asn Lys Arg Leu Ala Val Pro Ala Ser Val Asp Ser Ile Pro Ser Ser
                405                 410                 415

Ala Met Gln Glu Asp His Val Ser Leu Gly Trp His Ala Ala Arg Lys
                420                 425                 430

Leu Arg Thr Ser Val Ala Asn Leu Arg Arg Ile Leu Ala Val Glu Met
                435                 440                 445

Leu Ile Ala Gly Arg Ala Leu Asp Leu Arg Ala Pro Leu Lys Pro Gly
        450                 455                 460

Pro Ala Thr Gly Ala Val Leu Glu Val Leu Arg Ser Lys Val Ala Gly
465                 470                 475                 480

Pro Gly Gln Asp Arg Phe Leu Ser Ala Glu Leu Glu Ala Ala Tyr Asp
                485                 490                 495

Leu Leu Ala Asn Gly Ser Val His Lys Ala Leu Glu Ala His Leu Pro
                500                 505                 510
Ala

<210> SEQ ID NO 6
<211> LENGTH: 511
<212> TYPE: PRT
<213> ORGANISM: Artificial Sequence
<220> FEATURE:
<223> OTHER INFORMATION: Description of Artificial Sequence: Formula
      polypeptide
<221> NAME/KEY: MOD_RES
<222> LOCATION: (1)..(9)
<223> OTHER INFORMATION: Variable amino acid
<221> NAME/KEY: MOD_RES
<222> LOCATION: (11)
<223> OTHER INFORMATION: Variable amino acid
<221> NAME/KEY: MOD_RES
<222> LOCATION: (14)
<223> OTHER INFORMATION: Variable amino acid
<221> NAME/KEY: MOD_RES
<222> LOCATION: (17)
<223> OTHER INFORMATION: Variable amino acid
<221> NAME/KEY: MOD_RES
<222> LOCATION: (20)
<223> OTHER INFORMATION: Variable amino acid
<221> NAME/KEY: MOD_RES
<222> LOCATION: (26)
<223> OTHER INFORMATION: Variable amino acid
<221> NAME/KEY: MOD_RES
<222> LOCATION: (29)..(31)
<223> OTHER INFORMATION: Variable amino acid
<221> NAME/KEY: MOD_RES
<222> LOCATION: (33)..(36)
<223> OTHER INFORMATION: Variable amino acid
<221> NAME/KEY: MOD_RES
<222> LOCATION: (38)
<223> OTHER INFORMATION: Variable amino acid
<221> NAME/KEY: MOD_RES
<222> LOCATION: (41)..(42)
<223> OTHER INFORMATION: Variable amino acid
<221> NAME/KEY: MOD_RES
<222> LOCATION: (44)..(46)
<223> OTHER INFORMATION: Variable amino acid
<221> NAME/KEY: MOD_RES
```

```
<222> LOCATION: (51)..(54)
<223> OTHER INFORMATION: Variable amino acid
<221> NAME/KEY: MOD_RES
<222> LOCATION: (59)
<223> OTHER INFORMATION: Variable amino acid
<221> NAME/KEY: MOD_RES
<222> LOCATION: (68)
<223> OTHER INFORMATION: Variable amino acid
<221> NAME/KEY: MOD_RES
<222> LOCATION: (72)..(73)
<223> OTHER INFORMATION: Variable amino acid
<221> NAME/KEY: MOD_RES
<222> LOCATION: (75)
<223> OTHER INFORMATION: Variable amino acid
<221> NAME/KEY: MOD_RES
<222> LOCATION: (78)
<223> OTHER INFORMATION: Variable amino acid
<221> NAME/KEY: MOD_RES
<222> LOCATION: (82)..(84)
<223> OTHER INFORMATION: Variable amino acid
<221> NAME/KEY: MOD_RES
<222> LOCATION: (93)..(94)
<223> OTHER INFORMATION: Variable amino acid
<221> NAME/KEY: MOD_RES
<222> LOCATION: (108)
<223> OTHER INFORMATION: Variable amino acid
<221> NAME/KEY: MOD_RES
<222> LOCATION: (111)
<223> OTHER INFORMATION: Variable amino acid
<221> NAME/KEY: MOD_RES
<222> LOCATION: (115)
<223> OTHER INFORMATION: Variable amino acid
<221> NAME/KEY: MOD_RES
<222> LOCATION: (121)
<223> OTHER INFORMATION: Variable amino acid
<221> NAME/KEY: MOD_RES
<222> LOCATION: (123)..(124)
<223> OTHER INFORMATION: Variable amino acid
<221> NAME/KEY: MOD_RES
<222> LOCATION: (127)
<223> OTHER INFORMATION: Variable amino acid
<221> NAME/KEY: MOD_RES
<222> LOCATION: (129)
<223> OTHER INFORMATION: Variable amino acid
<221> NAME/KEY: MOD_RES
<222> LOCATION: (139)
<223> OTHER INFORMATION: Variable amino acid
<221> NAME/KEY: MOD_RES
<222> LOCATION: (159)
<223> OTHER INFORMATION: Variable amino acid
<221> NAME/KEY: MOD_RES
<222> LOCATION: (168)..(170)
<223> OTHER INFORMATION: Variable amino acid
<221> NAME/KEY: MOD_RES
<222> LOCATION: (172)..(173)
<223> OTHER INFORMATION: Variable amino acid
<221> NAME/KEY: MOD_RES
<222> LOCATION: (176)..(177)
<223> OTHER INFORMATION: Variable amino acid
<221> NAME/KEY: MOD_RES
<222> LOCATION: (180)
<223> OTHER INFORMATION: Variable amino acid
<221> NAME/KEY: MOD_RES
<222> LOCATION: (182)..(183)
<223> OTHER INFORMATION: Variable amino acid
<221> NAME/KEY: MOD_RES
<222> LOCATION: (185)..(186)
<223> OTHER INFORMATION: Variable amino acid
<221> NAME/KEY: MOD_RES
<222> LOCATION: (191)
<223> OTHER INFORMATION: Variable amino acid
<221> NAME/KEY: MOD_RES
<222> LOCATION: (199)
<223> OTHER INFORMATION: Variable amino acid
<221> NAME/KEY: MOD_RES
<222> LOCATION: (208)
<223> OTHER INFORMATION: Variable amino acid
<221> NAME/KEY: MOD_RES
<222> LOCATION: (210)
```

```
<223> OTHER INFORMATION: Variable amino acid
<221> NAME/KEY: MOD_RES
<222> LOCATION: (217)..(218)
<223> OTHER INFORMATION: Variable amino acid
<221> NAME/KEY: MOD_RES
<222> LOCATION: (220)..(222)
<223> OTHER INFORMATION: Variable amino acid
<221> NAME/KEY: MOD_RES
<222> LOCATION: (225)
<223> OTHER INFORMATION: Variable amino acid
<221> NAME/KEY: MOD_RES
<222> LOCATION: (229)
<223> OTHER INFORMATION: Variable amino acid
<221> NAME/KEY: MOD_RES
<222> LOCATION: (231)
<223> OTHER INFORMATION: Variable amino acid
<221> NAME/KEY: MOD_RES
<222> LOCATION: (234)
<223> OTHER INFORMATION: Variable amino acid
<221> NAME/KEY: MOD_RES
<222> LOCATION: (239)
<223> OTHER INFORMATION: Variable amino acid
<221> NAME/KEY: MOD_RES
<222> LOCATION: (241)..(243)
<223> OTHER INFORMATION: Variable amino acid
<221> NAME/KEY: MOD_RES
<222> LOCATION: (247)..(249)
<223> OTHER INFORMATION: Variable amino acid
<221> NAME/KEY: MOD_RES
<222> LOCATION: (257)
<223> OTHER INFORMATION: Variable amino acid
<221> NAME/KEY: MOD_RES
<222> LOCATION: (260)
<223> OTHER INFORMATION: Variable amino acid
<221> NAME/KEY: MOD_RES
<222> LOCATION: (263)..(265)
<223> OTHER INFORMATION: Variable amino acid
<221> NAME/KEY: MOD_RES
<222> LOCATION: (268)
<223> OTHER INFORMATION: Variable amino acid
<221> NAME/KEY: MOD_RES
<222> LOCATION: (270)..(274)
<223> OTHER INFORMATION: Variable amino acid
<221> NAME/KEY: MOD_RES
<222> LOCATION: (276)..(280)
<223> OTHER INFORMATION: Variable amino acid
<221> NAME/KEY: MOD_RES
<222> LOCATION: (288)
<223> OTHER INFORMATION: Variable amino acid
<221> NAME/KEY: MOD_RES
<222> LOCATION: (291)
<223> OTHER INFORMATION: Variable amino acid
<221> NAME/KEY: MOD_RES
<222> LOCATION: (295)
<223> OTHER INFORMATION: Variable amino acid
<221> NAME/KEY: MOD_RES
<222> LOCATION: (298)
<223> OTHER INFORMATION: Variable amino acid
<221> NAME/KEY: MOD_RES
<222> LOCATION: (302)..(303)
<223> OTHER INFORMATION: Variable amino acid
<221> NAME/KEY: MOD_RES
<222> LOCATION: (306)
<223> OTHER INFORMATION: Variable amino acid
<221> NAME/KEY: MOD_RES
<222> LOCATION: (310)
<223> OTHER INFORMATION: Variable amino acid
<221> NAME/KEY: MOD_RES
<222> LOCATION: (315)..(317)
<223> OTHER INFORMATION: Variable amino acid
<221> NAME/KEY: MOD_RES
<222> LOCATION: (325)
<223> OTHER INFORMATION: Variable amino acid
<221> NAME/KEY: MOD_RES
<222> LOCATION: (327)
<223> OTHER INFORMATION: Variable amino acid
<221> NAME/KEY: MOD_RES
<222> LOCATION: (329)
<223> OTHER INFORMATION: Variable amino acid
```

```
<221> NAME/KEY: MOD_RES
<222> LOCATION: (349)..(350)
<223> OTHER INFORMATION: Variable amino acid
<221> NAME/KEY: MOD_RES
<222> LOCATION: (357)
<223> OTHER INFORMATION: Variable amino acid
<221> NAME/KEY: MOD_RES
<222> LOCATION: (364)
<223> OTHER INFORMATION: Variable amino acid
<221> NAME/KEY: MOD_RES
<222> LOCATION: (367)..(368)
<223> OTHER INFORMATION: Variable amino acid
<221> NAME/KEY: MOD_RES
<222> LOCATION: (371)..(372)
<223> OTHER INFORMATION: Variable amino acid
<221> NAME/KEY: MOD_RES
<222> LOCATION: (375)
<223> OTHER INFORMATION: Variable amino acid
<221> NAME/KEY: MOD_RES
<222> LOCATION: (381)
<223> OTHER INFORMATION: Variable amino acid
<221> NAME/KEY: MOD_RES
<222> LOCATION: (387)
<223> OTHER INFORMATION: Variable amino acid
<221> NAME/KEY: MOD_RES
<222> LOCATION: (396)
<223> OTHER INFORMATION: Variable amino acid
<221> NAME/KEY: MOD_RES
<222> LOCATION: (399)
<223> OTHER INFORMATION: Variable amino acid
<221> NAME/KEY: MOD_RES
<222> LOCATION: (401)
<223> OTHER INFORMATION: Variable amino acid
<221> NAME/KEY: MOD_RES
<222> LOCATION: (410)
<223> OTHER INFORMATION: Variable amino acid
<221> NAME/KEY: MOD_RES
<222> LOCATION: (425)
<223> OTHER INFORMATION: Variable amino acid
<221> NAME/KEY: MOD_RES
<222> LOCATION: (428)
<223> OTHER INFORMATION: Variable amino acid
<221> NAME/KEY: MOD_RES
<222> LOCATION: (436)
<223> OTHER INFORMATION: Variable amino acid
<221> NAME/KEY: MOD_RES
<222> LOCATION: (438)
<223> OTHER INFORMATION: Variable amino acid
<221> NAME/KEY: MOD_RES
<222> LOCATION: (441)
<223> OTHER INFORMATION: Variable amino acid
<221> NAME/KEY: MOD_RES
<222> LOCATION: (444)
<223> OTHER INFORMATION: Variable amino acid
<221> NAME/KEY: MOD_RES
<222> LOCATION: (448)..(450)
<223> OTHER INFORMATION: Variable amino acid
<221> NAME/KEY: MOD_RES
<222> LOCATION: (452)
<223> OTHER INFORMATION: Variable amino acid
<221> NAME/KEY: MOD_RES
<222> LOCATION: (455)..(456)
<223> OTHER INFORMATION: Variable amino acid
<221> NAME/KEY: MOD_RES
<222> LOCATION: (460)..(462)
<223> OTHER INFORMATION: Variable amino acid
<221> NAME/KEY: MOD_RES
<222> LOCATION: (464)
<223> OTHER INFORMATION: Variable amino acid
<221> NAME/KEY: MOD_RES
<222> LOCATION: (466)
<223> OTHER INFORMATION: Variable amino acid
<221> NAME/KEY: MOD_RES
<222> LOCATION: (469)..(470)
<223> OTHER INFORMATION: Variable amino acid
<221> NAME/KEY: MOD_RES
<222> LOCATION: (473)..(475)
<223> OTHER INFORMATION: Variable amino acid
<221> NAME/KEY: MOD_RES
```

-continued

```
<222> LOCATION: (478)..(480)
<223> OTHER INFORMATION: Variable amino acid
<221> NAME/KEY: MOD_RES
<222> LOCATION: (482)
<223> OTHER INFORMATION: Variable amino acid
<221> NAME/KEY: MOD_RES
<222> LOCATION: (486)
<223> OTHER INFORMATION: Variable amino acid
<221> NAME/KEY: MOD_RES
<222> LOCATION: (491)..(493)
<223> OTHER INFORMATION: Variable amino acid
<221> NAME/KEY: MOD_RES
<222> LOCATION: (495)
<223> OTHER INFORMATION: Variable amino acid
<221> NAME/KEY: MOD_RES
<222> LOCATION: (498)..(503)
<223> OTHER INFORMATION: Variable amino acid
<221> NAME/KEY: MOD_RES
<222> LOCATION: (505)..(508)
<223> OTHER INFORMATION: Variable amino acid
<221> NAME/KEY: MOD_RES
<222> LOCATION: (510)
<223> OTHER INFORMATION: Variable amino acid

<400> SEQUENCE: 6

Xaa Xaa Xaa Xaa Xaa Xaa Xaa Xaa Xaa Gly Xaa Ser Gly Xaa Thr Ala
 1               5                  10                  15

Xaa Asp Val Xaa Ala Val Ala Arg His Xaa Ala Arg Xaa Xaa Xaa Ser
            20                  25                  30

Xaa Xaa Xaa Xaa Glu Xaa Leu Ala Xaa Xaa Arg Xaa Xaa Xaa Asp Ala
        35                  40                  45

Leu Ala Xaa Xaa Xaa Xaa Pro Val Tyr Gly Xaa Ser Thr Gly Phe Gly
 50                  55                  60

Ala Leu Ala Xaa Arg His Ile Xaa Xaa Glu Xaa Arg Ala Xaa Leu Gln
 65                  70                  75                  80

Arg Xaa Xaa Xaa Arg Ser His Ala Ala Gly Met Gly Xaa Xaa Val Glu
                85                  90                  95

Arg Glu Val Val Arg Ala Leu Met Phe Leu Arg Xaa Lys Thr Xaa Ala
            100                 105                 110

Ser Gly Xaa Thr Gly Val Arg Pro Xaa Val Xaa Xaa Thr Met Xaa Gly
        115                 120                 125

Xaa Leu Asn Ala Gly Ile Thr Pro Val Val Xaa Glu Tyr Gly Ser Leu
130                 135                 140

Gly Cys Ser Gly Asp Leu Ala Pro Leu Ser His Cys Ala Leu Xaa Leu
145                 150                 155                 160

Met Gly Glu Gly Glu Ala Thr Xaa Xaa Xaa Gly Xaa Xaa Arg Pro Xaa
                165                 170                 175

Xaa Glu Leu Xaa Ala Xaa Xaa Gly Xaa Xaa Pro Val Glu Leu Xaa Glu
            180                 185                 190

Lys Glu Gly Leu Ala Leu Xaa Asn Gly Thr Asp Gly Met Leu Gly Xaa
            195                 200                 205

Leu Xaa Met Ala Leu Ala Asp Leu Xaa Xaa Leu Xaa Xaa Xaa Ala Asp
210                 215                 220

Xaa Thr Ala Ala Xaa Ser Xaa Glu Ala Xaa Leu Gly Thr Asp Xaa Val
225                 230                 235                 240

Xaa Xaa Xaa Glu Leu His Xaa Xaa Xaa Arg Pro His Pro Gly Gln Gly
                245                 250                 255

Xaa Ser Ala Xaa Asn Met Xaa Xaa Xaa Leu Ala Xaa Ser Xaa Xaa Xaa
            260                 265                 270

Xaa Xaa His Xaa Xaa Xaa Xaa Xaa Arg Val Gln Asp Ala Tyr Ser Xaa
275                 280                 285
```

```
Arg Cys Xaa Pro Gln Val Xaa Gly Ala Xaa Arg Asp Thr Xaa Xaa His
    290                 295                 300
Ala Xaa Leu Val Ala Xaa Arg Glu Leu Ala Xaa Xaa Xaa Asp Asn Pro
305                 310                 315                 320
Val Val Leu Pro Xaa Gly Xaa Val Xaa Ser Asn Gly Asn Phe His Gly
                325                 330                 335
Ala Pro Val Ala Tyr Val Leu Asp Phe Leu Ala Ile Xaa Xaa Ala Asp
                340                 345                 350
Leu Gly Ser Ile Xaa Glu Arg Arg Thr Asp Arg Xaa Leu Asp Xaa Xaa
            355                 360                 365
Arg Ser Xaa Xaa Leu Pro Xaa Phe Leu Ala Asp Asp Xaa Gly Val Asp
    370                 375                 380
Ser Gly Xaa Met Ile Ala Gln Tyr Thr Gln Ala Xaa Leu Val Xaa Glu
385                 390                 395                 400
Xaa Lys Arg Leu Ala Val Pro Ala Ser Xaa Asp Ser Ile Pro Ser Ser
                405                 410                 415
Ala Met Gln Glu Asp His Val Ser Xaa Gly Trp Xaa Ala Ala Arg Lys
                420                 425                 430
Leu Arg Thr Xaa Val Xaa Asn Leu Xaa Arg Ile Xaa Ala Val Glu Xaa
            435                 440                 445
Xaa Xaa Ala Xaa Arg Ala Xaa Xaa Leu Arg Ala Xaa Xaa Xaa Leu Xaa
    450                 455                 460
Pro Xaa Pro Ala Xaa Xaa Ala Val Xaa Xaa Xaa Leu Arg Xaa Xaa Xaa
465                 470                 475                 480
Ala Xaa Gly Pro Gly Xaa Asp Arg Phe Leu Xaa Xaa Xaa Leu Xaa Ala
                485                 490                 495
Ala Xaa Xaa Xaa Xaa Xaa Gly Xaa Xaa Xaa Xaa Ala Xaa Glu
                500                 505                 510

<210> SEQ ID NO 7
<211> LENGTH: 1542
<212> TYPE: DNA
<213> ORGANISM: Artificial Sequence
<220> FEATURE:
<223> OTHER INFORMATION: Description of Artificial Sequence: Synthetic
      expression vector sequence

<400> SEQUENCE: 7
atggcttccg ctcctcaaat aaacacttggc ctaagtggcg caaccgcaga cgacgttatc      60
gccgttgccc gccacgaagc ccgcatcagc atttctccgc aagtacttga ggaactggct     120
tccgtccgag cacatatcga tgcactagca tccgctgata ccccggttta tggcatttca     180
accggctttg gcgcgttggc aacccgccac atcgcacccg aggatcgcgc caagctgcag     240
cgctccctca tccgttccca cgctgctggc atgggtgaac cggtggagcg cgaagtggtc     300
cgcgcattga tgttcttgcg tgcaaagacc ctggcttccg gccgcacggg cgttcgcccg     360
gttgtccttg agaccatggt cggcatgctc aatgcaggca tcactccggt agtccgcgaa     420
tacggttcac tgggctgctc cggtgacttg gctccgctgt cgcactgcgc attagtgctg     480
atgggcgagg gcgaagccac cgatgcccac ggcgacatcc gcccggtacc ggaactgttc     540
gccgaggccg gattgacccc tgtcgaactg cagaaaagg aaggcctggc tctggtcaac     600
ggcaccgacg gcatgctcgg ccagctgatc atggcattgg cggacctcga tgagctgctg     660
gacatcgccg atgccaccgc cgccatgagc gttgaagccc agctgggcac cgatcaggta     720
ttccgcgcag aactgcacga accactgcgc ccgcacccag gccagggccg cagcgcccag     780
```

```
aacatgttcg ccttcctggc cgactcgcca attgttgcct cgcatcgcga gggagacggc    840
cgagtgcagg atgcctactc gctgcgttgc tcgccgcagg tcaccggcgc cgcccgcgac    900
accattgctc atgcccgcct ggtcgccacc cgcgaactgg ctgcggccat tgacaaccct    960
gtggtgctgc ccagcggcga agtgacttcc aacggcaact tccacggcgc accggtagcc   1020
tacgtgctgg acttccttgc catcgccgtg gccgacctcg gctctatcgc cgagcgccgc   1080
accgaccgca tgctcgaccc agcccgctcc cgcgacctgc cggcattcct ggccgacgat   1140
ccgggtgtgg actcgggcat gatgatcgcc cagtacaccc aggccggctt ggtggcagaa   1200
aacaagcggc tggcagttcc tgccagcgtt gactccatcc catcctcggc catgcaggaa   1260
gaccacgttt ccctgggctg gcatgcggcg cgcaagctgc gcacctcggt agcgaacctc   1320
cgccgcattc tcgcagtgga aatgctgatt gccggccgcg ccctggacct gcgggcccca   1380
ttgaagcctg gtccagcgac cggtgcggtg cttgaagtat tgcgcagcaa ggttgcaggc   1440
cccggccagg accgcttcct ttccgcagaa ctggaagcag cctatgacct gctggccaat   1500
ggctcggtgc ataaggccct cgaagctcac ctgcctgcat aa                       1542
```

<210> SEQ ID NO 8
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Ala Ser Ala Pro Gln Ile Thr Leu Gly Leu Ser Gly Ala Thr Ala
  1               5                  10                  15

Asp Asp Val Ile Ala Val Ala Arg His Glu Ala Arg Ile Ser Ile Ser
                 20                  25                  30

Pro Gln Val Leu Glu Glu Leu Ala Ser Val Arg Ala His Ile Asp Ala
             35                  40                  45

Leu Ala Ser Ala Asp Thr Pro Val Tyr Gly Ile Ser Thr Gly Phe Gly
         50                  55                  60

Ala Leu Ala Thr Arg His Ile Ala Pro Glu Asp Arg Ala Lys Leu Gln
 65                  70                  75                  80

Arg Ser Leu Ile Arg Ser His Ala Ala Gly Met Gly Glu Pro Val Glu
                 85                  90                  95

Arg Glu Val Val Arg Ala Leu Met Phe Leu Arg Ala Lys Thr Leu Ala
            100                 105                 110

Ser Gly Arg Ser Val Arg Pro Val Leu Glu Thr Met Val Gly Met
            115                 120                 125

Leu Asn Ala Gly Ile Thr Pro Val Val Arg Glu Tyr Gly Ser Leu Gly
        130                 135                 140

Cys Ser Gly Asp Leu Ala Pro Leu Ser His Cys Ala Leu Val Leu Met
145                 150                 155                 160

Gly Glu Gly Glu Ala Thr Asp Ala His Gly Asp Ile Arg Pro Val Pro
                165                 170                 175

Glu Leu Phe Ala Glu Ala Gly Leu Thr Pro Val Glu Leu Ala Glu Lys
            180                 185                 190

Glu Gly Leu Ala Leu Val Asn Gly Thr Asp Gly Met Leu Gly Gln Leu
        195                 200                 205

Ile Met Ala Leu Ala Asp Leu Asp Glu Leu Leu Asp Ile Ala Asp Ala
    210                 215                 220
```

```
Thr Ala Ala Met Ser Val Glu Ala Gln Leu Gly Thr Asp Gln Val Phe
225                 230                 235                 240

Arg Ala Glu Leu His Glu Pro Leu Arg Pro His Pro Gly Gln Gly Arg
                245                 250                 255

Ser Ala Gln Asn Met Phe Ala Phe Leu Ala Asp Ser Pro Ile Val Ala
                260                 265                 270

Ser His Arg Glu Gly Asp Gly Arg Val Gln Asp Ala Tyr Ser
                275                 280                 285

<210> SEQ ID NO 9
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Ser Ala Pro Gln Ile Thr Leu Gly Leu Ser Gly Ala Thr Ala
 1               5                  10                  15

Asp Asp Val Ile Ala Val Ala Arg His Glu Ala Arg Ile Ser Ile Ser
                20                  25                  30

Pro Gln Val Leu Glu Glu Leu Ala Ser Val Arg Ala His Ile Asp Ala
            35                  40                  45

Leu Ala Ser Ala Asp Thr Pro Val Tyr Gly Ile Ser Thr Gly Phe Gly
        50                  55                  60

Ala Leu Ala Thr Arg His Ile Ala Pro Glu Asp Arg Ala Lys Leu Gln
65                  70                  75                  80

Arg Ser Leu Ile Arg Ser His Ala Ala Gly Met Gly Glu Pro Val Glu
                85                  90                  95

Arg Glu Val Val Arg Ala Leu Met Phe Leu Arg Ala Lys Thr Leu Ala
                100                 105                 110

Ser Gly Arg Ser Val Arg Pro Val Val Leu Glu Thr Met Val Gly Met
            115                 120                 125

Leu Asn Ala Gly Ile Thr Pro Val Val Arg Glu Tyr Gly Ser Leu Gly
130                 135                 140

Cys Ser Gly Asp Leu Ala Pro Leu Ser His Cys Ala Leu Val Leu Met
145                 150                 155                 160

Gly Glu Gly Glu Ala Thr Asp Ala His Gly Asp Ile Arg Pro Val Pro
                165                 170                 175

Glu Leu Phe Ala Glu Ala Gly Leu Thr Pro Val Glu Leu Ala Glu Lys
            180                 185                 190

Glu Gly Leu Ala Leu Val Asn Gly Thr Asp Gly Met Leu Gly Gln Leu
        195                 200                 205

Ile Met Ala Leu Ala Asp Leu Asp Glu Leu Leu Asp Ile Ala Asp Ala
210                 215                 220

Thr Ala Ala Met Ser Val Glu Ala Gln Leu Gly Thr Asp Gln Val Phe
225                 230                 235                 240

Arg Ala Glu Leu His Glu Pro Leu Arg Pro His Pro Gly Gln Gly Arg
                245                 250                 255

Ser Ala Gln Asn Met Phe Ala Phe Leu Ala Asp Ser Pro Ile Val Ala
                260                 265                 270

Ser His Arg Glu Gly Asp Gly Arg Val Gln Asp Ala Tyr Ser Leu Arg
                275                 280                 285

Cys Ser Pro Gln Val Thr Gly Ala Ala Arg Asp Thr Ile Ala His Ala
```

-continued

```
            290                 295                 300
Arg Leu Val Ala Thr Arg Glu Leu Ala Ala Ile Asp Asn Pro Val
305                 310                 315                 320

Val Leu Pro Ser Gly Glu Val Thr Ser Asn Gly Asn Phe His Gly Ala
                325                 330                 335

Pro Val Ala Tyr Val Leu Asp Phe Leu Ala Ile Ala Val Ala Asp Leu
                340                 345                 350

Gly Ser Ile Ala Glu Arg Arg Thr Asp Arg Met Leu Asp Pro Ala Arg
                355                 360                 365

Ser Arg Asp Leu Pro Ala Phe Leu Ala Asp Pro Gly Val Asp Ser
370                 375                 380

Gly Met Met Ile Ala Gln Tyr Thr Gln Ala Gly Leu Val Ala Glu Asn
385                 390                 395                 400

Lys Arg Leu Ala

<210> SEQ ID NO 10
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Ser Ala Pro Gln Ile Thr Leu Gly Leu Ser Gly Ala Thr Ala
1               5                   10                  15

Asp Asp Val Ile Ala Val Ala Arg His Glu Ala Arg Ile Ser Ile Ser
                20                  25                  30

Pro Gln Val Leu Glu Glu Leu Ala Ser Val Arg Ala His Ile Asp Ala
            35                  40                  45

Leu Ala Ser Ala Asp Thr Pro Val Tyr Gly Ile Ser Thr Gly Phe Gly
        50                  55                  60

Ala Leu Ala Thr Arg His Ile Ala Pro Glu Asp Arg Ala Lys Leu Gln
65                  70                  75                  80

Arg Ser Leu Ile Arg Ser His Ala Ala Gly Met Gly Glu Pro Val Glu
                85                  90                  95

Arg Glu Val Val Arg Ala Leu Met Phe Leu Arg Ala Lys Thr Leu Ala
                100                 105                 110

Ser Gly Arg Ser Val Arg Pro Val Leu Glu Thr Met Val Gly Met
            115                 120                 125

Leu Asn Ala Gly Ile Thr Pro Val Val Arg Glu Tyr Gly Ser Leu Gly
130                 135                 140

Cys Ser Gly Asp Leu Ala Pro Leu Ser His Cys Ala Leu Val Leu Met
145                 150                 155                 160

Gly Glu Gly Glu Ala Thr Asp Ala His Gly Asp Ile Arg Pro Val Pro
                165                 170                 175

Glu Leu Phe Ala Glu Ala Gly Leu Thr Pro Val Glu Leu Ala Glu Lys
                180                 185                 190

Glu Gly Leu Ala Leu Val Asn Gly Thr Asp Gly Met Leu Gly Gln Leu
            195                 200                 205

Ile Met Ala Leu Ala Asp Leu Asp Glu Leu Leu Asp Ile Ala Asp Ala
        210                 215                 220

Thr Ala Ala Met Ser Val Glu Ala Gln Leu Gly Thr Asp Gln Val Phe
225                 230                 235                 240

Arg Ala Glu Leu His Glu Pro Leu Arg Pro His Pro Gly Gln Gly Arg
```

245                 250                 255
Ser Ala Gln Asn Met Phe Ala Phe Leu Ala Asp Ser Pro Ile Val Ala
                260                 265                 270

Ser His Arg Glu Gly Asp Gly Arg Val Gln Asp Ala Tyr Ser Leu Arg
            275                 280                 285

Cys Ser Pro Gln Val Thr Gly Ala Ala Arg Asp Thr Ile Ala His Ala
        290                 295                 300

Arg Leu Val Ala Thr Arg Glu Leu Ala Ala Ile Asp Asn Pro Val
305                 310                 315                 320

Val Leu Pro Ser Gly Glu Val Thr Ser Asn Gly Asn Phe His Gly Ala
                325                 330                 335

Pro Val Ala Tyr Val Leu Asp Phe Leu Ala Ile Ala Val Ala Asp Leu
            340                 345                 350

Gly Ser Ile Ala Glu Arg Arg Thr Asp Arg Met Leu Asp Pro Ala Arg
        355                 360                 365

Ser Arg Asp Leu Pro Ala Phe Leu Ala Asp Asp Pro Gly Val Asp Ser
    370                 375                 380

Gly Met Met Ile Ala Gln Tyr Thr Gln Ala Gly Leu Val Ala Glu Asn
385                 390                 395                 400

Lys Arg Leu Ala Val Pro Ala Val Asp Ser Ile Pro Ser Ser Ala Met
                405                 410                 415

Gln Glu Asp His Val Ser Leu Gly Trp His Ala Ala Arg Lys Leu Pro
            420                 425                 430

Thr Ser Val Ala Asn Leu Arg Arg Ile Leu Ala Val Glu Met Leu Ile
        435                 440                 445

Ala Gly Arg Ala Leu Asp Leu Arg Ala Pro Leu Lys Pro Gly Pro Ala
    450                 455                 460

Thr Gly Ala Val Leu Glu Val Leu Arg Ser Lys Val Ala Gly Pro Gly
465                 470                 475                 480

Gln Asp Arg Phe Leu Ser Ala Glu Leu Glu Ala Ala Tyr Asp Leu Leu
                485                 490                 495

Ala Asn Gly Ser Val His Lys Ala Leu Glu Ala His Leu Pro Glu
            500                 505                 510

<210> SEQ ID NO 11
<211> LENGTH: 511
<212> TYPE: PRT
<213> ORGANISM: Artificial Sequence
<220> FEATURE:
<223> OTHER INFORMATION: Description of Artificial Sequence: Formula
      polypeptide
<221> NAME/KEY: MOD_RES
<222> LOCATION: (1)..(9)
<223> OTHER INFORMATION: Variable amino acid
<221> NAME/KEY: MOD_RES
<222> LOCATION: (11)
<223> OTHER INFORMATION: Variable amino acid
<221> NAME/KEY: MOD_RES
<222> LOCATION: (14)
<223> OTHER INFORMATION: Variable amino acid
<221> NAME/KEY: MOD_RES
<222> LOCATION: (17)
<223> OTHER INFORMATION: Variable amino acid
<221> NAME/KEY: MOD_RES
<222> LOCATION: (20)
<223> OTHER INFORMATION: Variable amino acid
<221> NAME/KEY: MOD_RES
<222> LOCATION: (26)
<223> OTHER INFORMATION: Variable amino acid
<221> NAME/KEY: MOD_RES
<222> LOCATION: (29)..(31)
<223> OTHER INFORMATION: Variable amino acid

```
<221> NAME/KEY: MOD_RES
<222> LOCATION: (33)..(36)
<223> OTHER INFORMATION: Variable amino acid
<221> NAME/KEY: MOD_RES
<222> LOCATION: (38)
<223> OTHER INFORMATION: Variable amino acid
<221> NAME/KEY: MOD_RES
<222> LOCATION: (41)..(42)
<223> OTHER INFORMATION: Variable amino acid
<221> NAME/KEY: MOD_RES
<222> LOCATION: (44)..(46)
<223> OTHER INFORMATION: Variable amino acid
<221> NAME/KEY: MOD_RES
<222> LOCATION: (51)..(54)
<223> OTHER INFORMATION: Variable amino acid
<221> NAME/KEY: MOD_RES
<222> LOCATION: (59)
<223> OTHER INFORMATION: Variable amino acid
<221> NAME/KEY: MOD_RES
<222> LOCATION: (68)
<223> OTHER INFORMATION: Variable amino acid
<221> NAME/KEY: MOD_RES
<222> LOCATION: (72)..(73)
<223> OTHER INFORMATION: Variable amino acid
<221> NAME/KEY: MOD_RES
<222> LOCATION: (75)
<223> OTHER INFORMATION: Variable amino acid
<221> NAME/KEY: MOD_RES
<222> LOCATION: (78)
<223> OTHER INFORMATION: Variable amino acid
<221> NAME/KEY: MOD_RES
<222> LOCATION: (82)..(84)
<223> OTHER INFORMATION: Variable amino acid
<221> NAME/KEY: MOD_RES
<222> LOCATION: (93)..(94)
<223> OTHER INFORMATION: Variable amino acid
<221> NAME/KEY: MOD_RES
<222> LOCATION: (108)
<223> OTHER INFORMATION: Variable amino acid
<221> NAME/KEY: MOD_RES
<222> LOCATION: (111)
<223> OTHER INFORMATION: Variable amino acid
<221> NAME/KEY: MOD_RES
<222> LOCATION: (115)..(116)
<223> OTHER INFORMATION: Variable amino acid
<221> NAME/KEY: MOD_RES
<222> LOCATION: (120)
<223> OTHER INFORMATION: Variable amino acid
<221> NAME/KEY: MOD_RES
<222> LOCATION: (122)..(123)
<223> OTHER INFORMATION: Variable amino acid
<221> NAME/KEY: MOD_RES
<222> LOCATION: (126)
<223> OTHER INFORMATION: Variable amino acid
<221> NAME/KEY: MOD_RES
<222> LOCATION: (128)
<223> OTHER INFORMATION: Variable amino acid
<221> NAME/KEY: MOD_RES
<222> LOCATION: (138)
<223> OTHER INFORMATION: Variable amino acid
<221> NAME/KEY: MOD_RES
<222> LOCATION: (167)..(169)
<223> OTHER INFORMATION: Variable amino acid
<221> NAME/KEY: MOD_RES
<222> LOCATION: (171)..(172)
<223> OTHER INFORMATION: Variable amino acid
<221> NAME/KEY: MOD_RES
<222> LOCATION: (175)..(176)
<223> OTHER INFORMATION: Variable amino acid
<221> NAME/KEY: MOD_RES
<222> LOCATION: (179)
<223> OTHER INFORMATION: Variable amino acid
<221> NAME/KEY: MOD_RES
<222> LOCATION: (181)..(182)
<223> OTHER INFORMATION: Variable amino acid
<221> NAME/KEY: MOD_RES
<222> LOCATION: (184)..(185)
<223> OTHER INFORMATION: Variable amino acid
<221> NAME/KEY: MOD_RES
```

```
<222> LOCATION: (190)
<223> OTHER INFORMATION: Variable amino acid
<221> NAME/KEY: MOD_RES
<222> LOCATION: (198)
<223> OTHER INFORMATION: Variable amino acid
<221> NAME/KEY: MOD_RES
<222> LOCATION: (207)
<223> OTHER INFORMATION: Variable amino acid
<221> NAME/KEY: MOD_RES
<222> LOCATION: (209)
<223> OTHER INFORMATION: Variable amino acid
<221> NAME/KEY: MOD_RES
<222> LOCATION: (216)..(217)
<223> OTHER INFORMATION: Variable amino acid
<221> NAME/KEY: MOD_RES
<222> LOCATION: (219)..(221)
<223> OTHER INFORMATION: Variable amino acid
<221> NAME/KEY: MOD_RES
<222> LOCATION: (224)
<223> OTHER INFORMATION: Variable amino acid
<221> NAME/KEY: MOD_RES
<222> LOCATION: (228)
<223> OTHER INFORMATION: Variable amino acid
<221> NAME/KEY: MOD_RES
<222> LOCATION: (230)
<223> OTHER INFORMATION: Variable amino acid
<221> NAME/KEY: MOD_RES
<222> LOCATION: (233)
<223> OTHER INFORMATION: Variable amino acid
<221> NAME/KEY: MOD_RES
<222> LOCATION: (238)
<223> OTHER INFORMATION: Variable amino acid
<221> NAME/KEY: MOD_RES
<222> LOCATION: (240)..(242)
<223> OTHER INFORMATION: Variable amino acid
<221> NAME/KEY: MOD_RES
<222> LOCATION: (246)..(248)
<223> OTHER INFORMATION: Variable amino acid
<221> NAME/KEY: MOD_RES
<222> LOCATION: (256)
<223> OTHER INFORMATION: Variable amino acid
<221> NAME/KEY: MOD_RES
<222> LOCATION: (259)
<223> OTHER INFORMATION: Variable amino acid
<221> NAME/KEY: MOD_RES
<222> LOCATION: (262)..(264)
<223> OTHER INFORMATION: Variable amino acid
<221> NAME/KEY: MOD_RES
<222> LOCATION: (267)
<223> OTHER INFORMATION: Variable amino acid
<221> NAME/KEY: MOD_RES
<222> LOCATION: (269)..(273)
<223> OTHER INFORMATION: Variable amino acid
<221> NAME/KEY: MOD_RES
<222> LOCATION: (275)..(279)
<223> OTHER INFORMATION: Variable amino acid
<221> NAME/KEY: MOD_RES
<222> LOCATION: (287)
<223> OTHER INFORMATION: Variable amino acid
<221> NAME/KEY: MOD_RES
<222> LOCATION: (290)
<223> OTHER INFORMATION: Variable amino acid
<221> NAME/KEY: MOD_RES
<222> LOCATION: (294)
<223> OTHER INFORMATION: Variable amino acid
<221> NAME/KEY: MOD_RES
<222> LOCATION: (297)
<223> OTHER INFORMATION: Variable amino acid
<221> NAME/KEY: MOD_RES
<222> LOCATION: (301)..(302)
<223> OTHER INFORMATION: Variable amino acid
<221> NAME/KEY: MOD_RES
<222> LOCATION: (305)
<223> OTHER INFORMATION: Variable amino acid
<221> NAME/KEY: MOD_RES
<222> LOCATION: (309)
<223> OTHER INFORMATION: Variable amino acid
<221> NAME/KEY: MOD_RES
<222> LOCATION: (314)..(316)
```

```
<223> OTHER INFORMATION: Variable amino acid
<221> NAME/KEY: MOD_RES
<222> LOCATION: (324)
<223> OTHER INFORMATION: Variable amino acid
<221> NAME/KEY: MOD_RES
<222> LOCATION: (326)
<223> OTHER INFORMATION: Variable amino acid
<221> NAME/KEY: MOD_RES
<222> LOCATION: (328)
<223> OTHER INFORMATION: Variable amino acid
<221> NAME/KEY: MOD_RES
<222> LOCATION: (348)..(349)
<223> OTHER INFORMATION: Variable amino acid
<221> NAME/KEY: MOD_RES
<222> LOCATION: (356)
<223> OTHER INFORMATION: Variable amino acid
<221> NAME/KEY: MOD_RES
<222> LOCATION: (363)
<223> OTHER INFORMATION: Variable amino acid
<221> NAME/KEY: MOD_RES
<222> LOCATION: (366)..(367)
<223> OTHER INFORMATION: Variable amino acid
<221> NAME/KEY: MOD_RES
<222> LOCATION: (370)..(371)
<223> OTHER INFORMATION: Variable amino acid
<221> NAME/KEY: MOD_RES
<222> LOCATION: (374)
<223> OTHER INFORMATION: Variable amino acid
<221> NAME/KEY: MOD_RES
<222> LOCATION: (380)
<223> OTHER INFORMATION: Variable amino acid
<221> NAME/KEY: MOD_RES
<222> LOCATION: (386)
<223> OTHER INFORMATION: Variable amino acid
<221> NAME/KEY: MOD_RES
<222> LOCATION: (395)
<223> OTHER INFORMATION: Variable amino acid
<221> NAME/KEY: MOD_RES
<222> LOCATION: (398)
<223> OTHER INFORMATION: Variable amino acid
<221> NAME/KEY: MOD_RES
<222> LOCATION: (400)
<223> OTHER INFORMATION: Variable amino acid
<221> NAME/KEY: MOD_RES
<222> LOCATION: (408)
<223> OTHER INFORMATION: Variable amino acid
<221> NAME/KEY: MOD_RES
<222> LOCATION: (423)
<223> OTHER INFORMATION: Variable amino acid
<221> NAME/KEY: MOD_RES
<222> LOCATION: (426)
<223> OTHER INFORMATION: Variable amino acid
<221> NAME/KEY: MOD_RES
<222> LOCATION: (432)
<223> OTHER INFORMATION: Variable amino acid
<221> NAME/KEY: MOD_RES
<222> LOCATION: (434)
<223> OTHER INFORMATION: Variable amino acid
<221> NAME/KEY: MOD_RES
<222> LOCATION: (436)
<223> OTHER INFORMATION: Variable amino acid
<221> NAME/KEY: MOD_RES
<222> LOCATION: (439)
<223> OTHER INFORMATION: Variable amino acid
<221> NAME/KEY: MOD_RES
<222> LOCATION: (442)
<223> OTHER INFORMATION: Variable amino acid
<221> NAME/KEY: MOD_RES
<222> LOCATION: (446)..(448)
<223> OTHER INFORMATION: Variable amino acid
<221> NAME/KEY: MOD_RES
<222> LOCATION: (450)
<223> OTHER INFORMATION: Variable amino acid
<221> NAME/KEY: MOD_RES
<222> LOCATION: (453)..(454)
<223> OTHER INFORMATION: Variable amino acid
<221> NAME/KEY: MOD_RES
<222> LOCATION: (458)..(462)
<223> OTHER INFORMATION: Variable amino acid
```

```
<221> NAME/KEY: MOD_RES
<222> LOCATION: (465)..(466)
<223> OTHER INFORMATION: Variable amino acid
<221> NAME/KEY: MOD_RES
<222> LOCATION: (469)..(471)
<223> OTHER INFORMATION: Variable amino acid
<221> NAME/KEY: MOD_RES
<222> LOCATION: (474)..(476)
<223> OTHER INFORMATION: Variable amino acid
<221> NAME/KEY: MOD_RES
<222> LOCATION: (486)..(488)
<223> OTHER INFORMATION: Variable amino acid
<221> NAME/KEY: MOD_RES
<222> LOCATION: (490)
<223> OTHER INFORMATION: Variable amino acid
<221> NAME/KEY: MOD_RES
<222> LOCATION: (493)..(505)
<223> OTHER INFORMATION: Variable amino acid
<221> NAME/KEY: MOD_RES
<222> LOCATION: (507)..(511)
<223> OTHER INFORMATION: Variable amino acid

<400> SEQUENCE: 11

Xaa Xaa Xaa Xaa Xaa Xaa Xaa Xaa Gly Xaa Ser Gly Xaa Thr Ala
 1               5                  10                  15

Xaa Asp Val Xaa Ala Val Ala Arg His Xaa Ala Arg Xaa Xaa Xaa Ser
            20                  25                  30

Xaa Xaa Xaa Xaa Glu Xaa Leu Ala Xaa Xaa Arg Xaa Xaa Xaa Asp Ala
        35                  40                  45

Leu Ala Xaa Xaa Xaa Xaa Pro Val Tyr Gly Xaa Ser Thr Gly Phe Gly
    50                  55                  60

Ala Leu Ala Xaa Arg His Ile Xaa Xaa Glu Xaa Arg Ala Xaa Leu Gln
65                  70                  75                  80

Arg Xaa Xaa Xaa Arg Ser His Ala Ala Gly Met Gly Xaa Xaa Val Glu
                85                  90                  95

Arg Glu Val Val Arg Ala Leu Met Phe Leu Arg Xaa Lys Thr Xaa Ala
                100                 105                 110

Ser Gly Xaa Xaa Val Arg Pro Xaa Val Xaa Xaa Thr Met Xaa Gly Xaa
            115                 120                 125

Leu Asn Ala Gly Ile Thr Pro Val Val Xaa Glu Tyr Gly Ser Leu Gly
130                 135                 140

Cys Ser Gly Asp Leu Ala Pro Leu Ser His Cys Ala Leu Val Leu Met
145                 150                 155                 160

Gly Glu Gly Glu Ala Thr Xaa Xaa Xaa Gly Xaa Xaa Arg Pro Xaa Xaa
                165                 170                 175

Glu Leu Xaa Ala Xaa Xaa Gly Xaa Xaa Pro Val Glu Leu Xaa Glu Lys
            180                 185                 190

Glu Gly Leu Ala Leu Xaa Asn Gly Thr Asp Gly Met Leu Gly Xaa Leu
            195                 200                 205

Xaa Met Ala Leu Ala Asp Leu Xaa Xaa Leu Xaa Xaa Xaa Ala Asp Xaa
210                 215                 220

Thr Ala Ala Xaa Ser Xaa Glu Ala Xaa Leu Gly Thr Asp Xaa Val Xaa
225                 230                 235                 240

Xaa Xaa Glu Leu His Xaa Xaa Xaa Arg Pro His Pro Gly Gln Gly Xaa
                245                 250                 255

Ser Ala Xaa Asn Met Xaa Xaa Xaa Leu Ala Xaa Ser Xaa Xaa Xaa Xaa
            260                 265                 270

Xaa His Xaa Xaa Xaa Xaa Xaa Arg Val Gln Asp Ala Tyr Ser Xaa Arg
            275                 280                 285

Cys Xaa Pro Gln Val Xaa Gly Ala Xaa Arg Asp Thr Xaa Xaa His Ala
```

```
                  290                 295                 300
Xaa Leu Val Ala Xaa Arg Glu Leu Ala Xaa Xaa Xaa Asp Asn Pro Val
305                 310                 315                 320

Val Leu Pro Xaa Gly Xaa Val Xaa Ser Asn Gly Asn Phe His Gly Ala
                325                 330                 335

Pro Val Ala Tyr Val Leu Asp Phe Leu Ala Ile Xaa Xaa Ala Asp Leu
            340                 345                 350

Gly Ser Ile Xaa Glu Arg Arg Thr Asp Arg Xaa Leu Asp Xaa Xaa Arg
        355                 360                 365

Ser Xaa Xaa Leu Pro Xaa Phe Leu Ala Asp Asp Xaa Gly Val Asp Ser
    370                 375                 380

Gly Xaa Met Ile Ala Gln Tyr Thr Gln Ala Xaa Leu Val Xaa Glu Xaa
385                 390                 395                 400

Lys Arg Leu Ala Val Pro Ala Xaa Asp Ser Ile Pro Ser Ser Ala Met
                405                 410                 415

Gln Glu Asp His Val Ser Xaa Gly Trp Xaa Ala Ala Arg Lys Leu Xaa
                420                 425                 430

Thr Xaa Val Xaa Asn Leu Xaa Arg Ile Xaa Ala Val Glu Xaa Xaa Xaa
            435                 440                 445

Ala Xaa Arg Ala Xaa Xaa Leu Arg Ala Xaa Xaa Xaa Xaa Xaa Pro Ala
    450                 455                 460

Xaa Xaa Ala Val Xaa Xaa Xaa Leu Arg Xaa Xaa Xaa Ala Gly Pro Gly
465                 470                 475                 480

Gln Asp Arg Phe Leu Xaa Xaa Xaa Leu Xaa Ala Ala Xaa Xaa Xaa Xaa
                485                 490                 495

Xaa Xaa Xaa Xaa Xaa Xaa Xaa Xaa Glu Xaa Xaa Xaa Xaa Xaa
            500                 505                 510

<210> SEQ ID NO 12
<211> LENGTH: 1536
<212> TYPE: DNA
<213> ORGANISM: Artificial Sequence
<220> FEATURE:
<223> OTHER INFORMATION: Description of Artificial Sequence: Synthetic
      expression vector sequence

<400> SEQUENCE: 12
atggcttccg ctcctcaaat aacacttggc ctaagtggcg caaccgcaga cgacgttatc      60
gccgttgccc gccacgaagc ccgcatcagc atttctccgc aagtactgga ggaactggct     120
tccgtccgag cacatatcga tgcactagca tccgctgata ccccggttta tggcatttca     180
accggctttg gcgcgttggc aacccgccac atcgcacccg aggatcgcgc caagctgcag     240
cgctccctca tccgttccca cgctgctggc atgggtgaac cggtggagcg cgaagtggtc     300
cgcgcattga tgttcttgcg tgcaaagacc ctggcttccg ccgcagcgt tcgcccggtt     360 gtccttgaga ccatggtcgg catgctcaat gcaggcatca ctccggtagt ccgcgaatac     420
ggttcactgg gctgctccgg tgacttggct ccgctgtcgc actgcgcatt agtgctgatg     480
ggcgagggcg aagccaccga tgcccacggc gacatccgcc cggtaccgga actgttcgcc     540
gaggccggat tgacccctgt cgaactggca gaaaaggaag cctggctct ggtcaacggc     600 accgacggca tgctcggcca gctgatcatg gcattggcgg acctcgatga gctgctggac     660
atcgccgatg ccaccgccgc catgagcgtt gaagcccagc tgggcaccga tcaggtattc     720
cgcgcagaac tgcacgaacc actgcgcccg caccccaggcc agggccgcag cgcccagaac     780
atgttcgcct tcctggccga ctcgccaatt gttgcctcgc atcgcgaggg agacggccga     840
```

```
gtgcaggatg cctactcgct gcgttgctcg ccgcaggtca ccggcgccgc ccgcgacacc      900
attgctcatg cccgcctggt cgccacccgc gaactggctg cggccattga caaccctgtg      960
gtgctgccca gcggcgaagt gacttccaac ggcaacttcc acggcgcacc ggtagcctac     1020
gtgctggact tccttgccat cgccgtggcc gacctcggct ctatcgccga gcgccgcacc     1080
gaccgcatgc tcgacccagc ccgctcccgc gacctgccgg cattcctggc cgacgatccg     1140
ggtgtggact cgggcatgat gatcgcccag tacactcagg ccggcttggt ggcagaaaac     1200
aagcggctgg cagttcctgc agttgactcc atcccatcct cggccatgca ggaagaccac     1260
gtttccctgg gctggcatgc ggcgcgcaag ctgccgacct cggtagcgaa cctccgccgc     1320
attctcgcag tggaaatgct gattgccggc cgcgccctgg acctgcgggc cccattgaag     1380
cctggtccag cgaccggtgc ggtgcttgaa gtattgcgca gcaaggttgc aggccccggc     1440
caggaccgct tcctttccgc agaactggaa gcagcctatg acctgctggc caatggctcg     1500
gtgcataagg ccctcgaagc tcacctgcct gaataa                               1536
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgcgttcagg acgcatactc cgttcgctgc                                        30

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcccatggaa acgtggtctt cctg                                              24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atcatcatgc ccgagtccac a                                                 21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gccatcagga agaccacgtt t                                                 21

<210> SEQ ID NO 17

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atgcaggaag accacgtttc                                              20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atcgaggtcc gccaatgcca t                                            21

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
accggagcag cccagtga                                                18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcttgaagt attgcgccag                                              20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatcctcggg tgcgatgt                                                18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atgctgatcg ggcttcgt                                                18

<210> SEQ ID NO 23
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atttgattca tatggcttcc gctcctc                                          27

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
atcttggatc cgaacatggt gcgttgca                                         28

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agcaccagat cgatgcac                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tggcatgggt gaaccggt                                                    18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atcagcgttg aagcccag                                                    18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acgtgctgga cttccttg                                                    18

<210> SEQ ID NO 29
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 29
gtgcataagg ccctcgaa                                                       18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gagcttcgag ggccttat                                                       18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgagcaacgc agcgagta                                                       18

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Ala Leu Ala Asp Leu Asp Glu Leu Leu Asp Glu Ala
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Gly Glu Pro Val Glu Arg Glu Val Leu Arg Ala
 1               5                  10

<210> SEQ ID NO 34
<211> LENGTH: 509
<212> TYPE: PRT
<213> ORGANISM: Pseudomonas putida

<400> SEQUENCE: 34

Thr Glu Leu Thr Leu Lys Pro Gly Thr Leu Thr Leu Ala Gln Leu Arg
 1               5                  10                  15

Ala Ile His Ala Ala Pro Val Arg Leu Gln Leu Asp Ala Ser Ala Ala
                20                  25                  30

Pro Ala Ile Asp Ala Ser Val Ala Cys Val Glu Gln Ile Ile Ala Glu
            35                  40                  45
```

```
Asp Arg Thr Ala Tyr Gly Ile Asn Thr Gly Phe Gly Leu Leu Ala Ser
 50                  55                  60

Thr Arg Ile Ala Ser His Asp Leu Glu Asn Leu Gln Arg Ser Leu Val
 65                  70                  75                  80

Leu Ser His Ala Ala Gly Ile Gly Ala Pro Leu Asp Asp Asp Leu Val
                 85                  90                  95

Arg Leu Ile Met Val Leu Lys Ile Asn Ser Leu Ser Arg Gly Phe Ser
            100                 105                 110

Gly Ile Arg Arg Lys Val Ile Asp Ala Leu Ile Ala Leu Val Asn Ala
            115                 120                 125

Glu Val Tyr Pro His Ile Pro Leu Lys Gly Ser Val Gly Ala Ser Gly
            130                 135                 140

Asp Leu Ala Pro Leu Ala Thr Met Ser Leu Val Leu Leu Gly Glu Gly
145                 150                 155                 160

Lys Ala Arg Tyr Lys Gly Gln Trp Leu Ser Ala Thr Glu Ala Leu Ala
                165                 170                 175

Val Ala Gly Leu Glu Pro Leu Thr Leu Ala Ala Lys Glu Gly Leu Ala
            180                 185                 190

Leu Leu Asn Gly Thr Gln Ala Ser Thr Ala Tyr Ala Leu Arg Gly Leu
            195                 200                 205

Phe Tyr Ala Glu Asp Leu Tyr Ala Ala Ala Ile Ala Cys Gly Gly Leu
            210                 215                 220

Ser Val Glu Ala Val Leu Gly Ser Arg Ser Pro Phe Asp Ala Arg Ile
225                 230                 235                 240

His Glu Ala Arg Gly Gln Arg Gly Gln Ile Asp Thr Ala Ala Cys Phe
                245                 250                 255

Arg Asp Leu Leu Gly Asp Ser Ser Glu Val Ser Leu Ser His Lys Asn
            260                 265                 270

Cys Asp Lys Val Gln Asp Pro Tyr Ser Leu Arg Cys Gln Pro Gln Val
            275                 280                 285

Met Gly Ala Cys Leu Thr Gln Leu Arg Gln Ala Ala Glu Val Leu Gly
            290                 295                 300

Ile Glu Ala Asn Ala Val Ser Asp Asn Pro Leu Val Phe Ala Ala Glu
305                 310                 315                 320

Gly Asp Val Ile Ser Gly Gly Asn Phe His Ala Glu Pro Val Ala Met
                325                 330                 335

Ala Ala Asp Asn Leu Ala Leu Ala Ile Ala Glu Ile Gly Ser Leu Ser
            340                 345                 350

Glu Arg Arg Ile Ser Leu Met Met Asp Lys His Met Ser Gln Leu Pro
            355                 360                 365

Pro Phe Leu Val Glu Asn Gly Gly Val Asn Ser Gly Phe Met Ile Ala
            370                 375                 380

Gln Val Thr Ala Ala Leu Ala Ser Glu Asn Lys Ala Leu Ser His
385                 390                 395                 400

Pro His Ser Val Asp Ser Leu Pro Thr Ser Ala Asn Gln Glu Asp His
                405                 410                 415

Val Ser Met Ala Pro Ala Ala Gly Lys Arg Leu Trp Glu Met Ala Glu
            420                 425                 430

Asn Thr Arg Gly Val Pro Ala Ile Glu Trp Leu Gly Ala Cys Gln Gly
            435                 440                 445

Leu Asp Leu Arg Lys Gly Leu Lys Thr Ser Ala Lys Leu Glu Lys Ala
450                 455                 460
```

```
Arg Gln Ala Leu Arg Ser Glu Val Ala His Tyr Asp Arg Asp Arg Phe
465                 470                 475                 480

Phe Ala Pro Asp Ile Glu Lys Ala Val Glu Leu Leu Ala Lys Gly Ser
                485                 490                 495

Leu Thr Gly Leu Leu Pro Ala Gly Val Leu Pro Ser Leu
            500                 505
```

<210> SEQ ID NO 35
<211> LENGTH: 511
<212> TYPE: PRT
<213> ORGANISM: Rhizobium meliloti

<400> SEQUENCE: 35

```
Met Thr Val Ile Leu Arg Pro Gly Ser Val Pro Leu Ser Asp Leu Glu
1               5                   10                  15

Thr Ile Tyr Trp Thr Gly Ala Pro Ala Arg Leu Asp Ala Ala Phe Asp
            20                  25                  30

Ala Gly Ile Ala Lys Ala Ala Arg Ile Ala Glu Ile Val Ala Gly
            35                  40                  45

Asn Ala Pro Val Tyr Gly Ile Asn Thr Gly Phe Gly Lys Leu Ala Ser
    50                  55                  60

Ile Lys Ile Asp Ser Ser Asp Val Ala Thr Leu Gln Arg Asn Leu Ile
65                  70                  75                  80

Leu Ser His Cys Cys Gly Val Gly Gln Pro Leu Thr Glu Asp Ile Val
                85                  90                  95

Arg Leu Ile Met Ala Leu Lys Leu Ile Ser Leu Gly Arg Gly Ala Ser
                100                 105                 110

Gly Val Arg Leu Glu Leu Val Arg Leu Ile Glu Ala Met Leu Asp Lys
            115                 120                 125

Gly Val Ile Pro Leu Ile Pro Glu Lys Gly Ser Val Gly Ala Ser Gly
        130                 135                 140

Asp Leu Ala Pro Leu Ala His Met Ala Ala Val Met Met Gly His Gly
145                 150                 155                 160

Glu Ala Phe Phe Ala Gly Glu Arg Met Lys Gly Asp Ala Ala Leu Lys
                165                 170                 175

Ala Ala Gly Leu Ser Pro Val Thr Leu Ala Ala Lys Glu Gly Leu Ala
            180                 185                 190

Leu Ile Asn Gly Thr Gln Val Ser Thr Ala Leu Ala Leu Ala Gly Leu
        195                 200                 205

Phe Arg Ala His Arg Ala Gly Gln Ala Ala Leu Ile Thr Gly Ala Leu
    210                 215                 220

Ser Thr Asp Ala Ala Met Gly Ser Ser Ala Pro Phe His Pro Asp Ile
225                 230                 235                 240

Gln His Cys Ala Ala Ile Arg Ala Arg Ser Thr Arg Ala Ala Ala Leu
                245                 250                 255

Arg Gln Leu Leu Thr Gly Ser Pro Ile Arg Gln Ser His Ile Glu Gly
            260                 265                 270

Asp Glu Arg Val Gln Asp Pro Tyr Cys Ile Arg Cys Gln Pro Gln Val
        275                 280                 285

Asp Gly Ala Cys Leu Asp Leu Leu Arg Ser Val Ala Ala Thr Leu Thr
    290                 295                 300

Ile Glu Ala Asn Ala Val Thr Asp Asn Pro Leu Val Leu Ser Asp Asn
305                 310                 315                 320

Ser Val Val Ser Gly Gly Asn Phe His Ala Glu Pro Val Ala Phe Ala
                325                 330                 335
```

-continued

```
Ala Asp Gln Ile Ala Leu Ala Val Cys Glu Ile Gly Ala Ile Ser Gln
            340                 345                 350

Arg Arg Ile Ala Leu Leu Val Asp Pro Ala Leu Ser Leu Arg Leu Pro
        355                 360                 365

Ala Phe Leu Ala Lys Lys Pro Gly Leu Asn Ser Gly Leu Met Ile Ala
    370                 375                 380

Glu Val Thr Ser Ala Ala Leu Met Ser Glu Asn Lys Gln Leu Ser His
385                 390                 395                 400

Pro Ala Ser Val Asp Ser Thr Pro Thr Ser Ala Asn Gln Glu Asp His
                405                 410                 415

Val Ser Met Ala Cys His Gly Ala Arg Arg Leu Leu Gln Met Thr Glu
            420                 425                 430

Asn Leu Phe Ser Ile Ile Gly Ile Glu Ala Leu Ala Ala Val Gln Gly
        435                 440                 445

Ile Glu Phe Arg Ala Pro Leu Thr Thr Ser Pro Glu Leu Gln Lys Ala
    450                 455                 460

Ala Ala Ala Val Arg Gly Val Ser Ser Ile Glu Glu Asp Arg Tyr
465                 470                 475                 480

Met Ala Asp Asp Leu Lys Ala Ala Gly Asp Leu Val Ala Ser Gly Arg
                485                 490                 495

Leu Ala Ala Ala Val Ser Ala Gly Ile Leu Pro Lys Leu Glu Asn
            500                 505                 510

<210> SEQ ID NO 36
<211> LENGTH: 657
<212> TYPE: PRT
<213> ORGANISM: Mus sp.

<400> SEQUENCE: 36

Met Pro Arg Tyr Thr Val His Val Arg Gly Glu Trp Leu Ala Val Pro
1               5                   10                  15

Cys Gln Asp Gly Lys Leu Thr Val Gly Trp Leu Gly Arg Glu Ala Val
            20                  25                  30

Arg Arg Tyr Met Lys Asn Lys Pro Asp Asn Gly Phe Thr Ser Val
        35                  40                  45

Asp Glu Val Gln Phe Leu Val His Arg Cys Lys Gly Leu Gly Leu Leu
    50                  55                  60

Asp Asn Glu Asp Glu Leu Glu Val Ala Leu Glu Asp Asn Glu Phe Val
65                  70                  75                  80

Glu Val Val Ile Glu Gly Asp Val Met Ser Pro Asp Phe Ile Pro Ser
                85                  90                  95

Gln Pro Glu Gly Val Phe Leu Tyr Ser Lys Tyr Arg Glu Pro Glu Lys
            100                 105                 110

Tyr Ile Ala Leu Asp Gly Asp Ser Leu Ser Thr Glu Asp Leu Val Asn
        115                 120                 125

Leu Gly Lys Gly Arg Tyr Lys Ile Lys Leu Thr Ser Ile Ala Glu Lys
    130                 135                 140

Lys Val Gln Gln Ser Arg Glu Val Ile Asp Ser Ile Ile Lys Glu Arg
145                 150                 155                 160

Thr Val Val Tyr Gly Ile Thr Thr Gly Phe Gly Lys Phe Ala Arg Thr
                165                 170                 175

Val Ile Pro Ala Asn Lys Leu Gln Glu Leu Gln Val Asn Leu Val Arg
            180                 185                 190

Ser His Ser Ser Gly Val Gly Lys Pro Leu Ser Pro Glu Arg Cys Arg
```

-continued

```
                195                 200                 205
Met Leu Leu Ala Leu Arg Ile Asn Val Leu Ala Lys Gly Tyr Ser Gly
    210                 215                 220

Ile Ser Leu Glu Thr Leu Lys Gln Val Ile Glu Ala Phe Asn Ala Ser
225                 230                 235                 240

Cys Leu Ser Tyr Val Pro Glu Lys Gly Thr Val Gly Ala Ser Gly Asp
                245                 250                 255

Leu Ala Pro Leu Ser His Leu Ala Leu Gly Leu Ile Gly Glu Gly Lys
                260                 265                 270

Met Trp Ser Pro Lys Ser Gly Trp Ala Asp Ala Lys Tyr Val Leu Glu
        275                 280                 285

Ala His Gly Leu Lys Pro Ile Val Leu Lys Pro Lys Glu Gly Leu Ala
        290                 295                 300

Leu Ile Asn Gly Thr Gln Met Ile Thr Ser Leu Gly Cys Glu Ala Leu
305                 310                 315                 320

Glu Arg Ala Ser Ala Ile Ala Arg Gln Ala Asp Ile Val Ala Ala Leu
                325                 330                 335

Thr Leu Glu Val Leu Lys Gly Thr Thr Lys Ala Phe Asp Thr Asp Ile
                340                 345                 350

His Ala Val Arg Pro His Arg Gly Gln Ile Glu Val Ala Phe Arg Phe
                355                 360                 365

Arg Ser Leu Leu Asp Ser Asp His His Pro Ser Glu Ile Ala Glu Ser
        370                 375                 380

His Arg Phe Cys Asp Arg Val Gln Asp Ala Tyr Thr Leu Arg Cys Cys
385                 390                 395                 400

Pro Gln Val His Gly Val Val Asn Asp Thr Ile Ala Phe Val Lys Asp
                405                 410                 415

Ile Ile Thr Thr Glu Leu Asn Ser Ala Thr Asp Asn Pro Met Val Phe
                420                 425                 430

Ala Ser Arg Gly Glu Thr Ile Ser Gly Gly Asn Phe His Gly Glu Tyr
        435                 440                 445

Pro Ala Lys Ala Leu Asp Tyr Leu Ala Ile Gly Val His Glu Leu Ala
        450                 455                 460

Ala Ile Ser Glu Arg Arg Ile Glu Arg Leu Cys Asn Pro Ser Leu Ser
465                 470                 475                 480

Glu Leu Pro Ala Phe Leu Val Ala Glu Gly Gly Leu Asn Ser Gly Phe
                485                 490                 495

Met Ile Ala His Cys Thr Ala Ala Leu Val Ser Glu Ser Lys Ala
                500                 505                 510

Leu Cys His Pro Ser Ser Val Asp Ser Leu Ser Thr Ser Ala Ala Thr
        515                 520                 525

Glu Asp His Val Ser Met Gly Gly Trp Ala Ala Arg Lys Ala Leu Arg
        530                 535                 540

Val Val Glu His Val Glu Gln Val Leu Ala Ile Glu Leu Leu Ala Ala
545                 550                 555                 560

Cys Gln Gly Ile Glu Phe Leu Arg Pro Leu Lys Thr Thr Pro Leu
                565                 570                 575

Glu Lys Val Tyr Asp Leu Val Arg Ser Val Val Arg Pro Trp Ile Lys
                580                 585                 590

Asp Arg Phe Met Ala Pro Asp Ile Glu Ala Ala His Arg Leu Leu Leu
        595                 600                 605

Asp Gln Lys Val Trp Glu Val Ala Ala Pro Tyr Ile Glu Lys Tyr Arg
        610                 615                 620
```

Met Glu His Ile Pro Glu Ser Arg Pro Leu Ser Pro Thr Ala Phe Ser
625                 630                 635                 640

Leu Glu Ser Leu Arg Lys Asn Ser Ala Thr Ile Pro Glu Ser Asp Asp
                645                 650                 655

Leu

<210> SEQ ID NO 37
<211> LENGTH: 657
<212> TYPE: PRT
<213> ORGANISM: Rattus sp.

<400> SEQUENCE: 37

Met Pro Arg Tyr Thr Val His Val Arg Gly Glu Trp Leu Ala Val Pro
1               5                   10                  15

Cys Gln Asp Gly Lys Leu Ser Val Gly Trp Leu Gly Arg Glu Ala Val
            20                  25                  30

Arg Arg Tyr Met Lys Asn Lys Pro Asp Asn Gly Phe Thr Ser Val
        35                  40                  45

Asp Glu Val Arg Phe Leu Val Arg Arg Cys Lys Gly Leu Gly Leu Leu
    50                  55                  60

Asp Asn Glu Asp Leu Leu Glu Val Ala Leu Glu Asp Asn Glu Phe Val
65                  70                  75                  80

Glu Val Val Ile Glu Gly Asp Val Met Ser Pro Asp Phe Ile Pro Ser
                85                  90                  95

Gln Pro Glu Gly Val Phe Leu Tyr Ser Lys Tyr Arg Glu Pro Glu Lys
            100                 105                 110

Tyr Ile Ala Leu Asp Gly Asp Ser Leu Ser Thr Glu Asp Leu Val Asn
        115                 120                 125

Leu Gly Lys Gly His Tyr Lys Ile Lys Leu Thr Ser Ile Ala Glu Lys
    130                 135                 140

Lys Val Gln Gln Ser Arg Glu Val Ile Asp Ser Ile Ile Lys Glu Arg
145                 150                 155                 160

Thr Val Val Tyr Gly Ile Thr Thr Gly Phe Gly Lys Phe Ala Arg Thr
                165                 170                 175

Val Ile Pro Ala Asn Lys Leu Gln Glu Leu Gln Val Asn Leu Val Arg
            180                 185                 190

Ser His Ser Ser Gly Val Gly Lys Pro Leu Ser Pro Glu Arg Cys Arg
        195                 200                 205

Met Leu Leu Ala Leu Arg Ile Asn Val Leu Ala Lys Gly Tyr Ser Gly
    210                 215                 220

Ile Ser Leu Glu Thr Leu Lys Gln Val Ile Glu Val Phe Asn Ala Ser
225                 230                 235                 240

Cys Leu Ser Tyr Val Pro Glu Lys Gly Thr Val Gly Ala Ser Gly Asp
                245                 250                 255

Leu Ala Pro Leu Ser His Leu Ala Leu Gly Leu Ile Gly Glu Gly Lys
            260                 265                 270

Met Trp Ser Pro Lys Ser Gly Trp Ala Asp Ala Lys Tyr Val Leu Glu
        275                 280                 285

Ala His Gly Leu Lys Pro Ile Val Leu Lys Pro Lys Glu Gly Leu Ala
    290                 295                 300

Leu Ile Asn Gly Thr Gln Met Ile Thr Ser Leu Gly Cys Glu Ala Val
305                 310                 315                 320

Glu Arg Ala Ser Ala Ile Ala Arg Gln Ala Asp Ile Val Ala Ala Leu
                325                 330                 335

-continued

```
Thr Leu Glu Val Leu Lys Gly Thr Thr Lys Ala Phe Asp Thr Asp Ile
            340                 345                 350

His Ala Val Arg Pro His Arg Gly Gln Ile Glu Val Ala Phe Arg Phe
            355                 360                 365

Arg Ser Leu Leu Asp Ser Asp His His Pro Ser Glu Ile Ala Glu Ser
            370                 375                 380

His Arg Phe Cys Asp Arg Val Gln Asp Ala Tyr Thr Leu Arg Cys Cys
385                 390                 395                 400

Pro Gln Val His Gly Val Val Asn Asp Thr Ile Ala Phe Val Lys Asp
                405                 410                 415

Ile Ile Thr Thr Glu Leu Asn Ser Ala Thr Asp Asn Pro Met Val Phe
            420                 425                 430

Ala Ser Arg Gly Glu Thr Ile Ser Gly Gly Asn Phe His Gly Glu Tyr
            435                 440                 445

Pro Ala Lys Ala Leu Asp Tyr Leu Ala Ile Gly Val His Glu Leu Ala
            450                 455                 460

Ala Ile Ser Glu Arg Arg Ile Glu Arg Leu Cys Asn Pro Ser Leu Ser
465                 470                 475                 480

Glu Leu Pro Ala Phe Leu Val Ala Glu Gly Gly Leu Asn Ser Gly Phe
                485                 490                 495

Met Ile Ala His Cys Thr Ala Ala Leu Val Ser Glu Ser Lys Ala
            500                 505                 510

Leu Cys His Pro Ser Ser Val Asp Ser Leu Ser Thr Ser Ala Ala Thr
            515                 520                 525

Glu Asp His Val Ser Met Gly Gly Trp Ala Ala Arg Lys Ala Leu Arg
530                 535                 540

Val Ile Glu His Val Glu Gln Val Leu Ala Ile Glu Leu Leu Ala Ala
545                 550                 555                 560

Cys Gln Gly Ile Glu Phe Leu Arg Pro Leu Lys Thr Thr Pro Leu
                565                 570                 575

Glu Lys Val Tyr Asp Leu Val Arg Ser Val Val Arg Pro Trp Ile Lys
            580                 585                 590

Asp Arg Phe Met Ala Pro Asp Ile Glu Ala Ala His Arg Leu Leu Leu
            595                 600                 605

Asp Gln Lys Val Trp Glu Val Ala Ala Pro Tyr Ile Glu Lys Tyr Arg
            610                 615                 620

Met Glu His Ile Pro Glu Ser Arg Pro Leu Ser Pro Thr Ala Phe Ser
625                 630                 635                 640

Leu Glu Ser Leu Arg Lys Asn Ser Ala Thr Ile Pro Glu Ser Asp Asp
                645                 650                 655

Leu
```

<210> SEQ ID NO 38
<211> LENGTH: 635
<212> TYPE: PRT
<213> ORGANISM: Homo sapiens

<400> SEQUENCE: 38

```
Met Pro Arg Tyr Thr Val His Val Arg Gly Glu Trp Leu Ala Val Pro
1               5                   10                  15

Cys Gln Asp Ala Gln Leu Thr Val Gly Trp Leu Gly Arg Glu Ala Val
                20                  25                  30

Arg Arg Tyr Ile Lys Asn Lys Pro Asp Asn Gly Gly Phe Thr Ser Val
            35                  40                  45
```

-continued

```
Asp Asp Ala His Phe Leu Val Arg Arg Cys Lys Gly Leu Gly Leu Leu
 50                  55                  60

Asp Asn Glu Asp Arg Leu Glu Val Ala Leu Glu Asn Asn Glu Phe Val
 65                  70                  75                  80

Glu Val Val Ile Glu Gly Asp Ala Met Ser Pro Asp Phe Ile Pro Ser
                 85                  90                  95

Gln Pro Glu Gly Val Tyr Leu Tyr Ser Lys Tyr Arg Glu Pro Glu Lys
                100                 105                 110

Tyr Ile Glu Leu Asp Gly Asp Arg Leu Thr Thr Glu Asp Leu Val Asn
            115                 120                 125

Leu Gly Lys Gly Arg Tyr Lys Ile Lys Leu Thr Pro Thr Ala Glu Lys
130                 135                 140

Arg Val Gln Lys Ser Arg Glu Val Ile Asp Ser Ile Ile Lys Glu Lys
145                 150                 155                 160

Thr Val Val Tyr Gly Ile Thr Thr Gly Phe Gly Lys Phe Ala Arg Thr
                165                 170                 175

Val Ile Pro Ile Asn Lys Leu Gln Glu Leu Gln Val Asn Leu Val Arg
            180                 185                 190

Ser His Ser Ser Gly Val Gly Lys Pro Leu Ser Pro Glu Arg Cys Arg
        195                 200                 205

Met Leu Leu Ala Leu Arg Ile Asn Val Leu Ala Lys Gly Tyr Ser Gly
210                 215                 220

Ile Ser Leu Glu Thr Leu Lys Gln Val Ile Glu Met Phe Asn Ala Ser
225                 230                 235                 240

Cys Leu Pro Tyr Val Pro Glu Lys Gly Thr Val Gly Ala Ser Gly Asp
                245                 250                 255

Leu Ala Pro Leu Ser His Leu Ala Leu Gly Leu Val Gly Glu Gly Lys
                260                 265                 270

Met Trp Ser Pro Lys Ser Gly Trp Ala Asp Ala Lys Tyr Val Leu Glu
        275                 280                 285

Ala His Gly Leu Lys Pro Val Ile Leu Lys Pro Lys Glu Gly Leu Ala
290                 295                 300

Leu Ile Asn Gly Thr Gln Met Ile Thr Ser Leu Gly Cys Glu Ala Val
305                 310                 315                 320

Glu Arg Ala Ser Ala Ile Ala Arg Gln Ala Asp Ile Val Ala Ala Leu
                325                 330                 335

Thr Leu Glu Val Leu Lys Gly Thr Thr Lys Ala Phe Asp Thr Asp Ile
            340                 345                 350

His Ala Leu Arg Pro His Arg Gly Gln Ile Glu Val Ala Phe Arg Phe
        355                 360                 365

Arg Ser Leu Leu Asp Ser Leu Arg Cys Cys Pro Gln Val His Gly Val
370                 375                 380

Val Asn Asp Thr Ile Ala Phe Val Lys Asn Ile Ile Thr Thr Glu Leu
385                 390                 395                 400

Asn Ser Ala Thr Asp Asn Pro Met Val Phe Ala Asn Arg Gly Glu Thr
                405                 410                 415

Val Ser Gly Gly Asn Phe His Gly Glu Tyr Pro Ala Lys Ala Leu Asp
            420                 425                 430

Tyr Leu Ala Ile Gly Ile His Glu Leu Ala Ala Ile Ser Glu Arg Arg
        435                 440                 445

Ile Glu Arg Leu Cys Asn Pro Ser Leu Ser Glu Leu Pro Ala Phe Leu
450                 455                 460
```

-continued

```
Val Ala Glu Gly Gly Leu Asn Ser Gly Phe Met Ile Ala His Cys Thr
465                 470                 475                 480

Ala Ala Ala Leu Val Ser Glu Asn Lys Ala Leu Cys His Pro Ser Ser
            485                 490                 495

Val Asp Ser Leu Ser Thr Ser Ala Ala Thr Glu Asp His Val Ser Met
        500                 505                 510

Gly Gly Trp Ala Ala Arg Lys Ala Leu Arg Val Ile Glu His Val Glu
    515                 520                 525

Gln Val Leu Ala Ile Glu Leu Ala Ala Cys Gln Gly Ile Glu Phe
530                 535                 540

Leu Arg Pro Leu Lys Thr Thr Pro Leu Glu Lys Val Tyr Asp Leu
545                 550                 555                 560

Val Arg Ser Val Val Arg Pro Trp Ile Lys Asp Arg Phe Met Ala Pro
                565                 570                 575

Asp Ile Glu Ala Ala His Arg Leu Leu Leu Glu Gln Lys Val Trp Glu
            580                 585                 590

Val Ala Ala Pro Tyr Ile Glu Lys Tyr Arg Met Glu His Ile Pro Glu
        595                 600                 605

Ser Arg Pro Leu Ser Pro Thr Ala Phe Ser Leu Gln Phe Leu His Lys
    610                 615                 620

Lys Ser Thr Lys Ile Pro Glu Ser Gly Asp Leu
625                 630                 635

<210> SEQ ID NO 39
<211> LENGTH: 677
<212> TYPE: PRT
<213> ORGANISM: Caenorhabditis elegans

<400> SEQUENCE: 39

Met Arg Leu Gln Val Gln Ile Gly Thr Glu Cys Val Val Pro Cys
1               5                   10                  15

Lys Pro Asp Asp Thr Ile His Ala Val Ala Lys Lys Ser Val Glu Lys
                20                  25                  30

Leu Arg Arg Leu Arg Pro Lys Leu Pro Leu Ala Asp Asp Tyr Phe Glu
            35                  40                  45

Val Arg Arg Thr Val Gly Asn Ser Leu Leu Asp Pro Glu Asp Leu Val
        50                  55                  60

Ser Asp Val Leu Lys Asp Ser Asp Phe Ile Ile Val Ala Ala Ser Val
65                  70                  75                  80

Glu Glu Thr Glu Asp Ala Lys Glu Ala Lys Gln Glu Glu Ile Asp
                85                  90                  95

Asn Ala Arg Ala Glu Ile Glu Lys Ile Asp Asn Arg Arg Lys Val
            100                 105                 110

Ser Phe Ala Asp Ser Leu Ala Pro Met Val Leu Ala Pro Pro Thr Lys
        115                 120                 125

Leu Leu Ile Leu Asp Gly Asn Ser Leu Leu Pro Glu Asp Leu Val Arg
        130                 135                 140

Cys Glu Lys Gly Glu Cys Ala Ile Gln Leu Ser Met Glu Ser Glu Asp
145                 150                 155                 160

Arg Ile Arg Lys Ala Arg Thr Phe Leu Glu Lys Ile Ala Ser Glu His
                165                 170                 175

Arg Ala Val Tyr Gly Val Thr Gly Phe Gly Thr Phe Ser Asn Val
            180                 185                 190

Thr Ile Pro Pro Glu Lys Leu Lys Lys Leu Gln Leu Asn Leu Ile Arg
        195                 200                 205
```

```
Ser His Ala Thr Gly Tyr Gly Glu Pro Leu Ala Pro Asn Arg Ala Arg
    210                 215                 220

Met Leu Leu Ala Leu Arg Ile Asn Ile Leu Ala Lys Gly His Ser Gly
225                 230                 235                 240

Ile Ser Val Glu Asn Ile Lys Lys Met Ile Ala Ala Phe Asn Ala Phe
                245                 250                 255

Cys Val Ser Tyr Val Pro Gln Gln Gly Thr Val Gly Cys Ser Gly Asp
            260                 265                 270

Leu Cys Pro Leu Ala His Leu Ala Leu Gly Leu Gly Glu Gly Lys
        275                 280                 285

Met Trp Ser Pro Thr Thr Gly Trp Gln Pro Ala Asp Val Val Leu Lys
290                 295                 300

Lys Asn Asn Leu Glu Pro Leu Glu Leu Gly Pro Lys Glu Gly Leu Ala
305                 310                 315                 320

Leu Ile Asn Gly Thr Gln Met Val Thr Ala Leu Gly Ala Tyr Thr Leu
                325                 330                 335

Glu Arg Ala His Asn Ile Ala Arg Gln Ala Asp Val Ile Ala Ala Leu
            340                 345                 350

Ser Leu Asp Val Leu Lys Gly Thr Thr Arg Ala Tyr Asp Pro Asp Ile
        355                 360                 365

His Arg Ile Arg Pro His Arg Gly Gln Asn Leu Ser Ala Leu Arg Leu
    370                 375                 380

Arg Ala Leu Leu His Ser Glu Ala Asn Pro Ser Gln Ile Ala Glu Ser
385                 390                 395                 400

His Arg Asn Cys Thr Lys Val Gln Asp Ala Tyr Thr Leu Arg Cys Val
                405                 410                 415

Pro Gln Val His Gly Val Val His Asp Thr Ile Glu Phe Val Arg Glu
            420                 425                 430

Ile Ile Thr Thr Glu Met Asn Ser Ala Thr Asp Asn Pro Leu Val Phe
        435                 440                 445

Ala Asp Arg Glu Glu Ile Ile Ser Gly Gly Asn Phe His Gly Glu Tyr
450                 455                 460

Pro Ala Lys Ala Leu Asp Phe Leu Ala Ile Ala Val Ala Glu Leu Ala
465                 470                 475                 480

Gln Met Ser Glu Arg Arg Leu Glu Arg Leu Val Asn Lys Glu Leu Ser
                485                 490                 495

Gly Leu Pro Thr Glu Leu Thr Pro Asp Gly Gly Leu Asn Ser Gly Phe
            500                 505                 510

Met Thr Val Gln Leu Cys Ala Ala Ser Leu Val Ser Glu Asn Lys Val
        515                 520                 525

Leu Cys His Pro Ser Ser Val Asp Ser Ile Pro Thr Ser Cys Asn Gln
    530                 535                 540

Glu Asp His Val Ser Met Gly Gly Phe Ala Ala Arg Lys Ala Leu Thr
545                 550                 555                 560

Val Val Glu His Val Glu Ala Val Leu Ala Met Glu Leu Leu Ala Ala
                565                 570                 575

Cys Gln Gly Ile Glu Phe Leu Lys Pro Leu Ile Ser Thr Ala Pro Leu
            580                 585                 590

His Lys Ile Tyr Gln Leu Val Arg Ser Val Ala Pro Pro Leu Asn Glu
        595                 600                 605

Asp Arg Tyr Met Lys Pro Glu Ile Asp Ala Val Leu Glu Met Ile Arg
610                 615                 620
```

```
Glu Asn Arg Ile Trp Glu Ala Val Leu Pro His Leu Glu Thr Leu Glu
625                 630                 635                 640

Ala Met Glu Glu Leu Asp Pro Asp Ala Leu Arg Gln Phe Thr Lys Thr
            645                 650                 655

Pro Thr Gly Ile Val Gln Asp Arg Ser Met Ile Pro Ile Ser Asp Asp
            660                 665                 670

Glu Glu Ser Ile Glu
        675

<210> SEQ ID NO 40
<211> LENGTH: 508
<212> TYPE: PRT
<213> ORGANISM: Bacillus subtilis

<400> SEQUENCE: 40

Met Val Thr Leu Asp Gly Ser Ser Leu Thr Thr Ala Asp Val Ala Arg
 1               5                  10                  15

Val Leu Phe Asp Phe Glu Ala Ala Ser Glu Glu Ser Met Glu
            20                  25                  30

Arg Val Lys Lys Ser Arg Ala Ala Val Glu Arg Ile Val Arg Asp Glu
        35                  40                  45

Lys Thr Ile Tyr Gly Ile Asn Thr Gly Phe Gly Lys Phe Ser Asp Val
 50                  55                  60

Leu Ile Gln Lys Glu Asp Ser Ala Ala Leu Gln Leu Asn Leu Ile Leu
 65                  70                  75                  80

Ser His Ala Cys Gly Val Gly Asp Pro Phe Pro Glu Cys Val Ser Arg
            85                  90                  95

Ala Met Leu Leu Leu Arg Ala Asn Ala Leu Leu Lys Gly Phe Ser Gly
            100                 105                 110

Val Arg Ala Glu Leu Ile Glu Gln Leu Leu Ala Phe Leu Asn Lys Arg
        115                 120                 125

Val His Pro Val Ile Pro Gln Gln Gly Ser Leu Gly Ala Ser Gly Asp
130                 135                 140

Leu Ala Pro Leu Ser His Leu Ala Leu Ala Leu Ile Gly Gln Gly Glu
145                 150                 155                 160

Val Phe Phe Glu Gly Glu Arg Met Pro Ala Met Thr Gly Leu Lys Lys
                165                 170                 175

Ala Gly Ile Gln Pro Val Thr Leu Thr Ser Lys Glu Gly Leu Ala Leu
            180                 185                 190

Ile Asn Gly Thr Gln Ala Met Thr Ala Met Gly Val Val Ala Tyr Ile
        195                 200                 205

Glu Ala Glu Lys Leu Ala Tyr Gln Thr Glu Arg Ile Ala Ser Leu Thr
210                 215                 220

Ile Glu Gly Leu Gln Gly Ile Asp Ala Phe Asp Glu Asp Ile His
225                 230                 235                 240

Leu Ala Arg Gly Tyr Gln Glu Gln Ile Asp Val Ala Glu Arg Ile Arg
                245                 250                 255

Phe Tyr Leu Ser Asp Ser Gly Leu Thr Thr Ser Gln Gly Glu Leu Arg
            260                 265                 270

Val Gln Asp Ala Tyr Ser Leu Arg Cys Ile Pro Gln Val His Gly Ala
        275                 280                 285

Thr Trp Gln Thr Leu Gly Tyr Val Lys Glu Lys Leu Glu Ile Glu Met
        290                 295                 300

Asn Ala Ala Thr Asp Asn Pro Leu Ile Phe Asn Asp Gly Asp Lys Val
305                 310                 315                 320
```

```
Ile Ser Gly Gly Asn Phe His Gly Gln Pro Ile Ala Phe Ala Met Asp
            325                 330                 335

Phe Leu Lys Ile Ala Ile Ser Glu Leu Ala Asn Ile Ala Glu Arg Arg
            340                 345                 350

Ile Glu Arg Leu Val Asn Pro Gln Leu Asn Asp Leu Pro Pro Phe Leu
            355                 360                 365

Ser Pro His Pro Gly Leu Gln Ser Gly Ala Met Ile Met Gln Tyr Ala
            370                 375                 380

Ala Ala Ser Leu Val Ser Glu Asn Lys Thr Leu Ala His Pro Ala Ser
385                 390                 395                 400

Val Asp Ser Ile Pro Ser Ser Ala Asn Gln Glu Asp His Val Ser Met
            405                 410                 415

Gly Thr Ile Ala Ala Arg His Ala Tyr Gln Val Ile Ala Asn Thr Arg
            420                 425                 430

Arg Val Ile Ala Ile Glu Ala Ile Cys Ala Leu Gln Ala Val Glu Tyr
            435                 440                 445

Arg Gly Ile Glu His Ala Ala Ser Tyr Thr Lys Gln Leu Phe Gln Glu
            450                 455                 460

Met Arg Lys Val Val Pro Ser Ile Gln Gln Asp Arg Val Phe Ser Tyr
465                 470                 475                 480

Asp Ile Glu Arg Leu Thr Asp Trp Leu Lys Lys Glu Ser Leu Ile Pro
            485                 490                 495

Asp His Gln Asn Lys Glu Leu Arg Gly Met Asn Ile
            500                 505

<210> SEQ ID NO 41
<211> LENGTH: 516
<212> TYPE: PRT
<213> ORGANISM: Streptomyces griseus

<400> SEQUENCE: 41

Met Asp Met His Thr Val Val Gly Thr Ser Gly Thr Thr Ala Glu
  1               5                  10                  15

Asp Val Val Ala Val Ala Arg His Gly Ala Arg Val Glu Leu Ser Ala
            20                  25                  30

Ala Ala Val Glu Ala Leu Ala Ala Ala Arg Leu Ile Val Asp Ala Leu
            35                  40                  45

Ala Ala Lys Pro Glu Pro Val Tyr Gly Val Ser Thr Gly Phe Gly Ala
            50                  55                  60

Leu Ala Ser Arg His Ile Gly Thr Glu Leu Arg Ala Gln Leu Gln Arg
 65                 70                  75                  80

Asn Ile Val Arg Ser His Ala Ala Gly Met Gly Pro Arg Val Glu Arg
            85                  90                  95

Glu Val Val Arg Ala Leu Met Phe Leu Arg Leu Lys Thr Val Ala Ser
            100                 105                 110

Gly His Thr Gly Val Arg Pro Glu Val Ala Gln Thr Met Ala Asp Val
            115                 120                 125

Leu Asn Ala Gly Ile Thr Pro Val Val His Glu Tyr Gly Ser Leu Gly
            130                 135                 140

Cys Ser Gly Asp Leu Ala Pro Leu Ser His Cys Ala Leu Thr Leu Met
145                 150                 155                 160

Gly Glu Gly Glu Ala Glu Gly Pro Asp Gly Thr Val Arg Pro Ala Gly
            165                 170                 175

Glu Leu Leu Ala Ala His Gly Ile Ala Pro Val Glu Leu Arg Glu Lys
```

```
                    180                 185                 190
Glu Gly Leu Ala Leu Leu Asn Gly Thr Asp Gly Met Leu Gly Met Leu
        195                 200                 205

Val Met Ala Leu Ala Asp Leu Arg Asn Leu Tyr Thr Ser Ala Asp Ile
210                 215                 220

Thr Ala Ala Leu Ser Leu Glu Ala Leu Leu Gly Thr Asp Lys Val Leu
225                 230                 235                 240

Ala Pro Glu Leu His Ala Ile Arg Pro His Pro Gly Gln Gly Val Ser
                245                 250                 255

Ala Asp Asn Met Ser Arg Val Leu Ala Gly Ser Gly Leu Thr Gly His
                260                 265                 270

His Gln Asp Asp Ala Pro Arg Val Gln Asp Ala Tyr Ser Val Arg Cys
            275                 280                 285

Ala Pro Gln Val Asn Gly Ala Gly Arg Asp Thr Leu Asp His Ala Ala
        290                 295                 300

Leu Val Ala Gly Arg Glu Leu Ala Ser Ser Val Asp Asn Pro Val Val
305                 310                 315                 320

Leu Pro Asp Gly Arg Val Glu Ser Asn Gly Asn Phe His Gly Ala Pro
                325                 330                 335

Val Ala Tyr Val Leu Asp Phe Leu Ala Ile Val Ala Ala Asp Leu Gly
                340                 345                 350

Ser Ile Cys Glu Arg Arg Thr Asp Arg Leu Leu Asp Lys Asn Arg Ser
            355                 360                 365

His Gly Leu Pro Pro Phe Leu Ala Asp Asp Ala Gly Val Asp Ser Gly
        370                 375                 380

Leu Met Ile Ala Gln Tyr Thr Gln Ala Ala Leu Val Ser Glu Met Lys
385                 390                 395                 400

Arg Leu Ala Val Pro Ala Ser Ala Asp Ser Ile Pro Ser Ser Ala Met
                405                 410                 415

Gln Glu Asp His Val Ser Met Gly Trp Ser Ala Ala Arg Lys Leu Arg
                420                 425                 430

Thr Ala Val Asp Asn Leu Ala Arg Ile Val Ala Val Glu Leu Tyr Ala
            435                 440                 445

Ala Thr Arg Ala Ile Glu Leu Arg Ala Ala Glu Gly Leu Thr Pro Ala
        450                 455                 460

Pro Ala Ser Glu Ala Val Ala Ala Leu Arg Ala Ala Gly Ala Glu
465                 470                 475                 480

Gly Pro Gly Pro Asp Arg Phe Leu Ala Pro Asp Leu Ala Ala Ala Asp
                485                 490                 495

Thr Phe Val Arg Glu Gly Arg Leu Val Ala Ala Val Glu Pro Val Thr
                500                 505                 510

Gly Pro Leu Ala
        515

<210> SEQ ID NO 42
<211> LENGTH: 511
<212> TYPE: PRT
<213> ORGANISM: Corynebacteriaceae sp.

<400> SEQUENCE: 42

Met Ala Ser Ala Pro Gln Ile Thr Leu Gly Leu Ser Gly Ala Thr Ala
  1               5                  10                  15

Asp Asp Val Ile Ala Val Ala Arg His Glu Ala Arg Ile Ser Ile Ser
                20                  25                  30
```

```
Pro Gln Val Leu Glu Leu Ala Ser Val Arg Ala His Ile Asp Ala
        35                  40                  45
Leu Ala Ser Ala Asp Thr Pro Val Tyr Gly Ile Ser Thr Gly Phe Gly
    50                  55                  60
Ala Leu Ala Thr Arg His Ile Ala Pro Glu Asp Arg Ala Lys Leu Gln
65                  70                  75                  80
Arg Ser Leu Ile Arg Ser His Ala Ala Gly Met Gly Glu Pro Val Glu
                85                  90                  95
Arg Glu Val Val Arg Ala Leu Met Phe Leu Arg Ala Lys Thr Leu Ala
            100                 105                 110
Ser Gly Arg Ser Val Arg Pro Val Leu Glu Thr Met Val Gly Met
        115                 120                 125
Leu Asn Ala Gly Ile Thr Pro Val Val Arg Glu Tyr Gly Ser Leu Gly
    130                 135                 140
Cys Ser Gly Asp Leu Ala Pro Leu Ser His Cys Ala Leu Val Leu Met
145                 150                 155                 160
Gly Glu Gly Glu Ala Thr Asp Ala His Gly Asp Ile Arg Pro Val Pro
                165                 170                 175
Glu Leu Phe Ala Glu Ala Gly Leu Thr Pro Val Glu Leu Ala Glu Lys
            180                 185                 190
Glu Gly Leu Ala Leu Val Asn Gly Thr Asp Gly Met Leu Gly Gln Leu
        195                 200                 205
Ile Met Ala Leu Ala Asp Leu Asp Glu Leu Leu Asp Ile Ala Asp Ala
    210                 215                 220
Thr Ala Ala Met Ser Val Glu Ala Gln Leu Gly Thr Asp Gln Val Phe
225                 230                 235                 240
Arg Ala Glu Leu His Glu Pro Leu Arg Pro His Pro Gly Gln Gly Arg
                245                 250                 255
Ser Ala Gln Asn Met Phe Ala Phe Leu Ala Asp Ser Pro Ile Val Ala
            260                 265                 270
Ser His Arg Glu Gly Asp Gly Arg Val Gln Asp Ala Tyr Ser Leu Arg
        275                 280                 285
Cys Ser Pro Gln Val Thr Gly Ala Ala Arg Asp Thr Ile Ala His Ala
    290                 295                 300
Arg Leu Val Ala Thr Arg Glu Leu Ala Ala Ile Asp Asn Pro Val
305                 310                 315                 320
Val Leu Pro Ser Gly Glu Val Thr Ser Asn Gly Asn Phe His Gly Ala
                325                 330                 335
Pro Val Ala Tyr Val Leu Asp Phe Leu Ala Ile Ala Val Ala Asp Leu
            340                 345                 350
Gly Ser Ile Ala Glu Arg Arg Thr Asp Arg Met Leu Asp Pro Ala Arg
        355                 360                 365
Ser Arg Asp Leu Pro Ala Phe Leu Ala Asp Pro Gly Val Asp Ser
    370                 375                 380
Gly Met Met Ile Ala Gln Tyr Thr Gln Ala Gly Leu Val Ala Glu Asn
385                 390                 395                 400
Lys Arg Leu Ala Val Pro Ala Val Asp Ser Ile Pro Ser Ser Ala Met
                405                 410                 415
Gln Glu Asp His Val Ser Leu Gly Trp His Ala Ala Arg Lys Leu Pro
            420                 425                 430
Thr Ser Val Ala Asn Leu Arg Arg Ile Leu Ala Val Glu Met Leu Ile
        435                 440                 445
Ala Gly Arg Ala Leu Asp Leu Arg Ala Pro Leu Lys Pro Gly Pro Ala
```

```
                450             455             460
Thr Gly Ala Val Leu Glu Val Leu Arg Ser Lys Val Ala Gly Pro Gly
465                 470                 475                 480

Gln Asp Arg Phe Leu Ser Ala Glu Leu Glu Ala Ala Tyr Asp Leu Leu
                485                 490                 495

Ala Asn Gly Ser Val His Lys Ala Leu Glu Ala His Leu Pro Glu
                500                 505                 510

<210> SEQ ID NO 43
<211> LENGTH: 513
<212> TYPE: PRT
<213> ORGANISM: Unknown Organism
<220> FEATURE:
<223> OTHER INFORMATION: Description of Unknown Organism: 983831/HAL

<400> SEQUENCE: 43

Met Ala Ser Ala Pro Gln Ile Thr Leu Gly Leu Ser Gly Ala Thr Ala
  1               5                  10                  15

Asp Asp Val Ile Ala Val Ala Arg His Glu Ala Arg Ile Ser Ile Ser
                 20                  25                  30

Pro Gln Val Leu Glu Glu Leu Ala Ser Val Arg Ala His Ile Asp Ala
             35                  40                  45

Leu Ala Ser Ala Asp Thr Pro Val Tyr Gly Ile Ser Thr Gly Phe Gly
 50                  55                  60

Ala Leu Ala Thr Arg His Ile Ala Pro Glu Asp Arg Ala Lys Leu Gln
 65                  70                  75                  80

Arg Ser Leu Ile Arg Ser His Ala Ala Gly Met Gly Glu Pro Val Glu
                 85                  90                  95

Arg Glu Val Val Arg Ala Leu Met Phe Leu Arg Ala Lys Thr Leu Ala
                100                 105                 110

Ser Gly Arg Thr Gly Val Arg Pro Val Val Leu Glu Thr Met Val Gly
             115                 120                 125

Met Leu Asn Ala Gly Ile Thr Pro Val Val Arg Glu Tyr Gly Ser Leu
130                 135                 140

Gly Cys Ser Gly Asp Leu Ala Pro Leu Ser His Cys Ala Leu Val Leu
145                 150                 155                 160

Met Gly Glu Gly Glu Ala Thr Asp Ala His Gly Asp Ile Arg Pro Val
                165                 170                 175

Pro Glu Leu Phe Ala Glu Ala Gly Leu Thr Pro Val Glu Leu Ala Glu
            180                 185                 190

Lys Glu Gly Leu Ala Leu Val Asn Gly Thr Asp Gly Met Leu Gly Gln
        195                 200                 205

Leu Ile Met Ala Leu Ala Asp Leu Asp Glu Leu Leu Asp Ile Ala Asp
210                 215                 220

Ala Thr Ala Ala Met Ser Val Glu Ala Gln Leu Gly Thr Asp Gln Val
225                 230                 235                 240

Phe Arg Ala Glu Leu His Glu Pro Leu Arg Pro His Pro Gly Gln Gly
                245                 250                 255

Arg Ser Ala Gln Asn Met Phe Ala Phe Leu Ala Asp Ser Pro Ile Val
                260                 265                 270

Ala Ser His Arg Glu Gly Asp Gly Arg Val Gln Asp Ala Tyr Ser Leu
            275                 280                 285

Arg Cys Ser Pro Gln Val Thr Gly Ala Ala Arg Asp Thr Ile Ala His
        290                 295                 300

Ala Arg Leu Val Ala Thr Arg Glu Leu Ala Ala Ala Ile Asp Asn Pro
```

-continued

```
            305                 310                 315                 320
Val Val Leu Pro Ser Gly Glu Val Thr Ser Asn Gly Asn Phe His Gly
                325                 330                 335

Ala Pro Val Ala Tyr Val Leu Asp Phe Leu Ala Ile Ala Val Ala Asp
                340                 345                 350

Leu Gly Ser Ile Ala Glu Arg Arg Thr Asp Arg Met Leu Asp Pro Ala
                355                 360                 365

Arg Ser Arg Asp Leu Pro Ala Phe Leu Ala Asp Pro Gly Val Asp
                370                 375                 380

Ser Gly Met Met Ile Ala Gln Tyr Thr Gln Ala Gly Leu Val Ala Glu
385                 390                 395                 400

Asn Lys Arg Leu Ala Val Pro Ala Ser Val Asp Ser Ile Pro Ser Ser
                405                 410                 415

Ala Met Gln Glu Asp His Val Ser Leu Gly Trp His Ala Ala Arg Lys
                420                 425                 430

Leu Arg Thr Ser Val Ala Asn Leu Arg Arg Ile Leu Ala Val Glu Met
                435                 440                 445

Leu Ile Ala Gly Arg Ala Leu Asp Leu Arg Ala Pro Leu Lys Pro Gly
            450                 455                 460

Pro Ala Thr Gly Ala Val Leu Glu Val Leu Arg Ser Lys Val Ala Gly
465                 470                 475                 480

Pro Gly Gln Asp Arg Phe Leu Ser Ala Glu Leu Ala Ala Tyr Asp
                485                 490                 495

Leu Leu Ala Asn Gly Ser Val His Lys Ala Leu Glu Ala His Leu Pro
                500                 505                 510

Ala

<210> SEQ ID NO 44
<211> LENGTH: 513
<212> TYPE: PRT
<213> ORGANISM: Streptomyces coelicolor

<400> SEQUENCE: 44

Met Ala Ser Met His Thr Val Val Gly Thr Ser Gly Val Thr Ala
 1               5                  10                  15

Ser Asp Val Leu Ala Val Ala Arg Ala Gly Ala Arg Ile Glu Leu Ser
                20                  25                  30

Glu Glu Ala Val Ala Ala Leu Ala Ala Arg Ser Val Val Asp Ala
            35                  40                  45

Leu Ala Ala Lys Pro Asp Pro Val Tyr Gly Val Ser Thr Gly Phe Gly
    50                  55                  60

Ala Leu Ala Thr Arg His Ile Ser Pro Glu Leu Arg Gly Arg Leu Gln
65                  70                  75                  80

Arg Asn Ile Val Arg Ser His Ala Ala Gly Met Gly Pro Arg Val Glu
                85                  90                  95

Arg Glu Val Val Arg Ala Leu Met Phe Leu Arg Leu Lys Thr Val Cys
                100                 105                 110

Ser Gly Arg Thr Gly Val Arg Pro Glu Val Ala Gln Thr Met Ala Asp
            115                 120                 125

Val Leu Asn Ala Gly Ile Thr Pro Val Val His Glu Tyr Gly Ser Leu
    130                 135                 140

Gly Cys Ser Gly Asp Leu Ala Pro Leu Ser His Cys Ala Leu Thr Leu
145                 150                 155                 160

Met Gly Glu Gly Asp Ala Glu Gly Pro Asp Gly Thr Val Arg Pro Ala
```

```
                    165                 170                 175
Gly Glu Leu Leu Ala Ala His Gly Ile Ala Pro Val Glu Leu Arg Glu
                180                 185                 190

Lys Glu Gly Leu Ala Leu Leu Asn Gly Thr Asp Gly Met Leu Gly Met
            195                 200                 205

Leu Val Met Ala Leu Ala Asp Leu Asp Thr Leu Tyr Lys Ser Ala Asp
        210                 215                 220

Ile Thr Ala Ala Leu Thr Met Glu Ala Leu Leu Gly Thr Asp Arg Val
225                 230                 235                 240

Leu Ala Pro Glu Leu His Ala Pro Ile Arg Pro His Pro Gly Gln Ala
                245                 250                 255

Ala Ser Ala Ala Asn Met Ala Ala Val Leu Lys Gly Ser Gly Leu Thr
            260                 265                 270

Gly His His Gln Asp Asp Ala Pro Arg Val Gln Asp Ala Tyr Ser Val
        275                 280                 285

Arg Cys Ala Pro Gln Val Gly Ala Gly Arg Asp Thr Met Ala His
        290                 295                 300

Ala Gly Leu Val Ala Glu Arg Glu Leu Ala Ala Val Asp Asn Pro
305                 310                 315                 320

Val Val Leu Pro Asp Gly Arg Val Glu Ser Asn Gly Asn Phe His Gly
                325                 330                 335

Ala Pro Val Ala Tyr Val Leu Asp Phe Leu Ala Val Ala Val Ala Asp
                340                 345                 350

Leu Gly Ser Ile Ala Glu Arg Arg Thr Asp Arg Leu Leu Asp Lys Asn
        355                 360                 365

Arg Ser His Gly Leu Pro Pro Phe Leu Ala Asp Ala Gly Val Asp
370                 375                 380

Ser Gly Leu Met Ile Ala Gln Tyr Thr Gln Ala Ala Leu Val Gly Glu
385                 390                 395                 400

Leu Lys Arg Leu Ala Val Pro Ala Ser Ala Asp Ser Ile Pro Ser Ser
                405                 410                 415

Ala Met Gln Glu Asp His Val Ser Met Gly Trp Ser Ala Ala Arg Lys
                420                 425                 430

Leu Arg Thr Ala Val Asp Asn Leu Ala Arg Val Ile Ala Val Glu Leu
        435                 440                 445

Tyr Ala Ala Thr Arg Ala Ile Gln Leu Arg Glu Gly Leu Thr Pro Ala
        450                 455                 460

Pro Ala Ser Gln Ala Val Val Glu Ala Val Arg Ala Ala Val Glu Gly
465                 470                 475                 480

Pro Gly Pro Asp Arg His Leu Ala Pro Asp Leu Ala Ala Ala Asp Ala
                485                 490                 495

Phe Val Arg Ala Gly His Leu Val Ala Ala Ala Glu Ser Val Thr Gly
                500                 505                 510

Pro

<210> SEQ ID NO 45
<211> LENGTH: 513
<212> TYPE: PRT
<213> ORGANISM: Streptomyces griseus

<400> SEQUENCE: 45

Met Met Asp Met His Thr Val Val Val Gly Thr Ser Gly Thr Thr Ala
  1               5                  10                  15

Glu Asp Val Val Ala Val Ala Arg His Gly Ala Arg Val Glu Leu Ser
```

-continued

```
                20                  25                  30
Ala Ala Ala Val Glu Ala Leu Ala Ala Arg Leu Ile Val Asp Ala
         35                  40                  45
Leu Ala Ala Lys Pro Glu Pro Val Tyr Gly Val Ser Thr Gly Phe Gly
 50                  55                  60
Ala Leu Ala Ser Arg His Ile Gly Thr Glu Leu Arg Ala Gln Leu Gln
 65                  70                  75                  80
Arg Asn Ile Val Arg Ser His Ala Ala Gly Met Gly Pro Arg Val Glu
                 85                  90                  95
Arg Glu Val Val Arg Ala Leu Met Phe Leu Arg Leu Lys Thr Val Ala
            100                 105                 110
Ser Gly His Thr Gly Val Arg Pro Glu Val Ala Gln Thr Met Ala Asp
            115                 120                 125
Val Leu Asn Ala Gly Ile Thr Pro Val Val His Glu Tyr Gly Ser Leu
130                 135                 140
Gly Cys Ser Gly Asp Leu Ala Pro Leu Ser His Cys Ala Leu Thr Leu
145                 150                 155                 160
Met Gly Glu Gly Glu Ala Glu Gly Pro Asp Gly Thr Val Arg Pro Ala
            165                 170                 175
Gly Glu Leu Leu Ala Ala His Gly Ile Ala Pro Val Glu Leu Arg Glu
            180                 185                 190
Lys Glu Gly Leu Ala Leu Leu Asn Gly Thr Asp Gly Met Leu Gly Met
            195                 200                 205
Leu Val Met Ala Leu Ala Asp Leu Arg Asn Leu Tyr Thr Ser Ala Asp
    210                 215                 220
Ile Thr Ala Ala Leu Ser Leu Glu Ala Leu Leu Gly Thr Asp Lys Val
225                 230                 235                 240
Leu Ala Pro Glu Leu His Ala Pro Ile Arg Pro His Pro Gly Gln Gly
                245                 250                 255
Val Ser Ala Asp Asn Met Ser Arg Val Leu Ala Gly Ser Gly Leu Thr
            260                 265                 270
Gly His His Gln Asp Asp Ala Pro Arg Val Gln Asp Ala Tyr Ser Val
        275                 280                 285
Arg Cys Ala Pro Gln Val Asn Gly Ala Gly Arg Asp Thr Leu Asp His
    290                 295                 300
Ala Ala Leu Val Ala Gly Arg Glu Leu Ala Ser Ser Val Asp Asn Pro
305                 310                 315                 320
Val Val Leu Pro Asp Gly Arg Val Glu Ser Asn Gly Asn Phe His Gly
                325                 330                 335
Ala Pro Val Ala Tyr Val Leu Asp Phe Leu Ala Ile Val Ala Ala Asp
            340                 345                 350
Leu Gly Ser Ile Cys Glu Arg Thr Asp Arg Leu Leu Asp Lys Asn
        355                 360                 365
Arg Ser His Gly Leu Pro Pro Phe Leu Ala Asp Ala Gly Val Asp
    370                 375                 380
Ser Gly Leu Met Ile Ala Gln Tyr Thr Gln Ala Ala Leu Val Ser Glu
385                 390                 395                 400
Met Lys Arg Leu Ala Val Pro Ala Ser Ala Asp Ser Ile Pro Ser Ser
            405                 410                 415
Ala Met Gln Glu Asp His Val Ser Met Gly Trp Ser Ala Ala Arg Lys
            420                 425                 430
Leu Arg Thr Ala Val Asp Asn Leu Ala Arg Ile Val Ala Val Glu Leu
        435                 440                 445
```

-continued

```
Tyr Ala Ala Thr Arg Ala Ile Glu Leu Arg Ala Leu Thr Pro Ala
    450                 455                 460
Pro Ala Ser Glu Ala Val Val Ala Ala Leu Arg Ala Ala Gly Ala Gly
465                 470                 475                 480
Pro Gly Pro Asp Arg Phe Leu Ala Pro Asp Leu Ala Ala Asp Thr
            485                 490                 495
Phe Val Arg Glu Gly Arg Leu Val Ala Val Glu Pro Val Thr Gly
            500                 505                 510
Pro

<210> SEQ ID NO 46
<211> LENGTH: 513
<212> TYPE: PRT
<213> ORGANISM: Deinococcus radiodurans

<400> SEQUENCE: 46

Met Ala Ser Ala Pro Gln Ile Met Ile Leu Asp Arg Asp Leu Asn Leu
1               5                   10                  15
Glu Gln Phe Ile Ser Val Val Arg His Gly Glu Gln Val Glu Leu Ser
            20                  25                  30
Ala Ala Ala Arg Glu Arg Ile Ala Arg Ala Arg Thr Val Ile Glu Gln
        35                  40                  45
Ile Val Glu Gly Asp Thr Pro Ile Tyr Gly Val Asn Thr Gly Phe Gly
    50                  55                  60
Lys Phe Glu Asn Val Gln Ile Asp Arg Ser Gln Leu Ala Gln Leu Gln
65                  70                  75                  80
His Asn Leu Ile Val Ser His Ala Ile Gly Met Gly Glu Pro Leu Pro
                85                  90                  95
Ala Glu Val Val Arg Gly Met Leu Leu Leu Arg Ala Gln Ser Leu Ser
            100                 105                 110
Leu Gly His Ser Gly Val Arg Val Glu Val Val Glu Leu Leu Leu Ala
            115                 120                 125
Leu Leu Asn Ala Asp Ala Leu Pro Val Val Pro Ser Gln Gly Ser Val
    130                 135                 140
Gly Ala Ser Gly Asp Leu Ala Pro Leu Ala His Leu Ala Leu Gly Leu
145                 150                 155                 160
Ile Gly Leu Gly Asp Ile Thr Glu Tyr Gln Gly Gln Val Arg Pro Ala
                165                 170                 175
Ala Asp Val Leu Ala Glu Leu Gly Leu Ser Pro Val Gln Leu Gln Ala
            180                 185                 190
Lys Glu Gly Leu Ala Leu Ile Asn Gly Thr Gln Leu Met Gly Ser Leu
        195                 200                 205
Leu Ala Leu Ala Leu His Asp Ala Gln Val Leu Leu Gly Thr Ala Asn
    210                 215                 220
Leu Ala Ala Met Thr Val Glu Ala Arg Tyr Gly Ser His Arg Pro
225                 230                 235                 240
Phe Gln Pro Asp Val His Val Gly Leu Arg Pro His Pro Gly Ala Leu
                245                 250                 255
Ala Val Ala Ala Glu Leu Arg Glu Phe Leu Ala Gly Ser Glu Ile Ala
            260                 265                 270
Pro Ser His Leu Thr Gly Asp Gly Lys Val Gln Asp Ala Tyr Ser Leu
        275                 280                 285
Arg Ala Val Pro Gln Val His Gly Ala Thr Trp Asp Ala Leu Ala Gln
    290                 295                 300
```

```
Ala Glu Arg Val Leu Ala Val Glu Phe Ala Ser Val Thr Asp Asn Pro
305                 310                 315                 320

Leu Ile Phe Pro Thr Gly Val Val Ser Gly Gly Asn Phe His Gly
            325                 330                 335

Gln Pro Leu Ala Val Thr Ile Asp Ala Leu Lys Val Ala Val Ala Glu
            340                 345                 350

Leu Gly Ser Ile Ser Glu Arg Arg Thr Glu Gln Leu Leu Asn Pro Ala
            355                 360                 365

Leu Ser Arg Gly Leu Pro Ala Phe Leu Thr Pro Asn Gly Gly Leu Asn
370                 375                 380

Ser Gly Phe Met Ile Ala Gln Tyr Thr Ser Ala Leu Val Ser Glu
385                 390                 395                 400

Asn Lys Val Leu Ser His Pro Ala Ser Val Asp Ser Ile Pro Thr Ser
            405                 410                 415

Ala Asn Gln Glu Asp His Val Ser Met Gly Ala His Ala Ala Arg Gln
            420                 425                 430

Leu Arg Gln Ile Val Ala Asn Val Gln Thr Val Leu Ser Ile Glu Leu
            435                 440                 445

Leu Cys Ala Ala Gln Gly Leu Asp Phe Gln Gln Pro Leu Arg Ala Gly
450                 455                 460

Arg Gly Val Gln Ala Ala Tyr Glu Tyr Val Arg Thr Phe Val Pro Thr
465                 470                 475                 480

Leu Thr Glu Asp Arg Tyr Phe Arg Pro Asp Leu Leu Arg Leu Arg Gly
            485                 490                 495

Glu Leu Val Ser Gly Arg Val Ala Gln Ala Ala Asp Thr Gln Ala Pro
            500                 505                 510

Ala

<210> SEQ ID NO 47
<211> LENGTH: 513
<212> TYPE: PRT
<213> ORGANISM: Agrobacterium rhizogenes

<400> SEQUENCE: 47

Met Ala Ser Ala Pro Gln Ile Thr Leu Gly Leu Ser Gly Val Pro Leu
1               5                   10                  15

His His Leu Ala Asp Ile Tyr Trp Asn Asn Gly Ser Ala Lys Leu Asp
            20                  25                  30

Pro Ser Phe Asp Ala Ala Val Leu Lys Gly Ala Ala Arg Ile Ala Glu
            35                  40                  45

Ile Ala Ala Gly Asn Ala Pro Val Tyr Gly Ile Asn Thr Gly Phe Gly
        50                  55                  60

Lys Leu Ala Ser Ile Lys Ile Asp Ala Asp Leu Ala Thr Leu Gln
65                  70                  75                  80

Arg Asn Leu Ile Leu Ser His Cys Cys Gly Val Gly Ala Pro Leu Pro
                85                  90                  95

Glu Asn Val Val Arg Leu Ile Met Ala Leu Lys Leu Ile Ser Leu Gly
            100                 105                 110

Arg Gly Ala Ser Gly Val Arg Ile Glu Leu Ile Arg Leu Ile Glu Gly
            115                 120                 125

Met Leu Glu Lys Gly Val Ile Pro Val Pro Glu Lys Gly Ser Val
130                 135                 140

Gly Ala Ser Gly Asp Leu Ala Pro Leu Ala His Met Ser Ala Thr Met
145                 150                 155                 160
```

```
Met Gly Glu Gly Glu Ala Phe Asp Tyr Gln Gly Val Gln Met Pro Ser
            165                 170                 175

Lys Asp Ala Leu Ala Lys Ala Gly Leu Ser Pro Val Leu Ala Ala
        180                 185                 190

Lys Glu Gly Leu Ala Leu Ile Asn Gly Thr Gln Thr Ser Thr Ala Leu
    195                 200                 205

Ala Leu Ala Gly Leu Phe Arg Ala His Arg Ala Ala Gln Ser Ala Leu
    210                 215                 220

Val Thr Gly Ala Leu Ser Thr Asp Ala Met Gly Ser Ser Ala Pro
225                 230                 235                 240

Phe His Pro Asp Ile His Thr Pro Leu Arg Gly His Lys Gly Gln Ile
                245                 250                 255

Asp Ala Gly Ser Ala Leu Arg Asn Leu Leu Gln Gly Ser Glu Ile Arg
                260                 265                 270

Glu Ser His Ile Glu Gly Asp Glu Arg Val Gln Asp Pro Tyr Cys Ile
            275                 280                 285

Arg Cys Gln Pro Gln Val Asp Gly Ala Cys Leu Asp Leu Leu Ala Ser
    290                 295                 300

Val Ala Arg Thr Leu Glu Ile Glu Ala Asn Ala Val Thr Asp Asn Pro
305                 310                 315                 320

Leu Val Leu Ser Asp Asn Ser Val Val Ser Gly Gly Asn Phe His Ala
                325                 330                 335

Glu Pro Val Ala Phe Ala Ala Asp Gln Thr Ala Leu Ala Val Cys Glu
            340                 345                 350

Ile Gly Ala Ile Ala Gln Arg Arg Ile Ala Leu Leu Val Asp Pro Ala
            355                 360                 365

Leu Ser Tyr Gly Leu Pro Ala Phe Leu Ser Lys Lys Pro Gly Leu Asn
        370                 375                 380

Ser Gly Leu Met Ile Ala Glu Val Thr Ser Ala Ala Leu Met Ser Glu
385                 390                 395                 400

Asn Lys Gln Met Ser His Pro Ala Ser Val Asp Ser Thr Pro Thr Ser
                405                 410                 415

Ala Asn Gln Glu Asp His Val Ser Met Ala Cys His Gly Ala Arg Arg
                420                 425                 430

Leu Leu Ala Met Thr Asp Asn Leu Phe Gly Ile Leu Gly Ile Glu Ala
            435                 440                 445

Leu Ala Ala Val Gln Gly Val Glu Leu Arg Gly Pro Leu Lys Thr Ser
    450                 455                 460

Pro Glu Leu Glu Lys Ala Ala Val Leu Arg Ser Ala Val Pro Val
465                 470                 475                 480

Leu Glu Asp Asp Arg Tyr Met Ala Thr Asp Leu Lys Ala Ala Ile Glu
                485                 490                 495

Val Val Ala Ser Gly Ala Leu Val Ser Ala Ile Ser Ser Gly Leu Pro
            500                 505                 510

Val

<210> SEQ ID NO 48
<211> LENGTH: 513
<212> TYPE: PRT
<213> ORGANISM: Agrobacterium rhizogenes

<400> SEQUENCE: 48

Met Ala Ser Ala Pro Gln Ile Thr Leu Gly Leu Ser Gly Val Pro Leu
  1               5                  10                  15
```

-continued

```
His His Leu Ala Asp Ile Tyr Trp Asn Asn Gly Ser Ala Lys Leu Asp
             20                  25                  30

Pro Ser Phe Asp Ala Ala Val Leu Lys Gly Ala Ala Arg Ile Ala Glu
         35                  40                  45

Ile Ala Ala Gly Asn Ala Pro Val Tyr Gly Ile Asn Thr Gly Phe Gly
     50                  55                  60

Lys Leu Ala Ser Ile Lys Ile Asp Ala Ala Asp Leu Ala Thr Leu Gln
 65                  70                  75                  80

Arg Asn Leu Ile Leu Ser His Cys Cys Gly Val Gly Ala Pro Leu Pro
                 85                  90                  95

Glu Asn Val Val Arg Leu Ile Met Ala Leu Lys Leu Ile Ser Leu Gly
            100                 105                 110

Arg Gly Ala Ser Gly Val Arg Ile Glu Leu Ile Arg Leu Ile Glu Gly
        115                 120                 125

Met Leu Glu Lys Gly Val Ile Pro Val Ile Pro Glu Lys Gly Ser Val
    130                 135                 140

Gly Ala Ser Gly Asp Leu Ala Pro Leu Ala His Met Ser Ala Thr Met
145                 150                 155                 160

Met Gly Glu Gly Glu Ala Phe Asp Tyr Gln Gly Val Gln Met Pro Ser
                165                 170                 175

Lys Asp Ala Leu Ala Lys Ala Gly Leu Ser Pro Val Val Leu Ala Ala
            180                 185                 190

Lys Glu Gly Leu Ala Leu Ile Asn Gly Thr Gln Thr Ser Thr Ala Leu
        195                 200                 205

Ala Leu Ala Gly Leu Phe Arg Ala His Arg Ala Ala Gln Ser Ala Leu
    210                 215                 220

Val Thr Gly Ala Leu Ser Thr Asp Ala Ala Met Gly Ser Ser Ala Pro
225                 230                 235                 240

Phe His Pro Asp Ile His Thr Pro Leu Arg Gly His Lys Gly Gln Ile
                245                 250                 255

Asp Ala Gly Ser Ala Leu Arg Asn Leu Leu Gln Gly Ser Glu Ile Arg
            260                 265                 270

Glu Ser His Ile Glu Gly Asp Glu Arg Val Gln Asp Pro Tyr Cys Ile
        275                 280                 285

Arg Cys Gln Pro Gln Val Asp Gly Ala Cys Leu Asp Leu Leu Ala Ser
    290                 295                 300

Val Ala Arg Thr Leu Glu Ile Glu Ala Asn Ala Val Thr Asp Asn Pro
305                 310                 315                 320

Leu Val Leu Ser Asp Asn Ser Val Val Ser Gly Gly Asn Phe His Ala
                325                 330                 335

Glu Pro Val Ala Phe Ala Ala Asp Gln Thr Ala Leu Ala Val Cys Glu
            340                 345                 350

Ile Gly Ala Ile Ala Gln Arg Arg Ile Ala Leu Leu Val Asp Pro Ala
        355                 360                 365

Leu Ser Tyr Gly Leu Pro Ala Phe Leu Ser Lys Lys Pro Gly Leu Asn
    370                 375                 380

Ser Gly Leu Met Ile Ala Glu Val Thr Ser Ala Ala Leu Met Ser Glu
385                 390                 395                 400

Asn Lys Gln Met Ser His Pro Ala Ser Val Asp Ser Thr Pro Thr Ser
                405                 410                 415

Ala Asn Gln Glu Asp His Val Ser Met Ala Cys His Gly Ala Arg Arg
            420                 425                 430
```

-continued

```
Leu Leu Ala Met Thr Asp Asn Leu Phe Gly Ile Leu Gly Ile Glu Ala
        435                 440                 445

Leu Ala Ala Val Gln Gly Val Glu Leu Arg Gly Pro Leu Lys Thr Ser
        450                 455                 460

Pro Glu Leu Glu Lys Ala Ala Val Leu Arg Ser Ala Val Pro Val
465                 470                 475                 480

Leu Glu Asp Asp Arg Tyr Met Ala Thr Asp Leu Lys Ala Ala Ile Glu
        485                 490                 495

Val Val Ala Ser Gly Ala Leu Val Ser Ala Ile Ser Ser Gly Leu Pro
        500                 505                 510

Val

<210> SEQ ID NO 49
<211> LENGTH: 513
<212> TYPE: PRT
<213> ORGANISM: Bacillus subtilis

<400> SEQUENCE: 49

Met Ala Ser Ala Pro Met Val Thr Leu Asp Gly Ser Ser Leu Thr Thr
  1               5                  10                  15

Ala Asp Val Ala Arg Val Leu Phe Asp Phe Glu Ala Ala Ala Ser
                20                  25                  30

Glu Glu Ser Met Glu Arg Val Lys Lys Ser Arg Ala Ala Val Glu Arg
        35                  40                  45

Ile Val Arg Asp Glu Lys Thr Ile Tyr Gly Ile Asn Thr Gly Phe Gly
        50                  55                  60

Lys Phe Ser Asp Val Leu Ile Gln Lys Glu Asp Ser Ala Ala Leu Gln
 65                 70                  75                  80

Leu Asn Leu Ile Leu Ser His Ala Cys Gly Val Gly Asp Pro Phe Pro
                85                  90                  95

Glu Cys Val Ser Arg Ala Met Leu Leu Leu Arg Ala Asn Ala Leu Leu
                100                 105                 110

Lys Gly Phe Ser Gly Val Arg Ala Glu Leu Ile Glu Gln Leu Leu Ala
        115                 120                 125

Phe Leu Asn Lys Arg Val His Pro Val Ile Pro Gln Gln Gly Ser Leu
        130                 135                 140

Gly Ala Ser Gly Asp Leu Ala Pro Leu Ser His Leu Ala Leu Ala Leu
145                 150                 155                 160

Ile Gly Gln Gly Glu Val Phe Asp Phe Glu Gly Glu Arg Met Pro Ala
                165                 170                 175

Met Thr Gly Leu Lys Lys Ala Gly Ile Gln Pro Val Thr Leu Thr Ser
        180                 185                 190

Lys Glu Gly Leu Ala Leu Ile Asn Gly Thr Gln Ala Met Thr Ala Met
        195                 200                 205

Gly Val Val Ala Tyr Ile Glu Ala Glu Lys Leu Ala Tyr Gln Thr Glu
        210                 215                 220

Arg Ile Ala Ser Leu Thr Ile Glu Gly Leu Gln Gly Ile Ile Asp Ala
225                 230                 235                 240

Phe Asp Glu Asp Ile His Leu Ala Leu Arg Gly Tyr Gln Glu Gln Ile
                245                 250                 255

Asp Val Ala Glu Arg Ile Arg Phe Tyr Leu Ser Asp Ser Gly Leu Thr
        260                 265                 270

Thr Ser His Arg Gln Gly Glu Leu Arg Val Gln Asp Ala Tyr Ser Leu
        275                 280                 285
```

-continued

```
Arg Cys Ile Pro Gln Val His Gly Ala Thr Trp Gln Thr Leu Gly Tyr
    290                 295                 300

Val Lys Glu Lys Leu Glu Ile Glu Met Asn Ala Ala Thr Asp Asn Pro
305                 310                 315                 320

Leu Ile Phe Asn Asp Gly Asp Val Ile Ser Gly Gly Asn Phe His Gly
                325                 330                 335

Gln Pro Ile Ala Phe Ala Met Asp Phe Leu Lys Ile Ala Ile Ser Glu
            340                 345                 350

Leu Ala Asn Ile Ala Glu Arg Arg Ile Glu Arg Leu Val Asn Pro Gln
        355                 360                 365

Leu Asn Arg Asp Leu Pro Pro Phe Leu Ser Pro His Pro Gly Leu Gln
    370                 375                 380

Ser Gly Ala Met Ile Met Gln Tyr Ala Ala Ser Leu Val Ser Glu
385                 390                 395                 400

Asn Lys Thr Leu Ala His Pro Ala Ser Val Asp Ser Ile Pro Ser Ser
                405                 410                 415

Ala Asn Gln Glu Asp His Val Ser Met Gly Thr Ile Ala Ala Arg His
            420                 425                 430

Ala Tyr Gln Val Ile Ala Asn Thr Arg Arg Val Ile Ala Ile Glu Ala
        435                 440                 445

Ile Cys Ala Leu Gln Ala Val Glu Tyr Arg Gly Ile Glu His Ala Ala
    450                 455                 460

Ser Tyr Thr Lys Gln Leu Phe Gln Glu Met Arg Lys Val Val Pro Ser
465                 470                 475                 480

Ile Gln Gln Asp Arg Val Phe Ser Tyr Asp Ile Glu Arg Leu Thr Asp
                485                 490                 495

Trp Leu Lys Lys Glu Ser Leu Ile Pro Asp His Gln Asn Lys Glu Leu
            500                 505                 510

Arg
```

<210> SEQ ID NO 50
<211> LENGTH: 513
<212> TYPE: PRT
<213> ORGANISM: Vibrio cholerae

<400> SEQUENCE: 50

```
Met Ala Ser Met Leu His Leu Met Ile Lys Pro Gly Gln Leu Ser Leu
  1               5                  10                  15

Lys Gln Leu Arg Gln Val Ser Arg Ser Pro Val Val Leu Ser Leu Asp
                20                  25                  30

Pro Glu Ala Ile Pro Ala Ile Ala Glu Ser Ala Gln Val Val Glu Gln
            35                  40                  45

Val Ile Ser Glu Gly Arg Thr Val Tyr Gly Ile Asn Thr Gly Phe Gly
        50                  55                  60

Leu Leu Ala Asn Thr Lys Ile Ala Pro Gln Asp Leu Glu Thr Leu Gln
 65                  70                  75                  80

Lys Ser Ile Val Leu Ser His Ala Ala Gly Ile Gly Glu Leu Met Ser
                85                  90                  95

Asp Glu Thr Val Arg Leu Met Met Leu Leu Lys Ile Asn Ser Leu Ala
                100                 105                 110

Arg Gly Tyr Ser Gly Ile Arg Leu Glu Val Ile Gln Ala Leu Ile Glu
            115                 120                 125

Leu Val Asn Asn Gln Ile Tyr Pro Cys Val Pro Lys Lys Gly Ser Val
        130                 135                 140
```

-continued

```
Gly Ala Ser Gly Asp Leu Ala Pro Leu Ala His Met Ser Thr Val Leu
145                 150                 155                 160

Leu Gly Glu Gly Gln Ala Arg Asp Tyr Asn Gly Lys Ile Ile Ser Gly
            165                 170                 175

Leu Glu Ala Met Lys Ile Ala Gly Leu Glu Pro Ile Thr Leu Ala Pro
        180                 185                 190

Lys Glu Gly Leu Ala Leu Leu Asn Gly Thr Gln Ala Ser Thr Ala Phe
    195                 200                 205

Ala Leu Glu Gly Leu Phe Val Ala Glu Asp Leu Phe Ala Ser Ala Thr
210                 215                 220

Val Cys Gly Ala Met Ser Val Glu Ala Ala Leu Gly Ser Arg Arg Pro
225                 230                 235                 240

Phe Asp Pro Arg Ile His Arg Pro Val Arg Gly His Arg Thr Gln Met
                245                 250                 255

Asp Ala Ala Thr Ala Tyr Arg His Leu Leu Val Ser Ser Glu Ile Gly
            260                 265                 270

Gln Ser His Ser Asn Cys Glu Gly Lys Val Gln Asp Pro Tyr Ser Leu
        275                 280                 285

Arg Cys Gln Pro Gln Val Met Gly Ala Cys Leu Gln Gln Ile Arg Ser
    290                 295                 300

Ala Ala Glu Val Leu Glu Val Glu Ala Asn Ser Val Ser Asp Asn Pro
305                 310                 315                 320

Leu Val Phe Ala Asp Gly Asp Ile Ile Ser Gly Gly Asn Phe His Ala
                325                 330                 335

Glu Pro Val Ala Met Ala Ala Asp Asn Leu Ala Leu Ala Ile Ala Glu
            340                 345                 350

Ile Gly Ser Leu Ser Glu Arg Arg Met Ala Leu Leu Ile Asp Ser Ala
        355                 360                 365

Leu Ser Lys Asp Leu Pro Pro Phe Leu Val Asp Asn Gly Gly Val Asn
370                 375                 380

Ser Gly Phe Met Ile Ala Gln Val Thr Ala Ala Leu Ala Ser Glu
385                 390                 395                 400

Asn Lys Thr Leu Ala His Pro Ala Ser Val Asp Ser Leu Pro Thr Ser
                405                 410                 415

Ala Asn Gln Glu Asp His Val Ser Met Ala Thr Phe Ala Ala Arg Arg
            420                 425                 430

Leu Arg Asp Met Gly Glu Asn Thr Arg Gly Ile Leu Ala Val Glu Tyr
        435                 440                 445

Leu Ala Ala Gln Gly Leu Asp Phe Arg Ala Pro Leu Lys Ser Ser
    450                 455                 460

Pro Arg Ile Glu Glu Ala Arg Gln Ile Leu Arg Glu Lys Val Pro Phe
465                 470                 475                 480

Tyr Asp Lys Asp Arg Tyr Phe Ala Pro Asp Ile Glu Lys Ala Asn Ala
                485                 490                 495

Leu Leu Ala Gln Leu Ala Val His Asn Arg Leu Met Pro Asp Gln Leu
            500                 505                 510

Leu
```

<210> SEQ ID NO 51
<211> LENGTH: 513
<212> TYPE: PRT
<213> ORGANISM: Pseudomonas aeruginosa

<400> SEQUENCE: 51

-continued

```
Met Ala Ser Ala Met Ser Leu His Leu Lys Pro Gly Gln Leu Thr Leu
 1               5                  10                  15

Ala Asp Leu Arg Gln Ala Tyr Leu Ala Pro Val Arg Leu Ser Leu Asp
            20                  25                  30

Pro Ser Ala Asp Ala Pro Ile Ala Ser Val Ala Cys Val Glu Asn
        35                  40                  45

Ile Ile Ala Glu Gly Arg Thr Ala Tyr Gly Ile Asn Thr Gly Phe Gly
     50                  55                  60

Leu Leu Ala Ser Thr Arg Ile Ser Pro Ala Asp Leu Glu Lys Leu Gln
 65              70                  75                  80

Arg Ser Ile Val Leu Ser His Ala Ala Gly Val Gly Glu Ala Leu Asp
                85                  90                  95

Asp Ala Met Val Arg Leu Val Met Leu Leu Lys Val Asn Ser Leu Ala
            100                 105                 110

Arg Gly Phe Ser Gly Ile Arg Arg Lys Val Ile Asp Ala Leu Ile Ala
            115                 120                 125

Leu Ile Asn Ala Glu Val Tyr Pro His Ile Pro Leu Lys Gly Ser Val
     130                 135                 140

Gly Ala Ser Gly Asp Leu Ala Pro Leu Ala His Met Ser Leu Val Leu
145                 150                 155                 160

Ile Gly Glu Ser Arg Ala Arg His Ala Arg Gly Glu Trp Leu Pro Ala
                165                 170                 175

Ala Glu Ala Leu Ala Val Ala Gly Leu Glu Pro Leu Thr Leu Ala Ala
            180                 185                 190

Lys Glu Gly Leu Ala Leu Leu Asn Gly Thr Gln Val Ser Thr Ala Tyr
            195                 200                 205

Ala Leu Arg Gly Leu Phe Glu Ala Glu Asp Leu Phe Ala Ala Ala Thr
     210                 215                 220

Val Cys Gly Gly Leu Ser Val Glu Ala Met Leu Gly Ser Arg Ala Pro
225                 230                 235                 240

Phe Asp Ala Arg Ile His Ala Ala Leu Arg Gly Gln Arg Gly Gln Ile
                245                 250                 255

Asp Val Ala Ala Ala Tyr Arg Asp Leu Leu Ala Ser Ser Glu Val Ala
            260                 265                 270

Arg Ser His Glu Lys Cys Asp Gly Lys Val Gln Asp Pro Tyr Ser Leu
            275                 280                 285

Arg Cys Gln Pro Gln Val Met Gly Ala Cys Leu Thr Gln Met Arg Gln
     290                 295                 300

Ala Ala Glu Val Leu Glu Ile Glu Ala Asn Ala Val Ser Asp Asn Pro
305                 310                 315                 320

Leu Val Phe Ala Ala Gly Asp Val Ile Ser Gly Gly Asn Phe His Ala
                325                 330                 335

Glu Pro Val Ala Met Ala Ala Asp Asn Leu Ala Leu Ala Leu Ala Glu
            340                 345                 350

Ile Gly Ser Leu Ser Glu Arg Arg Ile Ser Leu Met Met Asp Met His
            355                 360                 365

Met Ser Gln Asp Leu Pro Pro Phe Leu Val Ala Asn Gly Gly Val Asn
     370                 375                 380

Ser Gly Phe Met Ile Ala Gln Val Thr Ala Ala Leu Ala Ser Asp
385                 390                 395                 400

Asn Lys Ala Leu Ala His Pro Ala Ser Val Asp Ser Leu Pro Thr Ser
                405                 410                 415

Ala Asn Gln Glu Asp His Val Ser Met Ala Pro Asn Ala Gly Lys Arg
```

-continued

```
                420                 425                 430
Leu Trp Ala Met Ala Glu Asn Val Arg Gly Ile Leu Ala Val Glu Trp
            435                 440                 445
Leu Gly Ala Cys Gln Gly Leu Asp Phe Arg Glu Gly Leu Lys Ser Ser
        450                 455                 460
Pro Lys Leu Glu Gln Ala Arg Arg Leu Leu Arg Asp Lys Val Pro Tyr
465                 470                 475                 480
Tyr Gln Glu Asp Arg Phe Phe Ala Pro Asp Ile Glu Ala Ala Ser Gln
                485                 490                 495
Leu Leu Ala Ser Gly Cys Leu Asn Ala Leu Leu Pro Ala Arg Leu Leu
            500                 505                 510
Pro

<210> SEQ ID NO 52
<211> LENGTH: 513
<212> TYPE: PRT
<213> ORGANISM: Bacillus halodurans

<400> SEQUENCE: 52

Met Ala Met Thr Asn Leu Lys Leu Leu Asp Gly Arg Ser Leu Ser Leu
 1               5                  10                  15
His Asp Leu His Arg Ile Ile Tyr Glu Gly Glu Thr Val Gly Ala Ser
                20                  25                  30
Asp Glu Ser Met Glu Lys Val Lys Gln Ser Arg Lys Ala Val Glu Gln
            35                  40                  45
Ile Val Ala Asp Glu Lys Ile Ile Tyr Gly Ile Thr Thr Gly Phe Gly
        50                  55                  60
Lys Phe Ser Asp Ile Phe Ile Asp Pro Asp Asp Val Glu Asn Leu Gln
65                  70                  75                  80
His Asn Leu Ile Tyr Ser His Ala Cys Gly Val Gly Ser Pro Phe Pro
                85                  90                  95
Glu Thr Val Ser Arg Thr Met Leu Val Leu Arg Ala Asn Ala Leu Leu
                100                 105                 110
Lys Gly Phe Ser Gly Val Arg Pro Leu Val Ile Glu Arg Leu Leu Ala
            115                 120                 125
Leu Val Asn Ala Asn Ile His Pro Val Ile Pro Gln Gln Gly Ser Leu
        130                 135                 140
Gly Ala Ser Gly Asp Leu Ala Pro Leu Ser His Leu Ala Leu Val Leu
145                 150                 155                 160
Leu Gly Glu Gly Glu Val Phe Asp Tyr Lys Gly Thr Lys Thr Lys Ala
                165                 170                 175
Ser Phe Ala Leu Lys Glu Glu Ile Glu Pro Ile Thr Leu Thr Ala
                180                 185                 190
Lys Glu Gly Leu Ala Leu Ile Asn Gly Thr Gln Ala Met Thr Ala Met
            195                 200                 205
Gly Val Ile Ala Tyr Leu Glu Ala Glu Lys Leu Ala Phe Gln Ser Glu
        210                 215                 220
Ile Ile Ala Ser Leu Thr Met Glu Gly Leu Arg Gly Ile Ile Asp Ala
225                 230                 235                 240
Phe Asp Glu Gln Ile His Phe Ala Leu Arg Gly Tyr Val Glu Gln Val
                245                 250                 255
Asp Val Ala Arg Arg Met Glu Ser Tyr Leu Gln Asp Ser Gln Leu Thr
            260                 265                 270
Thr Ser His Arg Gln Gly Glu Leu Arg Val Gln Asp Ala Tyr Ser Leu
```

```
                275                 280                 285
Arg Cys Ile Pro Gln Val His Gly Ala Thr Trp Gln Thr Leu Arg Tyr
        290                 295                 300

Val Lys Glu Lys Leu Glu Ile Glu Met Asn Ala Ala Thr Asp Asn Pro
305                 310                 315                 320

Leu Ile Phe Asp Asn Gly Gln Val Ile Ser Gly Gly Asn Phe His Gly
                325                 330                 335

Gln Gln Ile Ala Leu Ala Met Asp Phe Leu Gly Ile Ala Met Ala Glu
                340                 345                 350

Leu Ala Asn Ile Ser Glu Arg Arg Ile Glu Arg Leu Val Asn Pro Gln
                355                 360                 365

Leu Asn Arg Asp Leu Pro Pro Phe Leu Ser Ala Ala Pro Gly Val Gln
370                 375                 380

Ser Gly Val Met Ile Leu Gln Tyr Cys Ala Ala Ser Leu Val Ser Glu
385                 390                 395                 400

Asn Lys Thr Leu Ala His Pro Ala Ser Val Asp Ser Ile Pro Ser Ser
                405                 410                 415

Ala Asn Gln Glu Asp His Val Ser Met Gly Thr Ile Gly Ser Arg His
                420                 425                 430

Ala Tyr Gln Ile Ile Gln Asn Val Arg Asn Val Leu Ala Ile Glu Leu
                435                 440                 445

Ile Cys Ala Met Gln Ala Val Asp Ile Arg Gly Arg Glu Lys Met Ala
        450                 455                 460

Ser Phe Thr Lys Lys Ile Leu Glu Lys Gly Arg Glu His Val Pro Tyr
465                 470                 475                 480

Ile Asp Gln Asp Arg Met Phe Ala Lys Asp Ile Glu Arg Ala Ala Lys
                485                 490                 495

Trp Leu Lys Asp Gly Ser Trp Asp Phe Thr Lys Met Arg Glu Lys Glu
                500                 505                 510

Arg
```

<210> SEQ ID NO 53
<211> LENGTH: 513
<212> TYPE: PRT
<213> ORGANISM: Pseudomonas putida

<400> SEQUENCE: 53

```
Met Ala Ser Ala Thr Glu Leu Thr Leu Lys Pro Gly Thr Leu Thr Leu
  1               5                  10                  15

Ala Gln Leu Arg Ala Ile His Ala Ala Pro Val Arg Leu Gln Leu Asp
                 20                  25                  30

Ala Ser Ala Ala Pro Ala Ile Asp Ala Ser Val Ala Cys Val Glu Gln
            35                  40                  45

Ile Ile Ala Glu Asp Arg Thr Ala Tyr Gly Ile Asn Thr Gly Phe Gly
        50                  55                  60

Leu Leu Ala Ser Thr Arg Ile Ala Ser His Asp Leu Glu Asn Leu Gln
 65                  70                  75                  80

Arg Ser Leu Val Leu Ser His Ala Ala Gly Ile Gly Ala Pro Leu Asp
                 85                  90                  95

Asp Asp Leu Val Arg Leu Ile Met Val Leu Lys Ile Asn Ser Leu Ser
                100                 105                 110

Arg Gly Phe Ser Gly Ile Arg Arg Lys Val Ile Asp Ala Leu Ile Ala
            115                 120                 125

Leu Val Asn Ala Glu Val Tyr Pro His Ile Pro Leu Lys Gly Ser Val
```

```
            130                 135                 140
Gly Ala Ser Gly Asp Leu Ala Pro Leu Ala His Met Ser Leu Val Leu
145                 150                 155                 160

Leu Gly Glu Gly Lys Ala Arg Asp Tyr Lys Gly Gln Trp Leu Ser Ala
                165                 170                 175

Thr Glu Ala Leu Ala Val Ala Gly Leu Glu Pro Leu Thr Leu Ala Ala
                180                 185                 190

Lys Glu Gly Leu Ala Leu Leu Asn Gly Thr Gln Ala Ser Thr Ala Tyr
                195                 200                 205

Ala Leu Arg Gly Leu Phe Tyr Ala Glu Asp Leu Tyr Ala Ala Ile
210                 215                 220

Ala Cys Gly Gly Leu Ser Val Glu Ala Val Leu Gly Ser Arg Ser Pro
225                 230                 235                 240

Phe Asp Ala Arg Ile His Glu Ala Leu Arg Gly Gln Arg Gly Gln Ile
                245                 250                 255

Asp Thr Ala Ala Cys Phe Arg Asp Leu Leu Gly Asp Ser Ser Glu Val
                260                 265                 270

Ser Ser His Lys Asn Cys Asp Gly Lys Val Gln Asp Pro Tyr Ser Leu
                275                 280                 285

Arg Cys Gln Pro Gln Val Met Gly Ala Cys Leu Thr Gln Leu Arg Gln
290                 295                 300

Ala Ala Glu Val Leu Gly Ile Glu Ala Asn Ala Val Ser Asp Asn Pro
305                 310                 315                 320

Leu Val Phe Ala Ala Gly Asp Val Ile Ser Gly Asn Phe His Ala
                325                 330                 335

Glu Pro Val Ala Met Ala Ala Asp Asn Leu Ala Leu Ala Ile Ala Glu
                340                 345                 350

Ile Gly Ser Leu Ser Glu Arg Arg Ile Ser Leu Met Met Asp Lys His
                355                 360                 365

Met Ser Gln Asp Leu Pro Pro Phe Leu Val Glu Asn Gly Gly Val Asn
                370                 375                 380

Ser Gly Phe Met Ile Ala Gln Val Thr Ala Ala Leu Ala Ser Glu
385                 390                 395                 400

Asn Lys Ala Leu Ser His Pro His Ser Val Asp Ser Leu Pro Thr Ser
                405                 410                 415

Ala Asn Gln Glu Asp His Val Ser Met Ala Pro Ala Gly Lys Arg
                420                 425                 430

Leu Trp Glu Met Ala Glu Asn Thr Arg Gly Val Leu Ala Ile Glu Trp
                435                 440                 445

Leu Gly Ala Cys Gln Gly Leu Asp Leu Arg Lys Gly Leu Lys Thr Ser
450                 455                 460

Ala Lys Leu Glu Lys Ala Arg Gln Ala Leu Arg Ser Glu Val Ala His
465                 470                 475                 480

Tyr Asp Arg Asp Arg Phe Phe Ala Pro Asp Ile Glu Lys Ala Val Glu
                485                 490                 495

Leu Leu Ala Lys Gly Ser Leu Thr Gly Leu Leu Pro Ala Gly Leu Pro
                500                 505                 510

Ser

<210> SEQ ID NO 54
<211> LENGTH: 513
<212> TYPE: PRT
<213> ORGANISM: Rhizobium meliloti
```

<400> SEQUENCE: 54

```
Met Ala Ser Ala Pro Gln Ile Thr Leu Arg Pro Gly Ser Val Pro Leu
 1               5                  10                  15
Ser Asp Leu Glu Thr Ile Tyr Trp Thr Gly Ala Pro Ala Arg Leu Asp
                20                  25                  30
Ala Ala Phe Asp Ala Gly Ile Ala Lys Ala Ala Arg Ile Ala Glu
                35                  40                  45
Ile Val Ala Gly Asn Ala Pro Val Tyr Gly Ile Asn Thr Gly Phe Gly
     50                  55                  60
Lys Leu Ala Ser Ile Lys Ile Asp Ser Ser Asp Val Ala Thr Leu Gln
 65                  70                  75                  80
Arg Asn Leu Ile Leu Ser His Cys Cys Gly Val Gly Gln Pro Leu Thr
                85                  90                  95
Glu Asp Ile Val Arg Leu Ile Met Ala Leu Lys Leu Ile Ser Leu Gly
                100                 105                 110
Arg Gly Ala Ser Gly Val Arg Leu Glu Leu Val Arg Leu Ile Glu Ala
            115                 120                 125
Met Leu Asp Lys Gly Val Ile Pro Leu Ile Pro Glu Lys Gly Ser Val
    130                 135                 140
Gly Ala Ser Gly Asp Leu Ala Pro Leu Ala His Met Ala Ala Val Met
145                 150                 155                 160
Met Gly His Gly Glu Ala Phe Phe Ala Gly Glu Arg Met Lys Gly Asp
                165                 170                 175
Ala Ala Leu Lys Ala Glu Ala Gly Leu Ser Pro Val Thr Leu Ala Ala
                180                 185                 190
Lys Glu Gly Leu Ala Leu Ile Asn Gly Thr Gln Val Ser Thr Ala Leu
            195                 200                 205
Ala Leu Ala Gly Leu Phe Arg Ala His Arg Ala Gly Gln Ala Ala Leu
    210                 215                 220
Ile Thr Gly Ala Leu Ser Thr Asp Ala Ala Met Gly Ser Ser Ala Pro
225                 230                 235                 240
Phe His Pro Asp Ile Gln His Cys Ala Ala Ile Arg Ala Arg Ser Thr
                245                 250                 255
Arg Ala Ala Ala Asn Leu Arg Gln Leu Leu Thr Gly Ser Pro Ile Arg
            260                 265                 270
Gln Ser His Ile Glu Gly Asp Glu Arg Val Gln Asp Pro Tyr Cys Ile
    275                 280                 285
Arg Cys Gln Pro Gln Val Asp Gly Ala Cys Leu Asp Leu Leu Arg Ser
290                 295                 300
Val Ala Ala Thr Leu Thr Ile Glu Ala Asn Ala Val Thr Asp Asn Pro
305                 310                 315                 320
Leu Val Leu Ser Asp Asn Ser Val Ser Gly Gly Asn Phe His Ala
                325                 330                 335
Glu Pro Val Ala Phe Ala Ala Asp Gln Ile Ala Leu Ala Val Cys Glu
                340                 345                 350
Ile Gly Ala Ile Ser Gln Arg Arg Ile Ala Leu Leu Val Asp Pro Ala
            355                 360                 365
Leu Ser Leu Arg Leu Pro Ala Phe Leu Ala Lys Lys Pro Gly Leu Asn
    370                 375                 380
Ser Gly Leu Met Ile Ala Glu Val Thr Ser Ala Ala Leu Met Ser Glu
385                 390                 395                 400
Asn Lys Gln Leu Ser His Pro Ala Ser Val Asp Ser Thr Pro Thr Ser
                405                 410                 415
```

-continued

```
Ala Asn Gln Glu Asp His Val Ser Met Ala Cys His Gly Ala Arg Arg
            420                 425                 430

Leu Leu Gln Met Thr Glu Asn Leu Phe Ser Ile Ile Gly Ile Glu Ala
            435                 440                 445

Leu Ala Ala Val Gln Gly Ile Glu Phe Arg Ala Pro Leu Thr Thr Ser
            450                 455                 460

Pro Glu Leu Gln Lys Ala Ala Ala Val Arg Gly Val Ser Ser Ser
465                 470                 475                 480

Ile Glu Glu Asp Arg Tyr Met Ala Asp Asp Leu Lys Ala Ala Gly Asp
                    485                 490                 495

Leu Val Ala Ser Gly Arg Leu Ala Ala Ala Val Ser Ala Gly Leu Pro
            500                 505                 510

Lys

<210> SEQ ID NO 55
<211> LENGTH: 513
<212> TYPE: PRT
<213> ORGANISM: Pseudomonas aeruginosa

<400> SEQUENCE: 55

Met Ser Asp Leu Pro Ser Val Val Phe Gly Asp Gly Pro Leu Arg Trp
  1               5                  10                  15

Gln Glu Leu Val Ala Val Ala Arg His Gly Ala Arg Leu Glu Leu Ser
                 20                  25                  30

Ala Ala Ala Trp Ala Arg Ile Asp Asn Ala Arg Ala Ile Val Cys Arg
             35                  40                  45

Ile Val Ala Asn Gly Glu Arg Ala Tyr Gly Ile Ser Thr Gly Leu Gly
         50                  55                  60

Ala Leu Cys Asp Val Leu Leu Glu Gly Glu Gln Leu Ala Glu Leu Ser
 65                  70                  75                  80

Arg Asn Thr Leu Leu Ser His Ala Cys Gly Val Gly Glu Pro Leu Arg
                 85                  90                  95

Asp Glu Gln Thr Arg Ala Ile Ile Cys Ala Ala Val Ala Asn Tyr Ser
            100                 105                 110

Gln Gly Lys Ser Gly Leu Asp Arg Ser Leu Val Glu Gly Leu Leu Ala
            115                 120                 125

Leu Leu Asn His Gly Ile Thr Pro Gln Val Pro Ala Gln Gly Ser Val
130                 135                 140

Gly Tyr Ser Gly Asp Leu Thr His Met Ala His Val Gly Ile Ala Leu
145                 150                 155                 160

Leu Gly Ile Gly Glu Val Ser Asp Tyr Arg Gly Ser Val Val Pro Ala
                165                 170                 175

Ala Ala Ala Leu Ala Ala Glu Gly Leu Ala Thr Val Arg Leu Gly Ala
            180                 185                 190

Lys Asp Gly Leu Cys Leu Val Asn Gly Thr Pro Cys Met Thr Gly Leu
        195                 200                 205

Ala Cys Leu Ala Leu Asp Asp Ala Gln Arg Leu Ala Gln Trp Ala Asp
    210                 215                 220

Val Ile Gly Ala Met Ser Phe Glu Ala Leu Arg Gly Gln Leu Ala Ala
225                 230                 235                 240

Phe Asp Ala Glu Ile His Val Ala Leu Lys Pro His Pro Gly Met Gln
                245                 250                 255

Arg Val Ala Ala Asn Leu Arg Ala Leu Leu Ala Gly Ser Gln Val Leu
            260                 265                 270
```

-continued

```
Glu Asn Ala Arg Glu Gly Gly Ile Arg Thr Gln Asp Ala Leu Ser Ile
    275                 280                 285
Arg Ser Ile Pro Gln Ile His Gly Ala Cys Arg Asp Gln Leu Ala His
    290                 295                 300
Ala Arg Gln Ile Glu Thr Arg Glu Leu Asn Ser Ala Thr Asp Asn Pro
305                 310                 315                 320
Leu Leu Leu Gly Thr Pro Glu Val Val Ser Gln Ala Asn Pro His Gly
                325                 330                 335
Glu Ser Val Ala Met Ala Ala Asp Leu Leu Ala Ile Ala Val Ala Glu
            340                 345                 350
Leu Gly Gly Val Ala Glu Arg Arg Leu Asp Arg Leu Val Asn Pro Leu
        355                 360                 365
Val Ser Arg Gly Leu Pro Ala Phe Leu Val Gly Lys Pro Gly Val Asn
    370                 375                 380
Ser Gly Met Met Ile Thr Gln Tyr Val Ala Ala Ser Leu Ala Gly Glu
385                 390                 395                 400
Asn Arg Gln Leu Ala Gln Pro Ala Val Val Asp Asn Phe Val Thr Ser
                405                 410                 415
Ala Leu Gln Glu Asp His Leu Ser Leu Gly Thr Ser Ala Ala Leu Lys
            420                 425                 430
Leu Gly Arg Ala Leu Glu Asn Leu Arg Arg Ile Leu Ala Ile Glu Tyr
        435                 440                 445
Leu Leu Ala Ala Gln Ala Phe Glu Phe Leu Ala Pro Gln Arg Phe Gly
    450                 455                 460
Gln Gly Thr Ala Ala Ala Trp Gly Ile Leu Arg Glu Arg Val Pro Ala
465                 470                 475                 480
Tyr Asp Thr Asp Arg Trp Leu Ala Pro Asp Ile Ala Ser Ala Ala Ala
                485                 490                 495
Ile Leu Gly Glu Arg Lys Ser Leu Ala Arg Leu Ala Ala Ser Ile Gly
            500                 505                 510
Asp

<210> SEQ ID NO 56
<211> LENGTH: 513
<212> TYPE: PRT
<213> ORGANISM: Homo sapiens

<400> SEQUENCE: 56

Lys Tyr Arg Glu Pro Glu Lys Tyr Ile Glu Leu Asp Gly Leu Thr Thr
  1               5                  10                  15
Glu Asp Leu Val Asn Leu Gly Lys Gly Arg Tyr Lys Ile Lys Leu Thr
             20                  25                  30
Pro Thr Ala Glu Lys Arg Val Gln Lys Ser Arg Glu Val Ile Asp Ser
         35                  40                  45
Ile Ile Lys Glu Lys Thr Val Val Tyr Gly Ile Thr Thr Gly Phe Gly
     50                  55                  60
Lys Phe Ala Thr Arg Thr Val Ile Pro Ile Asn Lys Leu Gln Leu Gln
 65                  70                  75                  80
Val Asn Leu Val Arg Ser His Ser Ser Gly Val Gly Lys Pro Leu Ser
                 85                  90                  95
Pro Glu Arg Cys Arg Met Leu Leu Ala Leu Arg Ile Asn Val Leu Ala
            100                 105                 110
Lys Gly Tyr Ser Gly Ile Ser Leu Glu Thr Leu Lys Gln Val Ile Glu
        115                 120                 125
```

```
Met Phe Asn Ala Ser Cys Leu Pro Tyr Val Pro Glu Lys Gly Thr Val
    130                 135                 140

Gly Ala Ser Gly Asp Leu Ala Pro Leu Ser His Leu Ala Leu Gly Leu
145                 150                 155                 160

Val Gly Glu Gly Lys Met Trp Ser Pro Lys Ser Gly Trp Ala Asp Ala
                165                 170                 175

Lys Tyr Val Leu Glu Ala His Gly Leu Lys Pro Val Ile Leu Lys Pro
            180                 185                 190

Lys Glu Gly Leu Ala Leu Ile Asn Gly Thr Gln Met Ile Thr Ser Leu
        195                 200                 205

Gly Cys Glu Ala Val Glu Arg Ala Ser Ala Ile Ala Arg Gln Ala Asp
    210                 215                 220

Ile Val Ala Ala Leu Thr Leu Glu Val Leu Lys Gly Thr Thr Lys Ala
225                 230                 235                 240

Phe Asp Thr Asp Ile His Ala Pro Leu Arg Pro His Arg Gly Gln Ile
                245                 250                 255

Glu Val Ala Phe Arg Phe Arg Ser Leu Leu Ser Asp Ser Glu Ile Ala
            260                 265                 270

Glu Ser His Arg Phe Cys Asp Gly Arg Val Gln Asp Ala Tyr Thr Leu
        275                 280                 285

Arg Cys Cys Pro Gln Val His Gly Val Val Asn Asp Thr Ile Ala Phe
    290                 295                 300

Val Lys Asn Ile Ile Thr Thr Glu Leu Asn Ser Ala Thr Asp Asn Pro
305                 310                 315                 320

Met Val Phe Ala Asn Gly Glu Thr Val Ser Gly Gly Asn Phe His Gly
                325                 330                 335

Glu Tyr Pro Ala Lys Ala Leu Asp Tyr Leu Ala Ile Gly Ile His Glu
            340                 345                 350

Leu Ala Ala Ile Ser Glu Arg Arg Ile Glu Arg Leu Cys Asn Pro Ser
        355                 360                 365

Leu Ser Arg Glu Leu Pro Ala Phe Leu Val Ala Glu Gly Gly Leu Asn
    370                 375                 380

Ser Gly Phe Met Ile Ala His Cys Thr Ala Ala Leu Val Ser Glu
385                 390                 395                 400

Asn Lys Ala Leu Cys His Pro Ser Ser Val Asp Ser Leu Ser Thr Ser
                405                 410                 415

Ala Ala Thr Glu Asp His Val Ser Met Gly Gly Trp Ala Ala Arg Lys
            420                 425                 430

Ala Leu Arg Val Ile Glu His Val Glu Gln Val Leu Ala Ile Glu Leu
        435                 440                 445

Leu Ala Ala Cys Gln Gly Ile Glu Phe Leu Arg Pro Leu Lys Thr Thr
    450                 455                 460

Thr Pro Leu Glu Lys Val Tyr Asp Leu Val Arg Ser Val Val Arg Pro
465                 470                 475                 480

Trp Ile Lys Asp Arg Phe Met Ala Pro Asp Ile Glu Ala Ala His Arg
                485                 490                 495

Leu Leu Leu Glu Gln Lys Val Trp Glu Val Ala Ala Pro Tyr Ile Glu
            500                 505                 510

Lys

<210> SEQ ID NO 57
<211> LENGTH: 513
<212> TYPE: PRT
```

<213> ORGANISM: Caenorhabditis elegans

<400> SEQUENCE: 57

| | | | | | | | | | | | | | | | |
|---|---|---|---|---|---|---|---|---|---|---|---|---|---|---|---|
|Val|Leu|Ala|Pro|Pro|Thr|Lys|Leu|Leu|Ile|Leu|Asp|Gly|Asn|Ser|Pro|
|1| | | |5| | | | |10| | | | |15| |
|Glu|Asp|Leu|Val|Arg|Cys|Glu|Lys|Gly|Glu|Cys|Ala|Ile|Gln|Leu|Ser|
| | | | |20| | | | |25| | | | |30| |
|Met|Glu|Ser|Glu|Asp|Arg|Ile|Arg|Lys|Ala|Arg|Thr|Phe|Leu|Glu|Lys|
| | | |35| | | | |40| | | | |45| | |
|Ile|Ala|Ser|Glu|His|Arg|Ala|Val|Tyr|Gly|Val|Thr|Thr|Gly|Phe|Gly|
| | |50| | | | |55| | | | |60| | | |
|Thr|Phe|Ser|Asn|Val|Thr|Ile|Pro|Pro|Glu|Lys|Leu|Lys|Lys|Leu|Gln|
|65| | | | |70| | | | |75| | | | |80|
|Leu|Asn|Leu|Ile|Arg|Ser|His|Ala|Thr|Gly|Tyr|Gly|Glu|Pro|Leu|Ala|
| | | | |85| | | | |90| | | | |95| |
|Pro|Asn|Arg|Ala|Arg|Met|Leu|Leu|Ala|Leu|Arg|Ile|Asn|Ile|Leu|Ala|
| | | |100| | | | |105| | | | |110| | |
|Lys|Gly|His|Ser|Gly|Ile|Ser|Val|Glu|Asn|Ile|Lys|Lys|Met|Ile|Ala|
| | |115| | | | |120| | | | |125| | | |
|Ala|Phe|Asn|Ala|Phe|Cys|Val|Ser|Tyr|Val|Pro|Gln|Gln|Gly|Thr|Val|
| |130| | | | |135| | | | |140| | | | |
|Gly|Cys|Ser|Gly|Asp|Leu|Cys|Pro|Leu|Ala|His|Leu|Ala|Leu|Gly|Leu|
|145| | | | |150| | | | |155| | | | |160|
|Leu|Gly|Glu|Gly|Lys|Met|Trp|Ser|Pro|Thr|Thr|Gly|Trp|Gln|Pro|Ala|
| | | | |165| | | | |170| | | | |175| |
|Asp|Val|Val|Leu|Lys|Lys|Asn|Asn|Leu|Glu|Pro|Leu|Glu|Leu|Gly|Pro|
| | | |180| | | | |185| | | | |190| | |
|Lys|Glu|Gly|Leu|Ala|Leu|Ile|Asn|Gly|Thr|Gln|Met|Val|Thr|Ala|Leu|
| | |195| | | | |200| | | | |205| | | |
|Gly|Ala|Tyr|Thr|Leu|Glu|Arg|Ala|His|Asn|Ile|Ala|Arg|Gln|Ala|Asp|
| |210| | | | |215| | | | |220| | | | |
|Val|Ile|Ala|Ala|Leu|Ser|Leu|Asp|Val|Leu|Lys|Gly|Thr|Thr|Arg|Ala|
|225| | | | |230| | | | |235| | | | |240|
|Tyr|Asp|Pro|Asp|Ile|His|Arg|Pro|Ile|Arg|Pro|His|Arg|Gly|Gln|Asn|
| | | | |245| | | | |250| | | | |255| |
|Leu|Ser|Ala|Leu|Arg|Leu|Arg|Ala|Leu|Leu|Asn|Pro|Ser|Gln|Ile|Ala|
| | | |260| | | | |265| | | | |270| | |
|Glu|Ser|His|Arg|Asn|Cys|Thr|Gly|Lys|Val|Gln|Asp|Ala|Tyr|Thr|Leu|
| | |275| | | | |280| | | | |285| | | |
|Arg|Cys|Val|Pro|Gln|Val|His|Gly|Val|Val|His|Asp|Thr|Ile|Glu|Phe|
| |290| | | | |295| | | | |300| | | | |
|Val|Arg|Glu|Ile|Ile|Thr|Thr|Glu|Met|Asn|Ser|Ala|Thr|Asp|Asn|Pro|
|305| | | | |310| | | | |315| | | | |320|
|Leu|Val|Phe|Ala|Asp|Arg|Glu|Ile|Ile|Ser|Gly|Gly|Asn|Phe|His|Gly|
| | | | |325| | | | |330| | | | |335| |
|Glu|Tyr|Pro|Ala|Lys|Ala|Leu|Asp|Phe|Leu|Ala|Ile|Ala|Val|Ala|Glu|
| | | |340| | | | |345| | | | |350| | |
|Leu|Ala|Gln|Met|Ser|Glu|Arg|Arg|Leu|Glu|Arg|Leu|Val|Asn|Lys|Glu|
| | |355| | | | |360| | | | |365| | | |
|Leu|Ser|Arg|Gly|Leu|Pro|Thr|Phe|Leu|Thr|Pro|Asp|Gly|Gly|Leu|Asn|
| |370| | | | |375| | | | |380| | | | |
|Ser|Gly|Phe|Met|Thr|Val|Gln|Leu|Cys|Ala|Ala|Ser|Leu|Val|Ser|Glu|
|385| | | | |390| | | | |395| | | | |400|

-continued

```
Asn Lys Val Leu Cys His Pro Ser Ser Val Asp Ser Ile Pro Thr Ser
            405                 410                 415

Cys Asn Gln Glu Asp His Val Ser Met Gly Gly Phe Ala Ala Arg Lys
        420                 425                 430

Ala Leu Thr Val Val Glu His Val Glu Ala Val Leu Ala Met Glu Leu
    435                 440                 445

Leu Ala Ala Cys Gln Gly Ile Glu Phe Leu Lys Pro Leu Ile Ser Thr
450                 455                 460

Ala Pro Leu His Lys Ile Tyr Gln Leu Val Arg Ser Lys Val Ala Pro
465                 470                 475                 480

Pro Asn Glu Asp Arg Tyr Met Lys Pro Glu Ile Asp Ala Val Leu Glu
                485                 490                 495

Met Ile Arg Glu Asn Arg Ile Trp Glu Ala Val Leu Pro His Leu Glu
            500                 505                 510

Thr

<210> SEQ ID NO 58
<211> LENGTH: 513
<212> TYPE: PRT
<213> ORGANISM: Thermoplasma acidophilum

<400> SEQUENCE: 58

Met Ala Ser Ala Pro Met Ile Glu Ile Asp Gly Arg Ser Leu Arg Val
1               5                   10                  15

Glu Asp Val Tyr Ala Val Ala Val Glu Tyr Asp Arg Val Ser Ile Ser
            20                  25                  30

Asp Asp Thr Leu Lys Ala Val Glu Glu Lys His Glu Ala Phe Leu Lys
        35                  40                  45

Leu Ile Asn Ser Gly Lys Thr Val Tyr Gly Val Asn Thr Gly Phe Gly
    50                  55                  60

Ser Leu Leu Asn Val His Ile Glu Arg Asp Gln Glu Ile Glu Leu Gln
65                  70                  75                  80

Lys Asn Leu Ile Arg Ser His Ser Ser Gly Val Gly Asp Tyr Leu Glu
                85                  90                  95

Asn Arg Tyr Val Arg Ala Ile Met Ala Val Arg Leu Asn Ser Leu Ala
            100                 105                 110

Ala Gly Tyr Ser Ala Val Ser Ala Asp Leu Leu Asn Met Met Val Glu
        115                 120                 125

Met Leu Asn Arg Asp Val Ile Pro Ala Val Pro Lys Tyr Gly Ser Val
    130                 135                 140

Gly Ala Ser Gly Asp Leu Ala Pro Leu Ala His Ile Gly Leu Ala Met
145                 150                 155                 160

Met Gly Glu Gly Lys Ala Phe Asp Phe Glu Gly Arg Leu Met Asp Ser
                165                 170                 175

Ala Arg Ala Leu Glu Lys Ala Gly Leu Lys Pro Tyr Gln Phe Lys Glu
            180                 185                 190

Lys Glu Gly Val Ala Leu Ile Asn Gly Thr Ser Phe Met Ser Gly Ile
        195                 200                 205

Leu Ser Ile Ala Val Met Asp Ala His Asp Ile Leu Glu Asn Ala Ile
    210                 215                 220

Arg Ser Ala Leu Leu Ser Phe Glu Ala Leu Gly Gly Thr Ser Lys Ala
225                 230                 235                 240

Phe Thr Pro Trp Ile Leu Gly Ala Leu Arg Pro His Leu Gly Gln Val
                245                 250                 255
```

-continued

```
Ala Ile Gly Asn Arg Phe Arg Glu Tyr Leu Thr Gly Ser Asp Ile Val
            260                 265                 270

Ala Ser Lys Arg Ala Asp Ser Val Lys Val Gln Asp Ala Tyr Thr Leu
        275                 280                 285

Arg Cys Ile Pro Gln Val Tyr Gly Ser Val Ala Asp Val Ile Asp Tyr
290                 295                 300

Val Glu Asn Val Leu Ser Val Glu Ile Asn Ser Ala Thr Asp Asn Pro
305                 310                 315                 320

Leu Val Phe Asn Gly Glu Val Val Ser Gly Asn Phe His Gly
            325                 330                 335

Glu Pro Val Ala Leu Ala Asp Phe Leu Ala Ile Ala Leu Thr Asp
            340                 345                 350

Leu Gly Asn Met Val Glu Arg Arg Ile Ala Arg Leu Val Asp Thr Asn
            355                 360                 365

Leu Ser Arg Gly Leu Pro Pro Phe Leu Thr Pro Asp Ser Gly Leu Asn
    370                 375                 380

Ser Gly Tyr Met Ile Pro Gln Tyr Thr Ala Ala Ala Leu Cys Asn Arg
385                 390                 395                 400

Asn Lys Val Leu Ala Tyr Pro Ser Ser Ala Asp Thr Ile Pro Thr Ser
                405                 410                 415

Ala Asn Gln Glu Asp His Val Ser Met Gly Ala Thr Gly Ser Leu Lys
            420                 425                 430

Leu Leu Glu Ile Ile Asp Asn Val Arg Tyr Ile Ile Ala Ile Glu Tyr
        435                 440                 445

Leu Leu Gly Ser Gln Ala Leu Glu Phe Thr Asp Lys Leu Gly Met Ser
    450                 455                 460

Pro Ser Thr Arg Lys Ile Tyr Glu Lys Ile Arg Glu Lys Val Glu Lys
465                 470                 475                 480

Leu Asp His Asp Arg Pro Pro Ser Phe Asp Ile Glu Thr Ile Arg Lys
                485                 490                 495

Met Met Asp Lys Lys Glu Phe Ile Ser Ala Leu Pro Ala His Leu Pro
            500                 505                 510

Ala
```

<210> SEQ ID NO 59
<211> LENGTH: 513
<212> TYPE: PRT
<213> ORGANISM: Mus sp.

<400> SEQUENCE: 59

```
Lys Tyr Arg Glu Pro Glu Lys Tyr Ile Ala Leu Asp Gly Asp Ser Thr
1               5                   10                  15

Glu Asp Leu Val Asn Leu Gly Lys Gly Arg Tyr Lys Ile Lys Leu Thr
                20                  25                  30

Ser Ile Ala Glu Lys Lys Val Gln Gln Ser Arg Glu Val Ile Asp Ser
            35                  40                  45

Ile Ile Lys Glu Arg Thr Val Val Tyr Gly Ile Thr Thr Gly Phe Gly
        50                  55                  60

Lys Phe Ala Thr Arg Thr Val Ile Pro Ala Asn Lys Leu Gln Leu Gln
65                  70                  75                  80

Val Asn Leu Val Arg Ser His Ser Ser Gly Val Gly Lys Pro Leu Ser
                85                  90                  95

Pro Glu Arg Cys Arg Met Leu Leu Ala Leu Arg Ile Asn Val Leu Ala
            100                 105                 110
```

-continued

```
Lys Gly Tyr Ser Gly Ile Ser Leu Glu Thr Leu Lys Gln Val Ile Glu
            115                 120                 125
Ala Phe Asn Ala Ser Cys Leu Ser Tyr Val Pro Glu Lys Gly Thr Val
130                 135                 140
Gly Ala Ser Gly Asp Leu Ala Pro Leu Ser His Leu Ala Leu Gly Leu
145                 150                 155                 160
Ile Gly Glu Gly Lys Met Trp Ser Pro Lys Ser Gly Trp Ala Asp Ala
                    165                 170                 175
Lys Tyr Val Leu Glu Ala His Gly Leu Lys Pro Ile Val Leu Lys Pro
                180                 185                 190
Lys Glu Gly Leu Ala Leu Ile Asn Gly Thr Gln Met Ile Thr Ser Leu
            195                 200                 205
Gly Cys Glu Ala Leu Glu Arg Ala Ser Ala Ile Ala Arg Gln Ala Asp
210                 215                 220
Ile Val Ala Ala Leu Thr Leu Glu Val Leu Lys Gly Thr Thr Lys Ala
225                 230                 235                 240
Phe Asp Thr Asp Ile His Ala Pro Val Arg Pro His Arg Gly Gln Ile
                    245                 250                 255
Glu Val Ala Phe Arg Phe Arg Ser Leu Leu Ser Asp Ser Glu Ile Ala
                260                 265                 270
Glu Ser His Arg Phe Cys Asp Gly Arg Val Gln Asp Ala Tyr Thr Leu
            275                 280                 285
Arg Cys Cys Pro Gln Val His Gly Val Val Asn Asp Thr Ile Ala Phe
290                 295                 300
Val Lys Asp Ile Ile Thr Thr Glu Leu Asn Ser Ala Thr Asp Asn Pro
305                 310                 315                 320
Met Val Phe Ala Ser Gly Glu Thr Ile Ser Gly Gly Asn Phe His Gly
                    325                 330                 335
Glu Tyr Pro Ala Lys Ala Leu Asp Tyr Leu Ala Ile Gly Val His Glu
                340                 345                 350
Leu Ala Ala Ile Ser Glu Arg Arg Ile Glu Arg Leu Cys Asn Pro Ser
            355                 360                 365
Leu Ser Arg Glu Leu Pro Ala Phe Leu Val Ala Glu Gly Gly Leu Asn
370                 375                 380
Ser Gly Phe Met Ile Ala His Cys Thr Ala Ala Leu Val Ser Glu
385                 390                 395                 400
Ser Lys Ala Leu Cys His Pro Ser Ser Val Asp Ser Leu Ser Thr Ser
                    405                 410                 415
Ala Ala Thr Glu Asp His Val Ser Met Gly Gly Trp Ala Ala Arg Lys
                420                 425                 430
Ala Leu Arg Val Val Glu His Val Glu Gln Val Leu Ala Ile Glu Leu
            435                 440                 445
Leu Ala Ala Cys Gln Gly Ile Glu Phe Leu Arg Pro Leu Lys Thr Thr
450                 455                 460
Thr Pro Leu Glu Lys Val Tyr Asp Leu Val Arg Ser Val Val Arg Pro
465                 470                 475                 480
Trp Ile Lys Asp Arg Phe Met Ala Pro Asp Ile Glu Ala Ala His Arg
                    485                 490                 495
Leu Leu Leu Asp Gln Lys Val Trp Glu Val Ala Ala Pro Tyr Ile Glu
                500                 505                 510
Lys
```

<210> SEQ ID NO 60

```
<211> LENGTH: 513
<212> TYPE: PRT
<213> ORGANISM: Mus musculus

<400> SEQUENCE: 60

Lys Tyr Arg Glu Pro Glu Lys Tyr Ile Ala Leu Asp Gly Asp Ser Thr
  1               5                  10                  15

Glu Asp Leu Val Asn Leu Gly Lys Gly Arg Tyr Lys Ile Lys Leu Thr
             20                  25                  30

Ser Ile Ala Glu Lys Lys Val Gln Gln Ser Arg Glu Val Ile Asp Ser
         35                  40                  45

Ile Ile Lys Glu Arg Thr Val Val Tyr Gly Ile Thr Thr Gly Phe Gly
 50                  55                  60

Lys Phe Ala Thr Arg Thr Val Ile Pro Ala Asn Lys Leu Gln Leu Gln
 65                  70                  75                  80

Val Asn Leu Val Arg Ser His Ser Ser Gly Val Gly Lys Pro Leu Ser
             85                  90                  95

Pro Glu Arg Cys Arg Met Leu Leu Ala Leu Arg Ile Asn Val Leu Ala
            100                 105                 110

Lys Gly Tyr Ser Gly Ile Ser Leu Glu Thr Leu Lys Gln Val Ile Glu
        115                 120                 125

Ala Phe Asn Ala Ser Cys Leu Ser Tyr Val Pro Glu Lys Gly Thr Val
    130                 135                 140

Gly Ala Ser Gly Asp Leu Ala Pro Leu Ser His Leu Ala Leu Gly Leu
145                 150                 155                 160

Ile Gly Glu Gly Lys Met Trp Ser Pro Lys Ser Gly Trp Ala Asp Ala
                165                 170                 175

Lys Tyr Val Leu Glu Ala His Gly Leu Lys Pro Ile Val Leu Lys Pro
            180                 185                 190

Lys Glu Gly Leu Ala Leu Ile Asn Gly Thr Gln Met Ile Thr Ser Leu
        195                 200                 205

Gly Cys Glu Ala Leu Glu Arg Ala Ser Ala Ile Ala Arg Gln Ala Asp
    210                 215                 220

Ile Val Ala Ala Leu Thr Leu Glu Val Leu Lys Gly Thr Thr Lys Ala
225                 230                 235                 240

Phe Asp Thr Asp Ile His Ala Pro Val Arg Pro His Arg Gly Gln Ile
                245                 250                 255

Glu Val Ala Phe Arg Phe Arg Ser Leu Leu Ser Asp Ser Glu Ile Ala
            260                 265                 270

Glu Ser His Arg Phe Cys Asp Gly Arg Val Gln Asp Ala Tyr Thr Leu
        275                 280                 285

Arg Cys Cys Pro Gln Val His Gly Val Val Asn Asp Thr Ile Ala Phe
    290                 295                 300

Val Lys Asp Ile Ile Thr Thr Glu Leu Asn Ser Ala Thr Asp Asn Pro
305                 310                 315                 320

Met Val Phe Ala Ser Gly Glu Thr Ile Ser Gly Gly Asn Phe His Gly
                325                 330                 335

Glu Tyr Pro Ala Lys Ala Leu Asp Tyr Leu Ala Ile Gly Val His Glu
            340                 345                 350

Leu Ala Ala Ile Ser Glu Arg Arg Ile Glu Arg Leu Cys Asn Pro Ser
        355                 360                 365

Leu Ser Arg Glu Leu Pro Ala Phe Leu Val Ala Glu Gly Gly Leu Asn
    370                 375                 380

Ser Gly Phe Met Ile Ala His Cys Thr Ala Ala Ala Leu Val Ser Glu
```

-continued

```
            385                 390                 395                 400
Ser Lys Ala Leu Cys His Pro Ser Ser Val Asp Ser Leu Ser Thr Ser
                    405                 410                 415

Ala Ala Thr Glu Asp His Val Ser Met Gly Gly Trp Ala Ala Arg Lys
            420                 425                 430

Ala Leu Arg Val Val Glu His Val Glu Gln Val Leu Ala Ile Glu Leu
            435                 440                 445

Leu Ala Ala Cys Gln Gly Ile Glu Phe Leu Arg Pro Leu Lys Thr Thr
        450                 455                 460

Thr Pro Leu Glu Lys Val Tyr Asp Leu Val Arg Ser Val Val Arg Pro
465                 470                 475                 480

Trp Ile Lys Asp Arg Phe Met Ala Pro Asp Ile Glu Ala Ala His Arg
                485                 490                 495

Leu Leu Leu Asp Gln Lys Val Trp Glu Val Ala Ala Pro Tyr Ile Glu
            500                 505                 510

Lys

<210> SEQ ID NO 61
<211> LENGTH: 513
<212> TYPE: PRT
<213> ORGANISM: Rattus sp.

<400> SEQUENCE: 61

Lys Tyr Arg Glu Pro Glu Lys Tyr Ile Ala Leu Asp Gly Asp Ser Thr
  1               5                  10                  15

Glu Asp Leu Val Asn Leu Gly Lys Gly His Tyr Lys Ile Lys Leu Thr
                 20                  25                  30

Ser Ile Ala Glu Lys Lys Val Gln Gln Ser Arg Glu Val Ile Asp Ser
             35                  40                  45

Ile Ile Lys Glu Arg Thr Val Val Tyr Gly Ile Thr Thr Gly Phe Gly
         50                  55                  60

Lys Phe Ala Thr Arg Thr Val Ile Pro Ala Asn Lys Leu Gln Leu Gln
 65                  70                  75                  80

Val Asn Leu Val Arg Ser His Ser Ser Gly Val Gly Lys Pro Leu Ser
                 85                  90                  95

Pro Glu Arg Cys Arg Met Leu Leu Ala Leu Arg Ile Asn Val Leu Ala
            100                 105                 110

Lys Gly Tyr Ser Gly Ile Ser Leu Glu Thr Leu Lys Gln Val Ile Glu
        115                 120                 125

Val Phe Asn Ala Ser Cys Leu Ser Tyr Val Pro Glu Lys Gly Thr Val
    130                 135                 140

Gly Ala Ser Gly Asp Leu Ala Pro Leu Ser His Leu Ala Leu Gly Leu
145                 150                 155                 160

Ile Gly Glu Gly Lys Met Trp Ser Pro Lys Ser Gly Trp Ala Asp Ala
                165                 170                 175

Lys Tyr Val Leu Glu Ala His Gly Leu Lys Pro Ile Val Leu Lys Pro
            180                 185                 190

Lys Glu Gly Leu Ala Leu Ile Asn Gly Thr Gln Met Ile Thr Ser Leu
        195                 200                 205

Gly Cys Glu Ala Val Glu Arg Ala Ser Ala Ile Ala Arg Gln Ala Asp
    210                 215                 220

Ile Val Ala Ala Leu Thr Leu Glu Val Leu Lys Gly Thr Thr Lys Ala
225                 230                 235                 240

Phe Asp Thr Asp Ile His Ala Pro Val Arg Pro His Arg Gly Gln Ile
```

```
                    245                 250                 255
Glu Val Ala Phe Arg Phe Arg Ser Leu Leu Ser Asp Ser Glu Ile Ala
                260                 265                 270

Glu Ser His Arg Phe Cys Asp Gly Arg Val Gln Asp Ala Tyr Thr Leu
            275                 280                 285

Arg Cys Cys Pro Gln Val His Gly Val Val Asn Asp Thr Ile Ala Phe
        290                 295                 300

Val Lys Asp Ile Ile Thr Thr Glu Leu Asn Ser Ala Thr Asp Asn Pro
305                 310                 315                 320

Met Val Phe Ala Ser Gly Glu Thr Ile Ser Gly Gly Asn Phe His Gly
                325                 330                 335

Glu Tyr Pro Ala Lys Ala Leu Asp Tyr Leu Ala Ile Gly Val His Glu
            340                 345                 350

Leu Ala Ala Ile Ser Glu Arg Arg Ile Glu Arg Leu Cys Asn Pro Ser
        355                 360                 365

Leu Ser Arg Glu Leu Pro Ala Phe Leu Val Ala Glu Gly Gly Leu Asn
    370                 375                 380

Ser Gly Phe Met Ile Ala His Cys Thr Ala Ala Leu Val Ser Glu
385                 390                 395                 400

Ser Lys Ala Leu Cys His Pro Ser Ser Val Asp Ser Leu Ser Thr Ser
                405                 410                 415

Ala Ala Thr Glu Asp His Val Ser Met Gly Gly Trp Ala Ala Arg Lys
            420                 425                 430

Ala Leu Arg Val Ile Glu His Val Gln Val Leu Ala Ile Glu Leu
        435                 440                 445

Leu Ala Ala Cys Gln Gly Ile Glu Phe Leu Arg Pro Leu Lys Thr Thr
    450                 455                 460

Thr Pro Leu Glu Lys Val Tyr Asp Leu Val Arg Ser Val Val Arg Pro
465                 470                 475                 480

Trp Ile Lys Asp Arg Phe Met Ala Pro Asp Ile Glu Ala Ala His Arg
                485                 490                 495

Leu Leu Leu Asp Gln Lys Val Trp Glu Val Ala Ala Pro Tyr Ile Glu
            500                 505                 510

Lys

<210> SEQ ID NO 62
<211> LENGTH: 513
<212> TYPE: PRT
<213> ORGANISM: Unknown Organism
<220> FEATURE:
<223> OTHER INFORMATION: Description of Unknown Organism: Uncultured
      bacterium pCosAS1

<400> SEQUENCE: 62

Met Ala Ser Met Asn Ala Leu Thr Leu Thr Pro Gly Thr Leu Thr Leu
1               5                   10                  15

Ala Gln Leu Arg Gln Val Trp Gln Gln Pro Leu Gln Leu Thr Leu Asp
            20                  25                  30

Glu Ser Ala His Glu Ala Ile Asn Asp Ser Val Ala Cys Val Glu Ala
        35                  40                  45

Ile Val Ala Glu Gly Arg Thr Ala Tyr Gly Ile Asn Thr Gly Phe Gly
    50                  55                  60

Leu Leu Ala Gln Thr Arg Ile Ala Thr His Asp Leu Glu Asn Leu Gln
65                  70                  75                  80

Arg Ser Leu Val Leu Ser His Ala Ala Gly Val Gly Glu Pro Leu Asp
```

-continued

```
                    85                  90                  95
Asp Asp Ile Val Arg Leu Met Met Val Leu Lys Ile Asn Ser Leu Ala
                100                 105                 110
Arg Gly Phe Ser Gly Ile Arg Leu Ser Val Ile Gln Ala Leu Ile Ala
            115                 120                 125
Leu Val Asn Ala Gly Val Tyr Ser Val Asp Pro Ala Lys Gly Ser Val
        130                 135                 140
Gly Ala Ser Gly Asp Leu Ala Pro Leu Ala His Met Ser Leu Thr Leu
145                 150                 155                 160
Leu Gly Glu Gly Lys Ala Arg Asp Tyr Arg Gly Glu Trp Leu Pro Ala
                165                 170                 175
Ala Thr Ala Leu Gln Lys Ala Gly Leu Ala Pro Val Thr Leu Ala Ala
                180                 185                 190
Lys Glu Gly Leu Ala Leu Leu Asn Gly Thr Gln Ala Ser Thr Ala Phe
            195                 200                 205
Ala Leu Arg Gly Leu Phe Glu Ala Glu Asp Leu Phe Ala Ser Ala Val
        210                 215                 220
Val Cys Gly Ala Leu Thr Thr Glu Ala Val Leu Gly Ser Arg Arg Pro
225                 230                 235                 240
Phe Asp Ala Arg Ile His Glu Pro Val Arg Gly Gln Arg Gly Gln Ile
                245                 250                 255
Asp Ala Ala Leu Phe Arg His Val Leu Thr Asp Thr Ser Ala Ile
            260                 265                 270
Ala Ser His His Asn Cys Asp Gly Lys Val Gln Asp Pro Tyr Ser Leu
        275                 280                 285
Arg Cys Gln Pro Gln Val Met Gly Ala Cys Leu Thr Gln Met Arg Gln
    290                 295                 300
Val Ala Glu Val Leu Leu Val Glu Ser Asn Ala Val Ser Asp Asn Pro
305                 310                 315                 320
Leu Val Phe Ala Ala Asn Glu Met Val Phe Arg Gly Asn Phe His Ala
                325                 330                 335
Glu Pro Val Ala Met Ala Ala Asp Asn Leu Ala Leu Ala Ile Ala Glu
                340                 345                 350
Ile Gly Ala Leu Ser Glu Arg Arg Ile Ala Leu Met Met Asp Lys His
            355                 360                 365
Met Ser Gln Asp Leu Pro Pro Phe Leu Val Arg Asn Gly Gly Val Asn
        370                 375                 380
Ser Gly Phe Met Ile Ala Gln Val Thr Ala Ala Ala Leu Ala Ser Glu
385                 390                 395                 400
Asn Lys Gly Leu Cys His Pro Thr Ser Val Asp Lys Ile Pro Pro Ser
                405                 410                 415
Ala Asn Gln Glu Asp His Val Ser Met Ala Pro Ala Ala Gly Arg Arg
                420                 425                 430
Leu Trp Glu Met Ala Gly Asn Thr Arg Gly Val Leu Ala Val Glu Trp
            435                 440                 445
Leu Ala Ala Cys Gln Gly Ala Asp Leu Arg Asp Gly Leu Thr Ser Ser
        450                 455                 460
Pro Leu Leu Glu Gln Ala Arg Gln Ser Cys Gly Glu Gln Val Ala His
465                 470                 475                 480
Tyr Asp Asp Asp Arg Phe Phe Ala Pro Asp Ile Glu Ala Ala Ile Ser
                485                 490                 495
Leu Leu Asn Lys Gly Ser Leu Val Gly Leu Leu Pro Ala Phe Leu Pro
            500                 505                 510
```

Ala

<210> SEQ ID NO 63
<211> LENGTH: 513
<212> TYPE: PRT
<213> ORGANISM: Rhizobium meliloti

<400> SEQUENCE: 63

```
Met Ala Ser Ala Met Gly Glu Met Ile Ser Leu Asp Gly Pro Leu Thr
  1               5                  10                  15

Trp Arg Glu Ile Ala Ser Ile Ala Glu Gly Ala Ser Leu Asp Leu Ser
             20                  25                  30

Gly Pro Ala Arg Leu Arg Ile Ala Gln Ala Arg Arg Ile Val Asp Ala
         35                  40                  45

Leu Val Glu Arg Gly Ile Arg Gly Tyr Gly Ile Asn Thr Gly Val Gly
     50                  55                  60

Ala Leu Cys Asp Val Ile Ile Ser Arg Glu Asn Gln Gln Ala Leu Ser
 65                  70                  75                  80

Arg Asn Ile Ile Leu Ser His Ala Cys Gly Val Gly Asp Pro Leu Gly
                 85                  90                  95

Arg Val Glu Ala Arg Ala Val Met Ala Ala Gln Ile Ala Asn Leu Thr
            100                 105                 110

His Gly Tyr Ser Gly Val Arg Val Glu Thr Ala Glu Met Leu Leu Ala
        115                 120                 125

Leu Leu Asn Ala Asp Ile Ile Pro Leu Ile Pro Ser Arg Gly Ser Val
    130                 135                 140

Gly Tyr Ser Gly Asp Leu Ala Pro Leu Thr His Ala Ala Leu Val Leu
145                 150                 155                 160

Ile Gly His Gly Ser Ala Met Gln Gly Thr Glu Arg Leu Ser Gly Ala
                165                 170                 175

Asp Ala Leu Phe Ala Arg Leu Gly Leu Ala Pro Leu Arg Leu Glu Ala
            180                 185                 190

Lys Glu Gly Leu Ser Leu Val Asn Gly Thr Pro Cys Ala Thr Gly Leu
        195                 200                 205

Ala Ala Leu Ala Leu Ala Arg Thr Glu Arg Leu Phe Ala Trp Ala Asp
    210                 215                 220

Ala Ala Ala Met Thr Tyr Glu Ala Asn Leu Gly Ser Gln Ala Asn
225                 230                 235                 240

Ala Phe Ala Glu Leu Pro Leu Ala Leu Arg Gln Ser Pro Gly Leu Ser
                245                 250                 255

Ala Val Gly Glu Gly Leu Arg Asp Trp Leu Ala Asp Ser Pro Met Leu
            260                 265                 270

Ala Gly His Arg Thr Ala Gly Thr Arg Thr Gln Asp Pro Leu Ser Leu
        275                 280                 285

Arg Ala Val Pro Gln Val His Gly Ala Ala Arg Asp Ala Phe Gly Gln
    290                 295                 300

Val Ala Glu Ile Val Asp Arg Glu Leu Ala Ser Val Thr Asp Asn Pro
305                 310                 315                 320

Ala Val Ala Gly Ser Pro Glu Val His Ser Gln Ala His Ala Val Gly
                325                 330                 335

Ala Ala Leu Gly Leu Ala Met Asp Ser Leu Ala Val Ala Val Ala Glu
            340                 345                 350

Val Ala Ala Ile Ser Glu Arg Arg Ile Asp Arg Leu Val Asn Pro Leu
        355                 360                 365
```

```
Val Ser Arg Gly Leu Pro Ala Phe Leu Ala Gly Asp Ser Gly Val Ser
    370                 375                 380

Ser Gly Phe Met Ile Ala Gln Tyr Thr Ala Ala Leu Val Ala Glu
385                 390                 395                 400

Asn Arg Arg Leu Ala Ala Pro Ala Ser Leu Asp Gly Gly Ile Thr Ser
                405                 410                 415

Ala Leu Gln Glu Asp Met Leu Thr His Ala Thr Pro Ala Ala Trp Lys
                420                 425                 430

Ala Leu Ser Ile Val Asp Asn Leu Glu Arg Ile Leu Ala Ile Glu Leu
                435                 440                 445

Leu Ala Ala His Arg Pro Met Ser Cys Ser Arg Lys Arg Arg Ala Arg
    450                 455                 460

Arg Asn Ala Pro Leu Pro Phe Thr Gly Thr Tyr Ala Arg Arg Ser Pro
465                 470                 475                 480

Pro Ile Ala Thr Ile Val Arg Ser Ala Glu Leu Glu Ala Ala Tyr Asp
                485                 490                 495

Leu Leu Ala Asn Gly Ser Val His Lys Ala Leu Glu Ala His Leu Pro
                500                 505                 510

Ala

<210> SEQ ID NO 64
<211> LENGTH: 513
<212> TYPE: PRT
<213> ORGANISM: Halobacterium sp.

<400> SEQUENCE: 64

Met Ala Ser Ala Pro Gln Ile Thr Leu Gly Leu Ser Gly Ala Thr Ala
1               5                   10                  15

Asp Asp Val Ile Ala Val Ala Arg His Glu Ala Arg Ile Ser Ile Ser
                20                  25                  30

Pro Gln Val Leu Glu Glu Leu Ala Ser Val Arg Ala His Ile Asp Ala
            35                  40                  45

Leu Ala Ser Ala Asp Thr Pro Val Tyr Gly Ile Ser Thr Gly Phe Gly
    50                  55                  60

Ala Met Ser Asp Thr Arg Ile Asp Ala Ala Asp Arg Glu Ala Leu Gln
65                  70                  75                  80

Ala Asn Leu Val Arg Ser His Ala Ala Gly Ala Gly Ser Glu Leu Asp
                85                  90                  95

Thr Ala Ala Val Arg Ala Leu Leu Val Thr Arg Leu Asn Ala Leu Ala
                100                 105                 110

Lys Gly Tyr Ser Gly Ile Arg Glu Arg Val Leu Asp Val Leu Val Gly
            115                 120                 125

Leu Leu Asn Glu Gly Val His Pro Val Val Pro Ser Arg Gly Ser Leu
    130                 135                 140

Gly Ala Ser Gly Asp Leu Ala Pro Leu Ala His Met Ser Arg Val Leu
145                 150                 155                 160

Ile Gly Glu Gly Gln Ala Thr Asp Val Ala Gly Glu Arg Met Pro Ala
                165                 170                 175

Ala Glu Ala Leu Ala Ala Asp Leu Glu Pro Val Thr Leu Gln Ala
                180                 185                 190

Lys Glu Gly Leu Ala Leu Ile Asn Gly Thr Gln Leu Thr Thr Gly Val
            195                 200                 205

Ala Ala Leu Ala Leu Val Asp Ala Glu Arg Val Leu Arg Ser Ala Asp
    210                 215                 220
```

```
Thr Ala Gly Ala Leu Thr Thr Glu Val Thr Met Ser Thr Thr Ala Ser
225                 230                 235                 240

Cys Ala Pro Ala Ile His Glu Pro Val Arg Pro His Asp Gly Gln Ala
            245                 250                 255

Val Ser Ala Arg His Ile Arg Asn Leu Thr Ala Gly Ser Glu Val Leu
            260                 265                 270

Asp His His Arg Asp Cys Asp Gly Arg Val Gln Asp Ala Tyr Ser Ile
            275                 280                 285

Arg Cys Leu Pro Gln Val His Gly Ala Val Arg Asp Ala Leu Asp His
        290                 295                 300

Leu Arg Ala Ala Val Ala Thr Glu Leu Asn Ser Ala Thr Asp Asn Pro
305                 310                 315                 320

Leu Val Phe Pro Ser Gly Thr Val Val Ser Gly Gly Asn Phe His Gly
                325                 330                 335

Glu Val Leu Ala Leu Arg Leu Gly Tyr Ala Ala Ser Ala Leu Ala Glu
            340                 345                 350

Leu Ala Ala Ile Ser Glu Arg Arg Thr Asp Arg Leu Leu Asn Pro Glu
        355                 360                 365

Thr Gln Glu Pro Leu Glu Pro Phe Leu Ala Pro Asp Ser Gly Leu His
370                 375                 380

Ser Gly Leu Met Ile Pro Gln Tyr Thr Ala Ala Ser Leu Val Asn Asp
385                 390                 395                 400

Leu Arg Ser Leu Gly Gln Pro Ala Thr Leu Asp Asn Ala Ser Val Ser
                405                 410                 415

Gly Ala Gln Glu Asp His Val Ser Met Ser Ala Gly Ala Ala Tyr Asn
            420                 425                 430

Phe Arg Glu Ala Val Glu Lys Ala Ala Thr Val Val Gly Val Glu Leu
        435                 440                 445

Leu Cys Gly Ala Gln Gly Arg Glu Phe Leu Asp Pro Leu Ala Leu Gly
    450                 455                 460

Ala Gly Thr Ala Ala Tyr Asp Leu Val Arg Ser Glu Val Ser Glu
465                 470                 475                 480

Pro Ala Gly Asp Arg Ala Leu Ala Asp Asp Met Ala Ala Val Gly Asp
                485                 490                 495

Leu Val Arg Ala Gly Leu Val Glu Asp Ala Val Ala Arg Ala Leu Asp
                500                 505                 510

Ala

<210> SEQ ID NO 65
<211> LENGTH: 504
<212> TYPE: PRT
<213> ORGANISM: Streptomyces griseus

<400> SEQUENCE: 65

Val Val Val Gly Thr Ser Gly Thr Thr Ala Glu Asp Val Val Ala Val
1               5                   10                  15

Ala Arg His Gly Ala Arg Val Glu Leu Ser Ala Ala Val Glu Ala
            20                  25                  30

Leu Ala Ala Ala Arg Leu Ile Val Asp Ala Leu Ala Ala Lys Pro Glu
        35                  40                  45

Pro Val Tyr Gly Val Ser Thr Gly Phe Gly Ala Leu Ala Ser Arg His
    50                  55                  60

Ile Gly Thr Glu Leu Arg Ala Gln Leu Gln Arg Asn Ile Val Arg Ser
65                  70                  75                  80
```

-continued

```
His Ala Ala Gly Met Gly Pro Arg Val Glu Arg Glu Val Val Arg Ala
                 85                  90                  95
Leu Met Phe Leu Arg Leu Lys Thr Val Ala Ser Gly His Thr Gly Val
            100                 105                 110
Arg Pro Glu Val Ala Gln Thr Met Ala Asp Val Leu Asn Ala Gly Ile
        115                 120                 125
Thr Pro Val Val His Glu Tyr Gly Ser Leu Gly Cys Ser Gly Asp Leu
    130                 135                 140
Ala Pro Leu Ser His Cys Ala Leu Thr Leu Met Gly Glu Gly Glu Ala
145                 150                 155                 160
Glu Gly Pro Asp Gly Thr Val Arg Pro Ala Gly Glu Leu Leu Ala Ala
                165                 170                 175
His Gly Ile Ala Pro Val Glu Leu Arg Glu Lys Glu Gly Leu Ala Leu
            180                 185                 190
Leu Asn Gly Thr Asp Gly Met Leu Gly Met Leu Val Met Ala Leu Ala
        195                 200                 205
Asp Leu Arg Asn Leu Tyr Thr Ser Ala Asp Ile Thr Ala Ala Leu Ser
    210                 215                 220
Leu Glu Ala Leu Leu Gly Thr Asp Lys Val Leu Ala Pro Glu Leu His
225                 230                 235                 240
Ala Ile Arg Pro His Pro Gly Gln Gly Val Ser Ala Asp Asn Met Ser
                245                 250                 255
Arg Val Leu Ala Gly Ser Gly Leu Thr Gly His His Gln Asp Asp Ala
            260                 265                 270
Pro Arg Val Gln Asp Ala Tyr Ser Val Arg Cys Ala Pro Gln Val Asn
        275                 280                 285
Gly Ala Gly Arg Asp Thr Leu Asp His Ala Ala Leu Val Ala Gly Arg
    290                 295                 300
Glu Leu Ala Ser Ser Val Asp Asn Pro Val Val Leu Pro Asp Gly Arg
305                 310                 315                 320
Val Glu Ser Asn Gly Asn Phe His Gly Ala Pro Val Ala Tyr Val Leu
                325                 330                 335
Asp Phe Leu Ala Ile Val Ala Ala Asp Leu Gly Ser Ile Cys Glu Arg
            340                 345                 350
Arg Thr Asp Arg Leu Leu Asp Lys Asn Arg Ser His Gly Leu Pro Pro
        355                 360                 365
Phe Leu Ala Asp Asp Ala Gly Val Asp Ser Gly Leu Met Ile Ala Gln
    370                 375                 380
Tyr Thr Gln Ala Ala Leu Val Ser Glu Met Lys Arg Leu Ala Val Pro
385                 390                 395                 400
Ala Ser Ala Asp Ser Ile Pro Ser Ser Ala Met Gln Glu Asp His Val
                405                 410                 415
Ser Met Gly Trp Ser Ala Ala Arg Lys Leu Arg Thr Ala Val Asp Asn
            420                 425                 430
Leu Ala Arg Ile Val Ala Val Glu Leu Tyr Ala Ala Thr Arg Ala Ile
        435                 440                 445
Glu Leu Arg Ala Ala Glu Gly Leu Thr Pro Ala Pro Ala Ser Glu Ala
    450                 455                 460
Val Val Ala Ala Leu Arg Ala Gly Ala Glu Gly Pro Gly Pro Asp
465                 470                 475                 480
Arg Phe Leu Ala Pro Asp Leu Ala Ala Ala Asp Thr Phe Val Arg Glu
                485                 490                 495
```

-continued

Gly Arg Leu Val Ala Ala Val Glu
            500

<210> SEQ ID NO 66
<211> LENGTH: 502
<212> TYPE: PRT
<213> ORGANISM: Corynebacteriaceae sp.

<400> SEQUENCE: 66

Ile Thr Leu Gly Leu Ser Gly Ala Thr Ala Asp Asp Val Ile Ala Val
  1               5                  10                  15

Ala Arg His Glu Ala Arg Ile Ser Ile Ser Pro Gln Val Leu Glu Glu
             20                  25                  30

Leu Ala Ser Val Arg Ala His Ile Asp Ala Leu Ala Ser Ala Asp Thr
         35                  40                  45

Pro Val Tyr Gly Ile Ser Thr Gly Phe Gly Ala Leu Ala Thr Arg His
     50                  55                  60

Ile Ala Pro Glu Asp Arg Ala Lys Leu Gln Arg Ser Leu Ile Arg Ser
 65                  70                  75                  80

His Ala Ala Gly Met Gly Glu Pro Val Glu Arg Glu Val Val Arg Ala
                 85                  90                  95

Leu Met Phe Leu Arg Ala Lys Thr Leu Ala Ser Gly Arg Thr Gly Val
            100                 105                 110

Arg Pro Val Val Leu Glu Thr Met Val Gly Met Leu Asn Ala Gly Ile
        115                 120                 125

Thr Pro Val Val Arg Glu Tyr Gly Ser Leu Gly Cys Ser Gly Asp Leu
    130                 135                 140

Ala Pro Leu Ser His Cys Ala Leu Val Leu Met Gly Glu Gly Glu Ala
145                 150                 155                 160

Thr Asp Ala His Gly Asp Ile Arg Pro Val Pro Glu Leu Phe Ala Glu
                165                 170                 175

Ala Gly Leu Thr Pro Val Glu Leu Ala Glu Lys Glu Gly Leu Ala Leu
            180                 185                 190

Val Asn Gly Thr Asp Gly Met Leu Gly Gln Leu Ile Met Ala Leu Ala
        195                 200                 205

Asp Leu Asp Glu Leu Leu Asp Ile Ala Asp Ala Thr Ala Ala Met Ser
    210                 215                 220

Val Glu Ala Gln Leu Gly Thr Asp Gln Val Phe Arg Ala Glu Leu His
225                 230                 235                 240

Glu Pro Leu Arg Pro His Pro Gly Gln Gly Arg Ser Ala Gln Asn Met
                245                 250                 255

Phe Ala Phe Leu Ala Asp Ser Pro Ile Val Ala Ser His Arg Glu Gly
            260                 265                 270

Asp Gly Arg Val Gln Asp Ala Tyr Ser Leu Arg Cys Ser Pro Gln Val
        275                 280                 285

Thr Gly Ala Ala Arg Asp Thr Ile Ala His Ala Arg Leu Val Ala Thr
    290                 295                 300

Arg Glu Leu Ala Ala Ile Asp Asn Pro Val Val Leu Pro Ser Gly
305                 310                 315                 320

Glu Val Thr Ser Asn Gly Asn Phe His Gly Ala Pro Val Ala Tyr Val
                325                 330                 335

Leu Asp Phe Leu Ala Ile Ala Val Ala Asp Leu Gly Ser Ile Ala Glu
            340                 345                 350

Arg Arg Thr Asp Arg Met Leu Asp Pro Ala Arg Ser Arg Asp Leu Pro
        355                 360                 365

-continued

```
Ala Phe Leu Ala Asp Asp Pro Gly Val Asp Ser Gly Met Met Ile Ala
        370             375             380

Gln Tyr Thr Gln Ala Gly Leu Val Ala Glu Asn Lys Arg Leu Ala Val
385             390             395                     400

Pro Ala Ser Val Asp Ser Ile Pro Ser Ser Ala Met Gln Glu Asp His
                405             410             415

Val Ser Leu Gly Trp His Ala Ala Arg Lys Leu Arg Thr Ser Val Ala
                420             425             430

Asn Leu Arg Arg Ile Leu Ala Val Glu Met Leu Ile Ala Gly Arg Ala
            435             440             445

Leu Asp Leu Arg Ala Pro Leu Lys Pro Gly Pro Ala Thr Gly Ala Val
    450             455             460

Leu Glu Val Leu Arg Ser Lys Val Ala Gly Pro Gly Gln Asp Arg Phe
465             470             475             480

Leu Ser Ala Glu Leu Glu Ala Ala Tyr Asp Leu Leu Ala Asn Gly Ser
                485             490             495

Val His Lys Ala Leu Glu
                500
```